US 6,586,633 B1

(12) United States Patent
Yuasa et al.

(10) Patent No.: US 6,586,633 B1
(45) Date of Patent: *Jul. 1, 2003

(54) AMINE DERIVATIVES

(75) Inventors: Masayuki Yuasa, Yokohama (JP); Yukio Kawazu, Yokohama (JP); Toshimitsu Suzuki, Yokohama (JP); Toshiro Majima, Yokohama (JP); Takao Itoh, Yokohama (JP); Takuji Nakashima, Yokohama (JP); Akira Nozawa, Yokohama (JP); Hiroyuki Takimoto, Yokohama (JP); Kouji Yokoyama, Yokohama (JP)

(73) Assignee: Pola Chemical Industries, Inc., Shizuoka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/762,678

(22) PCT Filed: Aug. 11, 1998

(86) PCT No.: PCT/JP98/03563

§ 371 (c)(1),
(2), (4) Date: Apr. 5, 2001

(87) PCT Pub. No.: WO00/09475

PCT Pub. Date: Feb. 24, 2000

(51) Int. Cl.[7] .................... C07C 211/21; C07C 211/23; A01N 33/04
(52) U.S. Cl. .................... 564/384; 564/363; 564/364; 564/366; 514/649; 514/653; 514/655
(58) Field of Search .................... 564/384, 363, 564/364, 366; 514/649, 653, 655

(56) References Cited

U.S. PATENT DOCUMENTS

| 6,015,925 A | 1/2000 | Kawazu et al. |
| 6,136,863 A | 10/2000 | Kawazu et al. |

FOREIGN PATENT DOCUMENTS

| CH | 671 015 | 7/1989 |
| WO | 98/08838 | 3/1998 |

OTHER PUBLICATIONS

Database CAPLUS on STN, Acc. No. 1998:335547. Kawazu et al., JP 10139740 A2, May 26, 1998 (abstract).*
Database CAPLUS on STN, Acc. No. 1997:648524, Yuasa et al. JP 09255634 A2, Sep. 30, 1997 (abstract).*
Database CAPLUS on STN, Acc. No. 1997:805985, Halazy et al., FR 2745572 A1, Sep. 5, 1997 (abstract).*
Database CAPLUS on STN, Acc. No. 1986:129795, Grassberger et al., DE 3405334, Aug. 22, 1985 (abstract).*
Database CAPLUS on STN, Acc. No. 1989:496798, Suzuki et al., 'Benzylamine derivatives as agrochemical fungicides and their preparation.' JP 01006242 (abstract).*
Database CAPLUS on STN, Acc. No. 1998:163585, Okumura et al., 'Preparation of thienylalkoxybenzylamines and analogs as squalene epoxidase inhibitors.' WO 9808838 (abstract).*
Database CAPLUS on STN, Acc. No. 1995: 652318, Serge et al., FR 2707989 (abstract).*
Database CAPLUS on STN, Acc. No. 1992: 20925, Tsuchiya et al., EP 448078 (abstract).*
Database CAPLUS on STN, Acc. No. 1998:163585, Okumura et al., WO 9808838 (abstract).*
XP–002204909 Synthesis, vol. 12, 1988, pp. 988–990.

* cited by examiner

Primary Examiner—Brian Davis
(74) Attorney, Agent, or Firm—Oblon, Spivak, McClelland, Maier & Neustadt, P.C.

(57) ABSTRACT

The present invention relates to amine derivatives represented by formula (1) or salts thereof.

(wherein $R^1$ is C1–C4 alkyl; $R^2$ is [aryl/alkenyl group structures shown];

$R^3$ represents C1–C3 alkyl, hydroxylated C1–C5 alkyl, C1–C5 acyl; C2–C5 alkenyl, or a halogen atom; and k, l, and m are each an integer of 1 to 4.)

Exhibiting excellent antifungal effect, these compounds are highly useful as antifungal agents, antifungal compositions, drugs, etc.

18 Claims, No Drawings

AMINE DERIVATIVES

TECHNICAL FIELD

The present invention relates to novel amine derivatives exhibiting excellent antifungal activity.

BACKGROUND ART

These days, an increased number of victims suffer from superficial mycosis, led by athlete's foot. However, no reliable therapy or remedy therefor has yet been established. Thus, superficial mycosis is counted as a disease that has not yet been overcome by modern medicine. Extensive efforts have heretofore been made in an attempt toward discovery of remedies therefor, and numerous compounds have been screened for their potential antifungal action. Regrettably, not a few compounds that have been confirmed to exhibit activity in vitro or in animals are found unsatisfactory when used in actual clinical settings, and therefore, only a limited number of compounds yield satisfactory results.

In view of the foregoing, an object of the present invention is to provide novel compounds exhibiting excellent antifungal activity.

DISCLOSURE OF THE INVENTION

Under the above-described situation, the present inventors have performed extensive studies, and have found that amine derivatives represented by the below-described formula (1) exhibit excellent antifungal activity, leading to completion of the invention.

Accordingly, the present invention provides an amine derivative of formula (1):

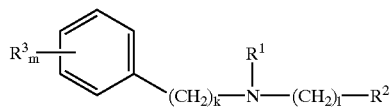

(1)

(wherein $R^1$ represents a C1–C4 linear, branched, or cyclic alkyl group; $R^2$ represents a group represented by (i), (ii), or (iii);

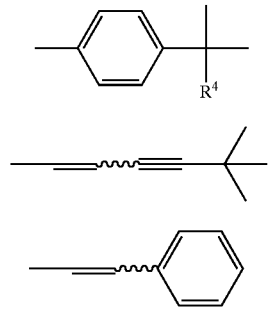

(i)

(ii)

(iii)

$R^3$ represents a C1–C3 linear, branched, or cyclic alkyl group, a hydroxylated C1–C5 linear, branched, or cyclic alkyl group, a C1–C5 linear, branched, or cyclic acyl group, a C2–C5 linear, branched, or cyclic alkenyl group, or a halogen atom;

$R^3$ in the number of m may be identical to or different from one another; k, l, and m are each an integer of 1 to 4; and $R^4$ represents a C1–C4 linear alkyl group or phenyl group) and a salt thereof.

The present invention also provides an antifungal agent comprising the amine derivative of formula (1) or a salt thereof.

The present invention also provides an antifungal composition comprising the amine derivative of formula (1) or a salt thereof.

The present invention also provides a drug comprising, as an active ingredient, the amine derivative of formula (1) or a salt thereof.

The present invention also provides a pharmaceutical composition comprising the amine derivative of formula (1) or a salt thereof, and a pharmaceutically acceptable carrier.

The present invention also provides use, as a drug, of the amine derivative of formula (1) or a salt thereof.

The present invention also provides a method for the treatment of a fungal infectious disease through administration of the amine derivative of formula (1) or a salt thereof to a patient in need thereof.

Best Mode for Carrying Out the Invention

The amine derivatives according to the present invention are represented by the aforementioned formula (1). In the formula, examples of $R^1$ representing a C1–C4 linear, branched, or cyclic alkyl group include, but are not limited to, a methyl group, an ethyl group, an n-propyl group, an isopropyl group, a cyclopropyl group, an n-butyl group, a sec-butyl group, an isobutyl group, a tert-butyl group, and a cyclobutyl group. Of these groups, C1–C3 groups; particularly, methyl, ethyl, isopropyl, and cyclopropyl groups are preferred.

$R^2$ is a group represented by (i), (ii), or (iii), with (i) and (ii) being particularly preferred.

Of the groups represented by $R^3$, examples of C1–C3 linear, branched, or cyclic alkyl groups include a methyl group, an ethyl group, an n-propyl group, an isopropyl group, and a cyclopropyl group. Of these groups, a methyl group is preferred.

Examples of preferred hydroxylated C1–C5 linear, branched, or cyclic alkyl groups include a 1-hydroxy-1-methyl ethyl group, and a 1,2-dimethyl-1-hydroxypropyl group.

Examples of the C1–C5 linear, branched, or cyclic acyl groups include a formyl group and a C2–C5 alkanoyl group. Of these groups, a formyl group, an acetyl group, and a propionyl group are preferred.

Examples of preferred ones of the C2–C5 linear, branched, or cyclic alkenyl groups include a vinyl group, an isopropenyl group, a 2-methyl-1-propenyl group, a 1-ethylvinyl group, a 1-methyl-1-propenyl group, and a 1-isopropylvinyl group.

Examples of the halogen atoms include a fluorine atom, a chlorine atom, a bromine atom, and an iodine atom.

Preferred examples of $R^3$ include, among others, a methyl group, a 1-hydroxy-1-methylethyl group, a 1,2-dimethyl-1-hydroxypropyl group, a 1-hydroxypropyl group, a formyl group, an acetyl group, a propionyl group, a vinyl group, an isopropenyl group, a 2-methyl-1-propenyl group, a 1-ethylvinyl group, a 1-methyl-1-propenyl group, a 1-isopropyl vinyl group, a fluorine atom, and a bromine atom.

$R^3$ groups appearing in the number of m may be identical to or different from one another.

Of the $R^3$ groups, at least one group is preferably a C2–C5 linear, branched, or cyclic alkenyl group; particularly, a vinyl group, an isopropenyl group, a 2-methyl-1-propenyl group, a 1-ethylvinyl group, a 1-methylpropenyl group, or a 1-isopropylvinyl group.

k, l, and m are each independently an integer of 1 to 4. Preferably, k is 1, l is 1, and m is 1–3.

$R^4$ represents a C1–C4 linear alkyl group or phenyl group. Particularly, a methyl group and a phenyl group are preferred.

Specific examples of preferred amine derivatives of formula (1) include the following.

Trans-3'-[N-(6,6-dimethyl-2-hepten-4-ynyl)-N-methylaminomethyl]acetophenone,
Trans-N-(6,6-dimethyl-2-hepten-4-ynyl)-N-methyl-(3-isopropenylbenzyl)amine,
Cis-3'-[N-(6,6-dimethyl-2-hepten-4-ynyl)-N-methylaminomethyl]acetophenone,
Cis-N-(6,6-dimethyl-2-hepten-4-ynyl)-N-methyl-(3-isopropenylbenzyl)amine,
Trans-N-(6,6-dimethyl-2-hepten-4-ynyl)-N-methyl-(3-bromobenzyl)amine,
Trans-3-[N-(6,6-dimethyl-2-hepten-4-ynyl)-N-methylaminomethyl]benzaldehyde,
Trans-N-(6,6-dimethyl-2-hepten-4-ynyl)-N-methyl-(3-vinylbenzyl)amine,
Trans-N-(6,6-dimethyl-2-hepten-4-ynyl)-N-methyl-[3-(2-methyl-1-propenyl)benzyl]amine,
Trans-3'-[N-cyclopropyl-N-(6,6-dimethyl-2-hepten-4-ynyl)aminomethyl]acetophenone,
Trans-N-cyclopropyl-N-(6,6-dimethyl-2-hepten-4-ynyl)-(3-isopropenylbenzyl)amine,
Trans-N-(6,6-dimethyl-2-hepten-4-ynyl)-N-methyl-(3-bromo-5-methylbenzyl)amine,
2-[3-{N-(6,6-dimethyl-2-hepten-4-ynyl)-N-methylaminomethyl}-5-methylphenyl]-2-propanol,
Trans-N-(6,6-dimethyl-2-hepten-4-ynyl)-N-methyl-(3-isopropenyl-5-methylbenzyl)amine,
2-[3-{N-(6,6-dimethyl-2-hepten-4-ynyl)-N-methylaminomethyl}phenyl]-3-methyl-2-butanol,
Trans-N-(6,6-dimethyl-2-hepten-4-ynyl)-N-methyl-[3-(1-isopropylvinyl)benzyl]amine,
Trans-3'-[N-(6,6-dimethyl-2-hepten-4-ynyl)-N-methylaminomethyl]propiophenone,
Trans-N-(6,6-dimethyl-2-hepten-4-ynyl)-N-methyl-[3-(1-ethylvinyl)benzyl]amine,
Trans,cis-N-(6,6-dimethyl-2-hepten-4-ynyl)-N-methyl-[3-(1-methyl-1-propenyl)benzyl]amine,
Trans-N-(6,6-dimethyl-2-hepten-4-ynyl)-N-methyl-(3-bromo-4-fluorobenzyl)amine,
Trans-2-[2-fluoro-5-{N-(6,6-dimethyl-2-hepten-4-ynyl)-N-methylaminomethyl}phenyl]-2-propanol,
Trans-N-(6,6-dimethyl-2-hepten-4-ynyl)-N-methyl-(4-fluoro-3-isopropenylbenzyl)amine,
Trans-N-(6,6-dimethyl-2-hepten-4-ynyl)-N-methyl-(5-bromo-2-methylbenzyl)amine,
Trans-2-[3-{N-(6,6-dimethyl-2-hepten-4-ynyl)-N-methylaminomethyl}-4-methylphenyl]-2-propanol,
Trans-N-(6,6-dimethyl-2-hepten-4-ynyl)-N-methyl-(5-isopropenyl-2-methylbenzyl)amine,
Trans-N-(6,6-dimethyl-2-hepten-4-ynyl)-N-methyl-(2-bromobenzyl)amine,
2-[3-{N-(6,6-dimethyl-2-hepten-4-ynyl)-N-methylaminomethyl}phenyl]-2-propanol,
Trans-N-(6,6-dimethyl-2-hepten-4-ynyl)-N-methyl-(2-isopropenylbenzyl)amine,
Trans-3'-[N-(6,6-dimethyl-2-hepten-4-ynyl)-N-isopropylaminomethyl]acetophenone,
Trans-N-(6,6-dimethyl-2-hepten-4-ynyl)-N-isopropyl-(3-isopropenylbenzyl)amine,
Trans-3'-[N-(6,6-dimethyl-2-hepten-4-ynyl)-N-ethylaminomethyl]acetophenone,
Trans-N-(6,6-dimethyl-2-hepten-4-ynyl)-N-ethyl-(3-isopropenylbenzyl)amine,
3'-(N-cinnamyl-N-methylaminomethyl)acetophenone,
N-cinnamyl-N-methyl-(3-isopropenylbenzyl)amine,
Trans-N-(6,6-dimethyl-2-hepten-4-ynyl)-N-methyl-(3-bromo-2-methylbenzyl)amine,
Trans-2-[3-{N-(6,6-dimethyl-2-hepten-4-ynyl)-N-methylaminomethyl}-2-methylphenyl-2-propanol,
Trans-N-(6,6-dimethyl-2-hepten-4-ynyl)-N-methyl-(3-isopropenyl-2-methylbenzyl)amine,
Trans-N-(6,6-dimetnyl-2-hepten-4-ynyl)-N-methyl-(2-bromo-6-methylbenzyl)amine,
Trans-2-[2-{N-(6,6-dimethyl-2-hepten-4-ynyl)-N-methylaminomethyl}-3-methylphenyl]-2-propanol,
Trans-N-(6,6-dimethyl-2-hepten-4-ynyl)-N-methyl-(2-isopropenyl-6-methylbenzyl)amine,
Trans-N-(6,6-dimethyl-2-hepten-4-ynyl)-N-methyl-(5-bromo-2-fluorobenzyl)amine,
Trans-2-[3-{N-(6,6-dimethyl-2-hepten-4-ynyl)-N-methylaminomethyl}-4-fluorophenyl]-2-propanol,
Trans-N-(6,6-dimethyl-2-hepten-4-ynyl)-N-methyl-(2-fluoro-5-isopropenylbenzyl)amine,
Trans-N-(6,6-dimethyl-2-hepten-4-ynyl)-N-methyl-(3-bromo-5-fluorobenzyl)amine,
Trans-2-[3-{N-(6,6-dimethyl-2-hepten-4-ynyl)-N-methylaminomethyl)-5-fluorophenyl]-2-propanol,
Trans-N-(6,6-dimethyl-2-hepten-4-ynyl)-N-methyl-(3-fluoro-5-isopropenylbenzyl)amine,
Trans-N-(6,6-dimethyl-2-hepten-4-ynyl)-N-methyl-(3,5-dibromobenzyl)amine,
Trans-2-[5-bromo-3-{N-(6,6-dimethyl-2-hepten-4-ynyl)-N-methylaminomethyl}phenyl]-2-propanol,
Trans-N-(6,6-dimethyl-2-hepten-4-ynyl)-N-methyl-(3-bromo-5-isopropenylbenzyl)amine,
Trans-2-[3-{N-(6,6-dimethyl-2-hepten-4-ynyl)-N-methylaminomethyl}-5-isopropenylphenyl]-2-propanol,
Trans-N-(6,6-dimethyl-2-hepten-4-ynyl)-N-methyl-(3,5-bisisopropenylbenzyl)amine,
Trans-N-(6,6-dimethyl-2-hepten-4-ynyl)-N-methyl-(3-bromo-4-methylbenzyl)amine,
Trans-2-[5-{N-(6,6-dimethyl-2-hepten-4-ynyl)-N-methylamionomethyl}-2-methylphenyl]-2-propanol,
Trans-N-(6,6-dimethyl-2-hepten-4-ynyl)-N-methyl-(3-isopropenyl-4-methylbenzyl)amine,
3'-[N-(4-tert-butylbenzyl)-N-methylaminomethyl]acetophenone,
N-(4-tert-butylbenzyl)-N-methyl-(3-isopropenylbenzyl)amine,
N-(4-tert-butylbenzyl)-N-methyl-(3-bromobenzyl)amine,
3-[N-(4-tert-butylbenzyl)-N-methylaminomethyl]benzaldehyde,
N-(4-tert-butylbenzyl)-N-methyl-(3-vinylbenzyl)amine, 3'-[N-(4-tert-butylbenzyl)-N-cyalopropylaminomethyl]acetophenone,
N-(4-tert-butylbenzyl)-N-cyclopropyl-(3-isopropenylbenzyl)amine,
N-(4-tert-butylbenyzyl)-N-methyl-(3-bromo-5-methylbenzyl)amine,
2-[3-{-(4-tert-butylbenzyl)-N-methylaminomethyl}-5-methylphenyl]-2-propanol,
N-(4-tert-butylbenzyl)-N-methyl-(3-isopropenyl-5-methylbenzyl)amine,
2-[3-{N-(4-tert-butylbenzyl)-N-methylaminomethyl}phenyl]-3-methyl-2-butanol,
N-(4-tert-butylbenzyl)-N-methyl-[3-(1-isopropylvinyl)benzyl]amine,
1-[3-{N-(4-tert-butylbenzyl)-N-methylaminomethyl}phenyl]-1-propanol,
3'-[N-(4-tert-butylbenzyl)-N-methylaminomethyl]propiophenone,
N-(4-tert-butylbenzyl)-N-methyl-[3-(1-ethylvinyl)benzyl]amine,
Cis-N-(4-tert-butylbenzyl)-N-methyl-[3-(1-methyl-1-propenyl)benzyl]amine,
N-(4-tert-butylbenzyl)-N-methyl-(3-bromo-5-fluorobenzyl)amine,
2-[3-{N-(4-tert-butylbenzyl)-N-methylaminomethyl}-5-fluorophenyl]-2-butanol,
N-(4-tert-butylbenzyl)-N-methyl-(3-fluoro-5-isopropenylbenzyl)amine,
3'-[N-4-(1-methyl-1-phenylethyl)benzyl-N-methylaminomethyl]acetophenone,
N-methyl-N-[4-(1-methyl-1-phenylethyl)benzyl]-(3-isopropenylbenzyl)amine,
N-(4-tert-butylbenzyl)-N-methyl-(2-bromobenzyl)amine,
2-[3-{N-(4-tert-butylbenzyl)-N-methylaminomethyl}phenyl]-2-propanol,
N-(4-tert-butylbenzyl)-N-methyl-(2-isopropenylbenzyl)amine,
3'-[N-(4-tert-butylbenzyl)-N-isopropylaminomethyl]acetophenone,
N-(4-tert-butylbenzyl)-N-isopropyl-(3-isopropenylbenzyl)amine,
3'-[N-(4-tert-butylbenzyl)-N-ethylaminomethyl]acetophenone,
N-(4-tert-butylbenzyl)-N-ethyl-(3-isopropenylbenzyl)amine,
N-(4-tert-butylbenzyl)-N-methyl-(3-bromo-2-methylbenzyl)amine,
2-[3-{N-(4-tert-butylbenzyl)-N-methylaminomethyl}-2-methylphenyl]-2-propanol,
N-(4-tert-butylbenzyl)-N-methyl-(3-isopropenyl-2-methylbenzyl)amine,
N-(4-tert-butylbenzyl)-N-methyl-(2-bromo-6-methylbenzyl)amine,
2-[2-{N-(4-tert-butylbenzyl)-N-methylaminomethyl}-3-methylphenyl]-2-propanol,
N-(4-tert-butylbenzyl)-N-methyl-(2-isopropenyl-6-methylbenzyl)amine,
N-(4-tert-butylbenzyl)-N-methyl-(3-bromo-4-methylbenzyl)amine,
2-[5-{N-(4-tert-butylbenzyl)-N-methylaminomethyl}-2-methylphenyl]-2-propanol,
N-(4-tert-butylbenzyl)-N-methyl-(3-isopropenyl-4-methylbenzyl)amine,
N-(4-tert-butylbenzyl)-N-methyl-(3-bromo-4-fluorobenzyl)amine,
2-[5-{N-(4-tert-butylbenzyl)-N-methylaminomethyl}-2-fluorophenyl]-2-propanol,
N-(4-tert-butylbenzyl)-N-methyl-(4-fluoro-3-isopropenylbenzyl)amine,
N-(4-tert-butylbenzyl)-N-methyl-(5-bromo-2-fluorobenzyl)amine,
2-[3-{N-(4-tert-butylbenzyl)-N-methylaminomethyl}-4-fluorophenyl]-2-propanol,
N-(4-tert-butylbenzyl)-N-methyl-(2-fluoro-5-isopropenylbenzyl)amine,
N-(3-bromo-5-methylbenzyl)-N-methyl-[4-(1-methyl-1-phenylethyl)benzyl]amine,
2-[3-methyl-5-[N-methyl-N-{4-(1-methyl-1-phenylethyl)benzyl}aminomethyl]phenyl]-2-propanol,
N-methyl-N-[4-(1-methyl-1-phenylethyl)benzyl]-(3-isopropenyl-5-methylbenzyl)amine,
N-(4-tert-butylbenzyl)-N-methyl-(3,5-dibromobenzyl)amine,
2-[3-bromo-5-{N-(4-tert-butylbenzyl)-N-methylaminomethyl}phenyl]-2-propanol,
N-(4-tert-butylbenzyl)-N-methyl-(3-bromo-5-isopropenylbenzyl)amine,
2-[3-isopropenyl-5-{N-(4-tert-butylbenzyl)-N-methylaminomethyl}phenyl]-2-propanol, and
N-(4-tert-butylbenzyl)-N-methyl-(3,5-bisisopropenylbenzyl)amine.

Of the above-listed compounds, the following compounds are more preferred:
Trans-N-(6,6-dimethyl-2-hepten-4-ynyl)-N-methyl-(3-isopropenylbenzyl)amine,
Cis-N-(6,6-dimethyl-2-hepten-4-ynyl)-N-methyl-(3-isopropenylbenzyl)amine,
Trans-N-(6,6-dimethyl-2-hepten-4-ynyl)-N-methyl-(3-vinylbenzyl)amine,
Trans-N-(6,6-dimethyl-2-hepten-4-ynyl)-N-methyl-[3-(2-methyl-1-propenyl)benzyl]amine,
Trans-N-cyclopropyl-N-(6,6-dimethyl-2-hepten-4-ynyl)-(3-isopropenylbenzyl)amine,
Trans-N-(6,6-dimethyl-2-hepten-4-ynyl)-N-methyl-(3-isopropenyl-5-methylbenzyl)amine,
Trans-N-(6,6-dimethyl-2-hepten-4-ynyl)-N-methyl-[3-(1-isopropylvinyl)benzyl]amine,
Trans-N-(6,6-dimethyl-2-hepten-4-ynyl)-N-methyl-[3-(1-ethylvinyl)benzyl]amine,
Trans,cis-N-(6,6-dimethyl-2-hepten-4-ynyl)-N-methyl-[3-(1-methyl-1-propenyl)benzyl]amine,
Trans-N-(6,6-dimethyl-2-hepten-4-ynyl)-N-methyl-(4-fluoro-3-isopropenylbenzyl)amine,
Trans-N-(6,6-dimethyl-2-hepten-4-ynyl)-N-methyl-(5-isopropenyl-2-methylbenzyl)amine,
Trans-N-(6,6-dimethyl-2-hepten-4-ynyl)-N-methyl-(2-isopropenylbenzyl)amine,
Trans-N-(6,6-dimethyl-2-hepten-4-ynyl)-N-isopropyl-(3-isopropenylbenzyl)amine,
Trans-N-(6,6-dimethyl-2-hepten-4-ynyl)-N-ethyl-(3-isopropenylbenzyl)amine,
N-cinnamyl-N-methyl-(3-isopropenylbenzyl)amine,
Trans-N-(6,6-dimethyl-2-hepten-4-ynyl)-N-methyl-(3-isopropenyl-2-methylbenzyl)amine, Trans-N-(6,6-dimethyl-2-hepten-4-ynyl)-N-methyl-(2-isopropenyl-6-methylbenzyl)amine,
Trans-N-(6,6-dimethyl-2-hepten-4-ynyl)-N-methyl-(2-fluoro-5-isopropenylbenzyl)amine,
Trans-N-(6,6-dimethyl-2-hepten-4-ynyl)-N-methyl-(3-fluoro-5-isopropenylbenzyl)amine,
Trans-N-(6,6-dimethyl-2-hepten-4-ynyl)-N-methyl-(3-bromo-5-isopropenylbenzyl)amine,
Trans-2-[3-{N-(6,6-dimethyl-2-hepten-4-ynyl)-N-methylaminomethyl}-5-isopropenylphenyl]-2-propanol,
Trans-N-(6,6-dimethyl-2-hepten-4-ynyl)-N-methyl-(3,5-bisisopropenylbenzyl)amine,
Trans-N-(6,6-dimethyl-2-hepten-4-ynyl)-N-methyl-(3-isopropenyl-4-methylbenzyl)amine,
N-(4-tert-butylbenzyl)-N-methyl-(3-isopropenylbenzyl)amine,
N-(4-tert-butylbenzyl)-N-methyl-(3-vinylbenzyl)amine,
N-(4-tert-butylbenzyl)-N-cyclopropyl-(3-isopropenylbenzyl)amine,
N-(4-tert-butylbenzyl)-N-methyl-(3-isopropenyl-5-methylbenzyl)amine,
N-(4-tert-butylbenzyl)-N-methyl-[3-(1-isopropylvinyl)benzyl]amine,
N-(4-tert-butylbenzyl)-N-methyl-[3-(1-ethylvinyl)benzyl]amine,
Cis-N-(4-tert-butylbenzyl)-N-methyl-[3-(1-methyl-1-propenyl)benzyl]amine,
N-(4-tert-butylbenzyl)-N-methyl-(3-fluoro-5-isopropenylbenzyl)amine,
N-methyl-N-[4-(1-methyl-1-phenylethyl)benzyl]-(3-isopropenylbenzyl)amine,
N-(4-tert-butylbenzyl)-N-methyl-(2-isopropenylbenzyl)amine,
N-(4-tert-butylbenzyl)-N-isopropyl-(3-isopropenylbenzyl)amine,
N-(4-tert-butylbenzyl)-N-ethyl-(3-isopropenylbenzyl)amine,
N-(4-tert-butylbenzyl)-N-methyl-(3-isopropenyl-2-methylbenzyl)amine,
N-(4-tert-butylbenzyl)-N-methyl-(2-isopropenyl-6-methylbenzyl)amine,
N-(4-tert-butylbenzyl)-N-methyl-(3-isopropenyl-4-methylbenzyl)amine,
N-(4-tert-butylbenzyl)-N-methyl-(4-fluoro-3-isopropenylbenzyl)amine,
N-(4-tert-butylbenzyl)-N-methyl-(2-fluoro-5-isopropenylbenzyl)amine,
N-methyl-N-[4-(1-methyl-1-phenylethyl)benzyl]-(3-isopropenyl-5-methylbenzyl)amine,
N-(4-tert-butylbenzyl)-N-methyl-(3-bromo-5-isopropenylbenzyl)amine,
2-[3-isopropenyl-5-(N-(4-tert-butylbenzyl)-N-methylaminomethyl}phenyl]-2-propanol, and
N-(4-tert-butylbenzyl)-N-methyl-(3,5-bisisopropenylbenzyl)amine.

Salts which may be used in the present invention are not particularly limited, so long as they are physiologically acceptable. Preferred examples of such salts include salts of mineral acids such as hydrochloric acid, sulfuric acid, nitric acid, and phosphoric acid; salts of organic acids such as citric acid, oxalic acid, fumaric acid, maleic acid, formic acid, acetic acid, methanesulfonic acid, benzenesulfonic acid, paratoluenesulfonic acid, and corbonic acid. Of these salts, hydrochloric acid salts are particularly preferred. These salts can be obtained from an amine derivative of formula (1) and an acid according to a customary method; for example, an amine derivative of formula (1) and an acid are mixed in a polar or non-polar solvent.

The compounds of formula (1) according to the present invention encompass solvates, such as hydrates.

The compounds of formula (1) according to the present invention may be prepared through, for example, the following reaction scheme (I) or (II).

(Process I)

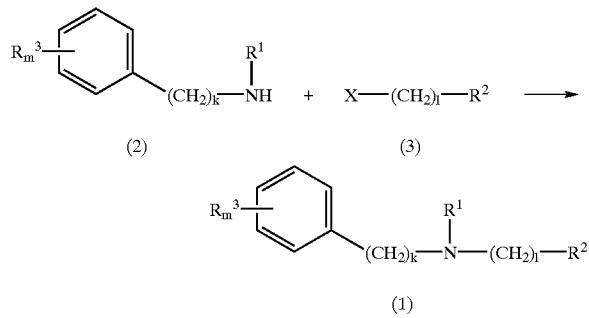

(Process II)

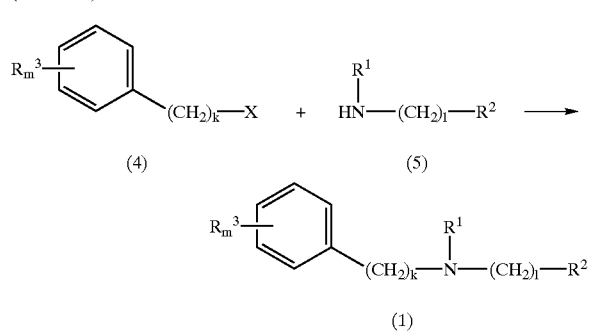

(wherein $R^1$, $R^2$, $R^3$, k, l, and m have the same meanings, and X represents a halogen atom.)

Briefly, a secondary amine derivative (2) or a salt thereof and a halide (3) are subjected to a condensation reaction (Process 1), or alternatively, a halide (4) and a secondary amine derivative (5) or a salt thereof are subjected to a condensation reaction (Process 11), to thereby yield an amine derivative (1) of the present invention. The condensation reactions may be performed through use of a condensing agent in the presence of a solvent.

In either process (I) or (II), the ratio of the raw materials; i.e., the ratio of the secondary amine derivative to the halide, is generally preferably from 0.1 to 10.0 by mol, and particularly preferably from 1.0 to 2.5 by mol. The condensing agent used in the reaction is a tertiary organic amine or an inorganic base. Specifically, mention may be given of, among others, triethylamine, N,N-diisopropylethylamine, anhydrous potassium carbonate, and anhydrous sodium carbonate. Any of these condensing agents is generally used in an amount of 0.1 to 30.0 mol, preferably from 2.0 to 5.0 mol, on the basis of the entirety of the raw materials.

The solvent to be used in the reaction is not particularly limited so long as it is a non-aqueous solvent that can dissolve therein the two raw materials. A specific example is N,N-dimethylformamide. The amount of the solvent is preferably 5 to 100 times the amount of the reactive starting materials. The solvent may be used singly or in combination of two or more species. Selection of the solvent is performed in accordance with physical properties of the starting compound and condensing agent employed.

The reaction temperature may be any temperature between room temperature and the boiling point of the solvent. Preferably, the reaction temperature is room temperature. The reaction time may vary depending on conditions, and generally, it requires 10 minutes to 30 days. Post-treatment and purification may be performed according to customary methods; for example, quenching with water, extraction with a solvent, column chromatography, and recrystallization, which may be combined appropriately.

The compounds of formula (1) according to the present invention may be produced through, for example, the following reaction scheme III or IV.

(Process III)

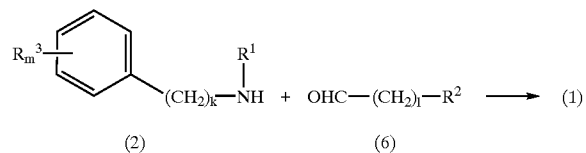

(Process IV)

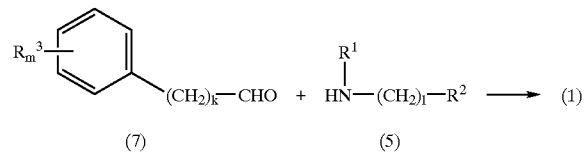

(wherein $R^1$, $R^2$, $R^3$, k, l, and m have the same meanings.)

Briefly, a secondary amine derivative (2) or a salt thereof and an aldehyde derivative (6) are subjected to a condensation reaction (Process III), or alternatively, an aldehyde derivative (7) and a secondary amine derivative (5) or a salt thereof are subjected to a condensation reaction (Process IV), to thereby yield an amine derivative (1) of the present invention. The condensation reactions may be performed by causing a reaction between an amine moiety and an aldehyde moiety, and then forming a tertiary amine moiety through use of a reducing agent.

In either process (III) or (IV), the ratio of the raw materials; i.e., the ratio of the secondary amine derivative to the aldehyde derivative, is generally preferably from 0.1 to 10.0 by mol, and particularly preferably from 1.0 to 2.5 by mol.

The solvent to be used in the reaction is not particularly limited so long as it is a non-aqueous solvent that can dissolve therein the two raw materials. A specific example is methanol. The amount of the solvent is preferably 5 to 100 times the amount of the reactive starting materials. The solvent may be used singly or in combination of two or more species. Selection of the solvent is performed in accordance with physical properties of the starting compound and condensing agent employed.

First, in order to carry out the reaction between a secondary amine derivative and an aldehyde derivative, the reaction system is preferably turned to basic by use of an inorganic base such as potassium hydroxide or sodium hydroxide, or an organic base such as triethylamine or N,N-diisopropylethylamine. The reaction temperature may be any temperature between room temperature and the boiling point of the solvent. Preferably, the reaction temperature is room temperature. The reaction time may vary depending on the conditions, and generally, it requires 10 minutes to 30 days.

Next, in order to perform a reaction with a reducing agent, the reducing agent is caused to react as is without isolating the intermediate obtained from the two raw materials. Examples of the reducing agent which may be used include sodium cyanoborohydride and sodium borohydride. The amount of the reducing agent is determined in accordance with the amount of the raw materials employed. The time during which the reducing agent is reacted may vary depending on the conditions, and generally, it requires 10 minutes to 30 days. Post-treatment and purification may be performed according to customary methods; for example, quenching with water, extraction with a solvent, column chromatography, and recrystallization, which may be combined appropriately.

When substituent conversion is performed before or after any of Processes I to IV, other amine derivatives of formula (1) may be obtained. Specific examples of such substituent conversion include:

halogenation by use of N-bromosuccinimide, phosphorus tribromide, etc.;

conversion of a primary amino group to a secondary amino group by use of an alkyl halide;

conversion of a carbonyl group to a C=C double bond through the Wittig reaction, such as from formyl to vinyl, formyl to 2-methyl-1-propenyl, acetyl to isopropenyl, acetyl to 1-methyl-1-propenyl, propionyl to 1-ethylvinyl, etc.;

halogen-metal exchange reaction between, for example, an aromatic halogen atom and n-butyl lithium, and subsequent reaction with an acylation source such as N,N-dimethylformamide for conversion into an acyl group, such as a formyl group;

halogen-metal exchange reaction between, for example, an aromatic halogen atom and n-butyl lithium, and subsequent reaction with a ketone such as acetone or 3-methyl-2-butanone for conversion into a 1-hydroxy-1-methylethyl group, a 1,2-dimethyl-1-hydroxypropyl group, etc.; and creation of a C=C double bond characterized by dehydration reaction by use of phosphorus oxychloride; e.g., conversion from a 1-hydroxy-1-methylethyl group into an isopropenyl group, from a 1,2-dimethyl-1-hydroxypropyl group to a 1-isopropylvinyl group.

The amine derivatives of the formula (1) according to the present invention or salts thereof exhibit excellent antifungal activity, and thus are very useful in the manufacture of antifungal compositions, drugs containing the derivatives, and so on.

The antifungal compositions of the present invention can be produced through incorporation of one or more species of the amine derivatives (1) or salts thereof. No particular limitation is imposed on the type of the compositions, so long as they are compositions known to contain antifungal agents. Examples of such compositions include pharmaceutical compositions such as topical skin agents, and external agents for washing or sterilization; clothing such as socks and underwear; and plastics such as toothbrushes and ball-point pens. Of these, topical skin agents are most preferred. The amine derivatives (1) of the present invention or salts thereof may be formulated into a composition through known techniques. For example, when pharmaceutical compositions are to be prepared, a compound of the present invention may be emulsified or solubilized along with other ingredients, or alternatively, the compound may be admixed with powder ingredients and then granulated. When clothing are produced, the compound may be melt-kneaded during the fiber production step, followed by spinning, or alternatively, clothing may be impregnated with the compound. When plastic products are produced, incorporation of the compound through melt-kneading is preferred. Also, wood or similar materials may be impregnated with the compound for the purpose of anti-molding.

Compositions of the present invention may include, other than the amine derivatives (1) or salts thereof, arbitrary ingredients which are generally contained in such compositions, as needed. The arbitrary ingredients are not particularly limited, and when pharmaceutical compositions are prepared, coloring agents, sweetening/flavoring agents, binders, disintegrators, coating agents, stabilizers, pH regulators, sugar coaters, emulsification/dispersing/solubilizing agents, etc. may be incorporated. Of these, when topical skin agents are prepared, the following may be incorporated: hydrocarbons such as liquid paraffin and VASELINE; esters such as spermaceti and beeswax; triglycerides such as olive oil and beef tallow; higher alcohols such as cetanol and oleyl alcohol; fatty acids such as stearic acid and oleic acid; polyols such as propylene glycol and glycerol; nonionic surfactants; anionic surfactants; cationic surfactants; and thickeners. When clothing and plastic products are produced, plasticizers, cross-linking agents, colorants, antioxidants, and UV absorbers may be incorporated. The amount of the amine derivatives or salts thereof to be incorporated into the compositions of the present invention is not particularly limited, and is preferably 0.001–20 wt. %, more preferably 0.01–15 wt. %, most preferably 0.1–10 wt. %.

EXAMPLES

The present invention will next be described in more detail by way of examples, which should not be construed as limiting the invention thereto.

Referential Example 1

Production of 3'-Bromomethylacetophenone

3'-Methylacetophenone (5.00 g; 37.3 mmol), N-bromosuccinimide (6.63 g; 37.3 mmol), and benzoyl peroxide (100 mg) were added to carbon tetrachloride (70 ml), and the mixture was refluxed for 1 hour. The mixture was left to cool to room temperature, and crystals that precipitated were removed by filtration. The filtrate was evaporated under reduced pressure, and the residue was purified by silica gel column chromatography (n-hexane:ethyl acetate=20:1), to thereby yield 3.08 g of the target compound (yield: 38.8%).

$^1$H-NMR (CDCl$_3$, ppm); 2.62 (3H, s), 4.53 (2H, s), 7.46 (1H, t, J=7.83 Hz), 7.62 (1H, dt, J=7.83 Hz, (16.2 Hz)), 7.89 (1H, dt, J=7.83 Hz, 1.62 Hz), 7.97 (1H, t, J=1.62 Hz).

Example 1

Production of trans-3'-[N-(6,6-Dimethyl-2-hepten-4-ynyl)-N-methylaminomethyl]acetophenone (Compound 1)

N-(6,6-dimethyl-2-hepten-4-ynyl)methylamine (trans:cis=about 3:1) (1.06 g; 7.04 mmol) and potassium carbonate (1.95 g; 14.1 mmol) were added to N,N-dimethylformamide (20 ml). While the mixture was stirred in an ice bath, 3'-bromomethylacetophenone (1.31 g; 6.15 mmol) in N,N-dimethylformamide (15 ml) was added dropwise. After completion of addition, the mixture was removed from the ice bath, and stirred for 15 minutes at room temperature. Reaction was stopped by pouring the mixture into ice+saturated aqueous sodium bicarbonate solution, followed by extraction with ethyl acetate (100 ml). The organic layer was washed with saturated aqueous sodium bicarbonate solution and with saturated brine, and dried over anhydrous sodium sulfate. The solvent was evaporated under reduced pressure, and the residue was purified by silica gel column chromatography (chloroform), to thereby yield 1.54 g of the target compound (yield: 88.4%).

$^1$H-NMR (CDCl$_3$, ppm); 1.24 (9H, s), 2.19 (3H, s), 2.61 (3H, s), 2.90 (2H, d, J=7.29 Hz), 5.34 (2H, s), 5.66 (1H, d, J=15.7 Hz), 6.09 (1H, dt, J=15.7 Hz, 7.29 Hz), 7.41 (1H, t, J=7.29 Hz), 7.54 (1H, m), 7.85 (1H, m), 7.89 (1H, s).

Example 2

Production of trans-N-(6,6-Dimethyl-2-hepten-4-ynyl)-N-methyl-(3-isopropenylbenzyl)amine (Compound 2)

Methyl triphenylphosphonium bromide (2.33 g; 6.52 mmol) was suspended in tetrahydrofuran (15 ml). While the suspension was stirred under nitrogen atmosphere at room temperature, n-butyl lithium in n-hexane (1.68 M: 4.6 ml; 7.82 mmol) was added dropwise. After the reaction mixture turned deep red, the mixture was cooled in an ice bath, and Compound 1 (1.54 g; 5.43 mmol) in tetrahydrofuran (15 ml) was added dropwise thereto. After completion of the addition, the mixture was removed from the ice bath, and stirred for 30 minutes at room temperature. Reaction was stopped by pouring the mixture into ice/water, followed by extraction with ether (100 ml). The organic layer was washed with saturated aqueous sodium bicarbonate solution and with saturated brine, and dried over anhydrous sodium sulfate. The solvent was evaporated under reduced pressure, and the residue was purified by silica gel column chromatography (n-hexane:ethyl acetate=10:1), to thereby yield 0.69 g of the target compound (yield: 45.2%).

$^1$H-NMR (CDCl$_3$, ppm); 1.24 (9H, s), 2.11 (3H, s), 2.16 (3H, s), 3.05 (2H, dd, J=6.89 Hz, 1.35 Hz), 3.49 (2H, s), 5.08 (1H, s), 5.37 (1H, s), 5.65 (1H, dt, J=15.7 Hz, 1.35 Hz), 6.10 (1H, dt, J=15.7 Hz, 6.89 Hz), 7.20~7.40 (4H, m).

Example 3

Production of trans-N-(6,6-Dimethyl-2-hepten-4-ynyl)-N-methyl-(3-isopropenylbenzyl)amine Hydrochloride (Compound 3)

Compound 2 (0.69 g; 2.45 mmol) was dissolved in diisopropylether (200 ml). While the solution was stirred at room temperature, hydrogen chloride in ethyl acetate (4N: 0.73 ml; 2.94 mmol) was added dropwise. The mixture was stirred for 6 hours at room temperature, and white crystals that precipitated were collected by filtration. The crystals were washed with diisopropyl ether, followed by drying in a desiccator under reduced pressure, to thereby yield 0.70 g of the target compound as white crystals (yield: 89.9%).

IR (KBr tablet, cm$^{-1}$); 2969, 2950, 2930, 2604, 2564, 2482, 1469, 1458, 897; m. p. 166~167° C.; $^1$H-NMR (CDCl$_3$, ppm); 1.25 (9H, s), 2.19 (3H, s), 2.64 (3H, d, J=4.59 Hz), 3.47~3.71 (2H, m), 4.00~4.26 (2H, m), 5.17 (1H, s), 5.48 (1H, s), 5.84 (1H, d, J=15.9 Hz), 6.28 (1H, m), 7.41 (1H, t, J=4.86 Hz), 7.51~7.57 (2H, m), 7.74 (1H, s).

Example 4

Production of cis-3'-[N-(6,6-Dimethyl-2-hepten-4-ynyl)-N-methylaminomethyl]acetophenone (Compound 4)

The procedure described in Example 1 was repeated, except that N-(6,6-dimethyl-2-hepten-4-ynyl)methylamine (trans:cis=about 3:1) (17.7 g; 116.8 mmol), sodium carbonate (17.7 g; 166.8 mmol), and 3'-bromomethylacetophenone (23.7 g; 111.2 mmol) were used, to thereby yield 4.67 g of the target compound (yield: 14.8%).

$^1$H-NMR (CDCl$_3$, ppm); 1.23 (9H, s), 2.22 (3H, s), 2.62 (3H, s), 3.28 (2H, dd, J=7.02 Hz, 1.35 Hz), 3.57 (2H, s), 5.63 (1H, dt, J=11.1 Hz, 1.35 Hz), 5.77 (1H, dt, J=11.1 Hz, 6.75 Hz), 7.42 (1H, t, J=7.29 Hz), 7.55 (1H, d, J=7.29 Hz), 7.85 (1H, dt, J=7.29 Hz, 1.35 Hz), 7.90 (1H, s).

Example 5

Production of cis-N-(6,6-Dimethyl-2-hepten-4-ynyl)-N-methyl-(3-isopropenylbenzyl)amine (Compound 5)

The procedure described in Example 2 was repeated, except that methyl triphenylphosphonium bromide (7.65 g; 21.4 mmol), n-butyl lithium in n-hexane (1.63 M: 4.4 ml; 23.5 mmol), and Compound 4 (7.65 g; 21.4 mmol) were used, to thereby yield 0.65 g of the target compound (yield: 14.0%).

$^1$H-NMR (CDCl$_3$, ppm); 1.24 (9H, s), 2.16 (3H, s), 2.23 (3H, s), 3.28 (2H, dd, J=6.89 Hz, 1.49 Hz), 3.50 (2H, s), 5.08 (1H, t, J=1.49 Hz), 5.38 (1H, s), 5.62 (1H, d t J=11.1 Hz, 1.35 Hz), 5.96 (1H, dt, J=11.1 Hz, 6.89 Hz), 7.22~7.41 (4H, m).

Example 6

Production of cis-N-(6,6-Dimethyl-2-hepten-4-ynyl)-N-methyl-(3-isopropenylbenzyl)amine Hydrochloride (Compound 6)

The procedure described in Example 3 was repeated, except that Compound 5 (0.65 g; 2.31 mmol) was used, to thereby yield 0.07 g of the target compound as white crystals (yield: 9.5%).

IR (KBr tablet, cm$^{-1}$); 3567, 3430, 2968, 2951, 2929, 2607, 2588, 1465, 1456; m. p. 101~109° C.; $^1$H-NMR (CDCl$_3$, ppm); 1.21 (9H, s), 2.18 (3H, s), 2.65 (3H, s), 3.71~3.88 (2H, m), 4.03~4.30 (2H, m), 5.17 (1H, s), 5.47 (1H, s), 5.99 (1H, d, J=9.45 Hz), 6.28 (1H, m) 7.42 (1H, t, J=8.10 Hz), 7.50~7.57 (2H, m), 7.71 (1H, s).

Referential Example 2

Production of 3-Bromobenzylbromide m-bromotoluene (25.33 g; 148.1 mmol), N-bromosuccinimide (26.36 g; 148.1 mmol), and benzoyl peroxide (0.3 g) were added to carbon tetrachloride (200 ml), and the mixture was heated under reflux for 3 hours. The white crystals that precipitated were filtered off, and the filtrate was concentrated under reduced pressure. The residue was taken up in n-hexane (200 ml), and the mixture was left to stand for 15 hours at room temperature. The white crystals that precipitated were filtered off, and the filtrate was concentrated, to thereby yield a yellow oily compound (25.1 g). The compound was analyzed by $^1$H-NMR and found to be a mixture of the target compound, the starting compound, and a dibromo compound (4.34:1.03:1.00). The yield based on the result of $^1$H-NMR analysis was 67.9%.

$^1$H-NMR (CDCl$_3$, ppm); 4.43 (2H, s), 7.12~7.54 (4H, m).

Referential Example 3

Production of N-(3-Bromobenzyl)methylamine

Triethylamine (19.2 g; 100.5 mmol) was dissolved in 40% solution of methylamine in methanol (150 ml). While the resultant solution was stirred in an ice bath, a solution of 3-bromobenzylbromide (25.1 g; 100.5 mmol) in methanol (40 ml) was added dropwise. After completion of the addition, the mixture was removed from the ice bath, and stirred for 15 hours at room temperature. Methanol and excess methylamine were evaporated under reduced pressure, and the residue was taken up in a mixture of ether and 2N hydrochloric acid (100 ml–100 ml). The aqueous layer was alkalinized with aqueous sodium hydroxide solution, and the mixture was extracted with chloroform (100 ml). The organic layer was washed with saturated aqueous sodium bicarbonate solution and with saturated brine, and dried over anhydrous sodium sulfate. The solvent was evaporated under reduced pressure, to thereby yield 12.7 g of the target compound as a yellow-orange oily substance (yield: 63.2%).

$^1$H-NMR (CDCl$_3$, ppm); 2.44 (3H, s), 3.72 (2H, s), 7.16~7.26 (2H, m), 7.38 (1H, m), 7.49 (1H, s).

Example 7

Production of trans-N-(6,6-Dimethyl-2-hepten-4-ynyl)-N-methyl-(3-bromobenzyl)amine (Compound 7)

N-(3-bromobenzyl)methylamine (2.00 g; 10.0 mmol) and sodium carbonate (1.51 g; 14.3 mmol) were added to N,N-dimethylformamide (20 ml). While the mixture was stirred at room temperature, 1-bromo-6,6-dimethyl-2-hepten-4-yne (1.92 g; 9.52 mmol) in N,N-dimethylformamide (10 ml) was added dropwise. The mixture was stirred for 1 hour at room temperature, and the reaction was stopped by pouring the mixture into ice/water, followed by extraction with ethyl acetate (100 ml). The organic layer was washed with saturated aqueous sodium bicarbonate solution and with saturated brine, and dried over anhydrous sodium sulfate. The solvent was evaporated under reduced pressure, and the residue was purified by silica gel column chromatography (n-hexane:ethyl acetate=20:1), to thereby yield 1.64 g of the target compound as yellow oily matter (yield: 53.8%).

$^1$H-NMR (CDCl$_3$, ppm); 1.22 (9H, s), 2.18 (3H, s), 3.04 (2H, dd, J=6.75 Hz, 1.35 Hz), 3.44 (2H, s), 5.64 (1H, d, J=15.9 Hz), 6.07 (1H, dt, J=15.9 Hz, 6.75 Hz), 7.14~7.43 (3H, m), 7.48 (1H, s).

Example 8

Production of trans-3-[N-(6,6-Dimethyl-2-hepten-4-ynyl)-N-methylaminomethyl]benzaldehyde (Compound 8)

Compound 7 (1.64 g: 5.12 mmol) was dissolved in tetrahydrofuran (20 ml), and the solution was cooled to −75° C. by use of a mixture of dry ice and acetone solvent under nitrogen atmosphere. n-butyl lithium in n-hexane (1.56 M:

3.3 ml; 5.12 mmol) was slowly added dropwise to the mixture, and the resultant mixture was stirred for 15 minutes. Subsequently, N,N-dimethylformamide (0.56 g; 7.68 mmol) was added dropwise to the mixture, and the resultant mixture was gradually brought to room temperature. Saturated aqueous ammonium chloride solution was added dropwise to the mixture, and the reaction was stopped, followed by extraction with ether (100 ml). The organic layer was washed with saturated aqueous sodium bicarbonate solution and with saturated brine, and dried over anhydrous sodium sulfate. The solvent was evaporated under reduced pressure, and the residue was purified by silica gel column chromatography (n-hexane:ethyl acetate=10:1), to thereby yield 1.06 g of the target compound (yield: 76.9%).

$^1$H-NMR (CDCl$_3$, ppm); 2.41 (9H, s), 2.19 (3H, s), 3.07 (2H, dd, J=6.48 Hz, 1.35 Hz), 3.55 (2H, s), 5.66 (1H, d t. J=15.9 Hz, 1.35 Hz), 6.09 (1H, dt, J=15.9 Hz, 6.48 Hz), 7.48 (1H, t, J=7.29 Hz), 7.61 (1H, d, J=7.29 Hz) 7.77 (1H, d, J=7.29 Hz), 7.83 (1H, s). 10.0 (1H, s).

Example 9

Production of trans-N-(6,6-Dimethyl-2-hepten-4-ynyl)-N-methyl-(3-vinylbenzyl)amine (Compound 9)

Methyl triphenylphosphonium bromide (0.99 g; 2.78 mmol) was added to benzene (20 ml). While the mixture was stirred under nitrogen atmosphere at room temperature, n-butyl lithium in n-hexane (1.56 M: 1.8 ml; 2.78 mmol) was added dropwise. The mixture was stirred for 10 minutes, and Compound 8 (0.50 g; 1.86 mmol) in benzene (20 ml) was added dropwise thereto, followed by stirring for 3 hours at room temperature. Reaction was stopped by pouring the mixture into ice/water, followed by extraction with benzene (100 ml). The organic layer was washed with saturated aqueous sodium bicarbonate solution and then with saturated brine, and dried over anhydrous sodium sulfate. The solvent was evaporated under reduced pressure, and the residue was purified by silica gel column chromatography (n-hexane:ethyl acetate=20:1), to thereby yield 0.21 g of the target compound as pale yellow oily matter (yield: 42.2%).

$^1$H-NMR (CDCl$_3$, ppm); 1.24 (9H, s), 2.19 (3H, s), 3.05 (2H, dd, J=6.62 Hz, 1.35 Hz), 3.48 (2H, s), 5.24 (1H, dd, J=10.8 Hz, 1.08 Hz), 5.65 (1H, dt, J=15.8 Hz, 1.35 Hz), 5.76 (1H, dd, J=17.8 Hz, 1.08 Hz), 6.10 (1H, dt, J=15.8 Hz, 6.62 Hz), 6.71 (1H, dd, J=10.8 Hz, 17.8 Hz), 7.19–7.35 (4H, m).

Example 10

Production of trans-N-(6,6-Dimethyl-2-hepten-4-ynyl)-N-methyl-(3-vinylbenzyl)amine Hydrochloride (Compound 10)

Compound 9 (0.21 g; 7.85×10$^{-1}$ mmol) was dissolved in diisopropyl ether (70 ml). While the solution was stirred at room temperature, 4N hydrochloric acid—ethyl acetate (0.20 ml; 8.0×10$^{-1}$ mmol) was added dropwise. The mixture was stirred for 3 hours, and crystals that precipitated were collected by filtration. The crystals were washed with diisopropyl ether, followed by drying in a desiccator under reduced pressure, to thereby yield 0.21 g of the target compound as white crystals (yield: 88.0%).

IR (KBr tablet, cm$^{-1}$); 3426, 2968, 2952, 2917, 2868, 2685, 2628, 2560, 2496, 1485, 1466, 1457, 1421, 1410, 1395, 1362, 1264; m. p. 149~150° C.; $^1$H-NMR (CDCl$_3$, ppm); 1.25 (9H, s), 2.64 (3H, d, J=3.51 Hz), 3.46~3.75 (2H, m), 4.01~4.26 (2H, m), 5.35 (1H, d, J=10.8 Hz), 5.82~5.91 (2H, m), 6.26 (1H, dt, J=15.7 Hz, 7.83 Hz), 6.73 (1H, dd, J=17.8 Hz, 10.8 Hz), 7.39~7.34 (3H, m), 7.69 (1H, s).

Example 11

Production of trans-N-(6,6-Dimethyl-2-hepten-4-ynyl)-N-methyl-[3-(2-methyl-1-propenyl)benzyl] amine (Compound 11)

Isopropyltriphenylphosphonium iodide (1.18 g; 2.73 mmol) was added to benzene (35 ml). While the mixture was stirred under nitrogen atmosphere at room temperature, n-butyl lithium in n-hexane (1.56 M: 1.8 ml; 2.73 mmol) was added dropwise. The mixture was stirred for 10 minutes, and Compound 8 (0.49 g; 1.82 mmol) in benzene (35 ml) was added dropwise thereto, followed by stirring for 3 hours at room temperature. Reaction was stopped by pouring the mixture into ice/water, followed by extraction with benzene (100 ml). The organic layer was washed with saturated aqueous sodium bicarbonate solution and with saturated brine, and dried over anhydrous sodium sulfate. The solvent was evaporated under reduced pressure, and the residue was purified by silica gel column chromatography (n-hexane:ethyl acetate=20:1), to thereby yield 0.13 g of the target compound as pale yellow oily matter (yield: 24.2%).

$^1$H-NMR (CDCl$_3$, ppm); 1.24 (9H, s), 1.86 (3H, s), 1.90 (3H, s), 2.19 (3H, s), 3.04 (2H, dd, J=6.75 Hz, 1.08 Hz), 3.47 (2H, s), 5.65 (1H, d, J=15.7 Hz), 6.09 (1H, dt, J=15.7 Hz, 6.75 Hz), 6.26 (1H, s), 7.11~7.28 (4H, m).

Example 12

Production of trans-N-(6,6-Dimethyl-2-hepten-4-ynyl)-N-methyl-[3-(2-methyl-1-propenyl)benzyl] amine Hydrochloride (Compound 12)

Compound 11 (0.13 g; 4.40×10$^{-1}$ mmol) was dissolved in diisopropyl ether (50 ml). While the solution was stirred at room temperature, 4N hydrochloric acid—ethyl acetate (0.11 ml; 4.40×10$^{-1}$ mmol) was added dropwise. The mixture was stirred for 3 hours, and crystals that precipitated were collected by filtration. The crystals were washed with diisopropyl ether, followed by drying in a desiccator under reduced pressure, to thereby yield 0.13 g of the target compound as white crystals (yield: 89.0%).

IR (KBr tablet, cm$^{-1}$); 3450, 2969, 2950, 2930, 2899, 2852, 2682, 2668, 2628, 2603, 2569, 2496, 1468, 1435, 1415, 975; m. p. 158~160° C.; $^1$H-NMR (CDCl$_3$, ppm); 1.25 (9H, s), 1.88 (3H, s), 1.92 (3H, d, J=1.08 Hz), 2.62 (3H, d, J=4.59 Hz), 3.46~3.76 (2H, m), 4.00~4.24 (2H, m), 5.83 (1H, d, J=15.9 Hz), 6.29 (1H, dt, J=15.9 Hz, 7.29 Hz), 7.26~7.47 (4H, m), 12.9 (1H, brs).

Referential Example 4

Production of 3'-(N-Cyclopropylaminomethyl) acetophenone

Cyclopropylamine (5.71 g; 10.0 mmol) and triethylamine (1.01 g; 10.0 mmol) were dissolved in methanol (50 ml). While the mixture was stirred in an ice bath, 3'-bromomethylacetophenone (2.13 g; 10.0 mmol) in methanol (10 ml) was added dropwise. The mixture was removed from the ice bath, and stirred for 18 hours at room temperature. The solvent was evaporated under reduced pressure, and the residue was taken up in 2N hydrochloric acid (100 ml), followed by extraction with diethyl ether (100 ml). The aqueous layer was alkalinized with aqueous sodium hydroxide solution, and the mixture was extracted with chloroform (100 ml). The organic layer was washed with saturated aqueous sodium bicarbonate solution and with saturated brine, and dried over anhydrous sodium sulfate. The solvent was evaporated under reduced pressure, and the residue was purified by silica gel column chromatography (n-hexane:ethyl acetate=5:1→0:1), to thereby yield 0.66 g of the target compound as yellow oily matter (yield: 34.9%).

$^1$H-NMR (CDCl$_3$, ppm); 0.34~0.49 (4H, m), 2.15 (1H, m), 2.61 (3H, s), 3.90 (2H, s), 7.42 (1H, t, J=7.70 Hz), 7.53 (1H, d, J=7.70 Hz), 7.84 (1H, dt, J=7.70 Hz, 1.49 Hz), 7.91 (1H, s).

Example 13

Production of trans-3'-[N-Cyclopropyl-N-(6,6-dimethyl-2-hepten-4-ynyl)aminomethyl] acetophenone (Compound 13)

3'-(N-cyclopropylaminomethyl)acetophenone (0.35 g; 1.85 mmol) and potassium carbonate (0.36 g; 2.64 mmol) were added to N,N-dimethylformamide (15 ml). While the mixture was stirred in an ice bath, 1-bromo-6,6-dimethyl-2-hepten-4-yn (0.35 g; 1.76 mmol) in N,N-dimethylformamide (5 ml) was added dropwise. After completion of the addition, the mixture was removed from the ice bath, and stirred for 18 hours at room temperature. The mixture was poured into ice+saturated aqueous sodium bicarbonate solution, followed by extraction with ethyl acetate (100 ml). The organic layer was washed with saturated aqueous sodium bicarbonate solution and with saturated brine, and dried over anhydrous sodium sulfate. The solvent was evaporated under reduced pressure, and the residue was purified by silica gel column chromatography (n-hexane:ethyl acetate=10:1), to thereby yield 0.33 g of the target compound (yield: 60.6%).

$^1$H-NMR (CDCl$_3$, ppm); 0.33~0.48 (4H, m), 1.25 (9H, s), 1.87 (1H, ), 2.61 (3H, s), 3.17 (2H, dd, J=6.74 Hz, 1.49 Hz), 3.78 (2H, s), 5.58 (1H, d, J=15.7 Hz), 6.12 (1H, dt, J=15.7 Hz, 6.74 Hz), 7.36 (1H, t, J=7.83 Hz), 7.49 (1H, d, J=7.83 Hz), 7.82~7.85 (2H, m).

Example 14

Production of trans-N-Cyclopropyl-N-(6,6-dimethyl-2-hepten-4-ynyl)-(3-isopropenylbenzyl) amine (Compound 14)

The procedure described in Example 9 was repeated, except that methyl triphenylphosphonium bromide (0.57 g; 1.61 mmol), n-butyl lithium in n-hexane (1.56 M: 1.0 ml; 1.61 mmol), and Compound 13 (0.33 g; 1.07 mmol) were used, to thereby yield 0.15 g of the target compound (yield: 45.6%).

$^1$H-NMR (CDCl$_3$, ppm); 036~0.49 (4H, m), 1.25 (9H, s), 1.86 (1H, m), 2.15 (3H, s), 3.18 (2H, dd, J=6.89 Hz, 1.49 Hz), 3.74 (2H, s), 5.07 (1H, t, J=1.76 Hz), 5.36 (1H, s), 5.58 (1H, d, J=15.7 Hz), 6.14 (1H, dt, J=15.7 Hz, 6.89 Hz), 7.35~7.16 (4H, m).

Example 15

Production of trans-N-Cyclopropyl-N-(6,6-dimethyl-2-hepten-4-ynyl)-(3-isopropenylbenzyl) amine Hydrochloride (Compound 15)

The procedure described in Example 12 was repeated, except that diisopropyl ether (50 ml), Compound 14 (0.15 g; 4.88×10$^{-1}$ mmol), and 4N hydrochloric acid—ethyl acetate (0.12 ml; 4.88×10$^{-1}$ mmol) were used, to thereby yield 0.09 g of the target compound as white crystals (yield: 53.6%).

IR (KBr tablet, cm$^{-1}$); 2970, 2951, 2926, 2649, 2630, 2534, 2496, 1039, 997, 884, 806; m. p. 115.5~117.0° C.; $^1$H-NMR (CDCl$_3$, ppm); 0.78~0.98 (4H, m), 1.26 (9H, s), 2.18 (3H, s), 2.27 (1H, m), 3.63~3.72 (2H, m), 4.24 (3H, d, J=7.29 Hz), 5.17 (1H, d, J=1.62 Hz), 5.45 (1H, s), 5.84 (1H, d, J=15.9 Hz), 6.32 (1H, dt, J=15.9 Hz, 7.83 Hz), 7.33~7.57 (3H, m), 7.69 (1H, s), 12.6 (1H, brs).

Referential Example 5

Production of 3-Bromo-5-methylbenzyl Bromide

5-Bromo-m-xylene (10.0 g; 54.0 mmol), N-bromosuccinimide (9.63 g; 54.0 mmol), and benzoyl peroxide (150 mg) were added to benzene (100 ml), and the mixture was heated under reflux for 2.5 hours. The resultant mixture was left to cool to room temperature, and insoluble matter was filtered off, followed by washing with benzene. The filtrate was evaporated under reduced pressure, and the residue was taken up in n-hexane. The mixture was left to stand for 30 minutes, and dried over magnesium sulfate. The solvent was evaporated under reduced pressure, and the residue was purified by silica gel column chromatography (n-hexane:ethyl acetate=1:0→20:1), to thereby yield 9.44 g of the target compound (yield: 66.3%).

$^1$H-NMR (CDCl$_3$, ppm); 2.31 (3H, s), 4.39 (2H, s), 7.12 (1H, s), 7.26 (1H, s), 7.34 (1H, s).

Referential Example 6

Production of N-(3-Bromo-5-methylbenzyl) methylamine

Triethylamine (3.62 g; 35.8 mmol) was dissolved in 40% solution of methylamine in methanol (100 ml). While the solution was stirred in an ice bath, 3-bromo-5-methylbenzyl bromide (9.44 g; 35.8 mmol) in chloroform/methanol (25 ml/25 ml) was added dropwise. After completion of the addition, the mixture was stirred for 72 hours at room temperature. Subsequently, the solvent was evaporated under reduced pressure, and the residue was taken up in 2N hydrochloric acid (100 ml), followed by washing with ether (100 ml). The aqueous layer was alkalinized with aqueous sodium hydroxide solution, and the mixture was extracted with chloroform (100 ml). The organic layer was washed with saturated aqueous sodium bicarbonate solution and with saturated brine, and dried over sodium sulfate. The solvent was evaporated under reduced pressure, and the residue was purified by silica gel column chromatography (chloroform:methanol=1:08→10:1), to thereby yield 5.58 g of the target compound as pale yellow oily matter (yield: 72.8%).

$^1$H-NMR (CDCl$_3$, ppm); 2.32 (3H, s), 2.44 (3H, s), 3.68 (2H, s), 7.06 (1H, s), 7.22 (1H, s), 7.26 (1H, s),

Example 16

Production of trans-N-(6,6-Dimethyl-2-hepten-4-ynyl)-N-methyl-(3-bromo-5-methylbenzyl)amine (Compound 16)

N-(3-bromo-5-methylbenzyl)methylamine (2.68 g; 12.5 mmol) and sodium carbonate (1.89 g; 17.9 mmol) were added to N,N-dimethylformamide (20 ml). While the mixture was stirred at room temperature, 1-bromo-6,6-dimethyl-2-hepten-4-yne (2.40 g; 11.9 mmol) in N,N-dimethylformamide (15 ml) was added dropwise. The mixture was stirred at room temperature for 1.5 hours, and reaction was stopped by pouring the mixture into ice+ saturated aqueous sodium bicarbonate solution, followed by extraction with ethyl acetate (100 ml). The organic layer was washed with saturated aqueous sodium bicarbonate solution and with saturated brine, and dried over sodium sulfate. The solvent was evaporated under reduced pressure, and the residue was purified by silica gel column chromatography (n-hexane:ethyl acetate=15:1), to thereby yield 2.24 g of the target compound (yield: 56.3%).

$^1$H-NMR (CDCl$_3$, ppm); 1.22 (9H, s), 2.17 (3H, s), 2.31 (3H, s), 3.04 (1H, dd, J=6.48 Hz, 1.35 Hz), 3.40 (2H, s), 5.64 (1H, d, J=15.9 Hz), 6.07 (1H, dt, J=15.9 Hz, 6.48 Hz), 7.04 (1H, s), 7.20 (1H, s), 7.26 (1H, s).

Example 17

Production of trans-2-[3-{N-(6,6-Dimethyl-2-hepten-4-ynyl)-N-methylaminomethyl}-5-methylphenyl]-2-propanol (Compound 17)

Compound 16 (2.24 g; 6.70 mmol) was dissolved in tetrahydrofuran (25 ml), and the solution was cooled to −78° C. under nitrogen atmosphere. n-butyl lithium in n-hexane (1.56 M: 4.3 ml; 6.70 mmol) was added dropwise to the resultant mixture, and stirred for 15 minutes. Acetone (3 ml) was added dropwise to the mixture, and brought to room temperature over 3 hours, followed by stirring for 1 hour at room temperature. Reaction was stopped by dropwise addition of saturated aqueous ammonium chloride solution, followed by extraction with diethyl ether (50 ml). The organic layer was washed with saturated brine, and dried over sodium sulfate. The solvent was evaporated under reduced pressure, and the residue was purified by silica gel column chromatography (n-hexane:ethyl acetate=5:1), to thereby yield 1.13 g of the target compound (yield: 53.8%).

$^1$H-NMR (CDCl$_3$, ppm); 1.24 (9H, s), 1.57 (6H, s), 2.19 (3H, s), 2.35 (3H, s), 3.04 (2H, dd, J=6.35 Hz 1.49 Hz), 3.46 (2H, s), 5.64 (1H, dt, J=15.9 Hz, 1.49 Hz), 6.09 (1H, dt, J=15.9 Hz, 6.35 Hz), 7.03 (1H, s), 7.18 (1H, s), 7.20 (1H, s).

Example 18

Production of trans-N-(6,6-Dimethyl-2-hepten-4-ynyl)-N-methyl-(3-isopropenyl-5-methylbenzyl) amine (Compound 18)

Compound 17 (1.08 g; 3.45 mmol) was dissolved in pyridine (50 ml). While the solution was stirred at room temperature, phosphorus oxychloride (5.28 g; 34.5 mmol) was added dropwise. The mixture was heated for 2.5 hours at 100° C. while being stirred, and left to cool to room temperature. The mixture was poured into ice+saturated aqueous sodium bicarbonate solution, followed by extraction with chloroform (100 ml). The organic layer was washed with saturated aqueous sodium bicarbonate solution (100 ml×2) and with saturated brine (×1), and dried over sodium sulfate. The solvent was evaporated under reduced pressure, and the residue was purified by silica gel column chromatography (n-hexane:ethyl acetate=10:1), to thereby yield 0.53 g of the target compound (yield: 52.0%).

$^1$H-NMR (CDCl$_3$, ppm); 1.24 (9H, s), 2.14 (3H, s), 2.19 (3H, s), 2.35 (3H, s), 3.05 (2H, dd, J=6.35 Hz, 1.49 Hz), 3.45 (2H, s), 5.05 (1H, t, J=1.49 Hz), 5.35 (1H, s), 5.64 (1H, dt, J=15.9 Hz, 1.49 Hz), 6.10 (1H, dt, J=15.9 Hz, 6.35 Hz), 7.03 (1H, s), 7.16 (1H, s), 7.19 (1H, s).

Example 19

Production of trans-N-(6,6-Dimethyl-2-hepten-4-ynyl)-N-methyl-(3-isopropenyl-5-methylbenzyl) amine Hydrochloride (Compound 19)

Compound 18 (0.53 g; 1.79 mmol) was dissolved in diisopropyl ether (100 ml). While the solution was stirred at room temperature, hydrogen chloride in ethyl acetate (4 N: 0.45 ml; 1.79 mmol) was added dropwise. The mixture was stirred for 15 hours at room temperature, and white crystals that precipitated were collected by filtration. The crystals were washed, and dried in a desiccator, to thereby yield 0.47 g of the target compound as white crystals (yield: 79.1%).

IR (KBr tablet, cm$^{-1}$); 3450, 2972, 2958, 2916, 2672, 2629, 1469, 1457, 977, 913, 895; m. p. 173.5~175.5° C.; $^1$H-NMR (CDCl$_3$, ppm); 1.25 (9H, s), 2.40 (3H, s), 2.63 (3H, d, J=5.13 Hz), 3.46~3.76 (2H, m), 3.96~4.22 (2H, m), 5.14 (1H, t, J=1.49 Hz), 5.44 (1H, s), 5.83 (1H, d, J=15.7 Hz), 6.29 (1H, dt, J=15.7 Hz, 7.29 Hz), 7.33 (1H, s), 7.34 (1H, s), 7.65 (1H, s), 12.9 (1H, brs).

Example 20

Production of trans-2-[3-{N-(6,6-Dimethyl-2-hepten-4-ynyl)-N-methylaminomethyl}phenyl]-3-methyl-2-butanol (Compound 20)

Compound 7 (1.59 g; 4.96 mmol) was dissolved in tetrahydrofuran (25 ml). While the solution was stirred at −75° C. under nitrogen atmosphere, n-butyl lithium in n-hexane (1.56 M: 3.2 ml; 4.99 mmol) was added dropwise. The mixture was stirred for 10 minutes, and 3-methyl-2-butanone (2.00 g) in tetrahydrofuran (5 ml) was added dropwise thereto. The mixture was brought to room temperature over 2.5 hours, and saturated aqueous ammonium chloride solution was added dropwise thereto. Water (100 ml) was added to the mixture, followed by extraction with diethyl ether (100 ml). The organic layer was washed with saturated brine, and dried over sodium sulfate. The solvent was evaporated under reduced pressure, and the residue was purified by silica gel column chromatography (n-hexane:ethyl acetate=10:1→5:1), to thereby yield 0.76 g of the target compound as yellow oily matter (yield: 47.2%).

$^1$H-NMR (CDCl$_3$, ppm); 0.80 (3H, d, J=6.75 Hz), 0.89 (3H, d, J=6.75 Hz), 1.24 (9H, s), 1.53 (3H, s), 2.08 (1H, m), 2.18 (3H, s), 3.03 (2H, dd, J=6.62 Hz, 1.08 Hz), 3.50 (2H, s), 5.64 (1H, d, J=15.9 Hz), 6.09 (1H, dt, J=15.9 Hz, 6.62 Hz), 7.17~7.35 (4H, m).

Example 21

Production of trans-N-(6,6-Dimethyl-2-hepten-4-ynyl)-N-methyl-[3-(1-isopropylvinyl)benzyl]amine (Compound 21)

Compound 20 (0.76 g; 2.32 mmol) was dissolved in pyridine (35 ml). While the solution was stirred at room temperature, phosphorus oxychloride (3.71 g; 24.2 mmol) was added dropwise. The mixture was heated for 3 hours at 100° C. while being stirred, and brought to room temperature. The mixture was poured into ice+saturated aqueous sodium bicarbonate solution, followed by extraction with chloroform (100 ml). The organic layer was washed with saturated aqueous sodium bicarbonate solution and then with saturated brine, and dried over sodium sulfate. The solvent was evaporated under reduced pressure, and the residue was purified by silica gel column chromatography (n-hexane:ethyl acetate=10:1), to thereby yield 0.41 g of the target compound (yield: 56.9%).

$^1$H-NMR (CDCl$_3$, ppm); 1.09 (3H×2, d, J=7.02 Hz), 1.20 (9H, s), 2.84 (1H, m), 3.04 (2H, d, J=6.48 Hz), 3.49 (2H, s), 5.02 (1H, s), 5.14 (1H, s), 5.65 (1H, d, J=15.7 Hz), 6.09 (1H, dt, J=15.7Hz, 6.48 Hz), 7.19~7.28 (4H, m).

Example 22

Production of trans-N-(6,6-Dimethyl-2-hepten-4-ynyl)-N-methyl-[3-(1-isopropylvinyl)benzyl]amine Hydrochloride (Compound 22)

Compound 21 (0.41 g; 1.32 mmol) was dissolved in diisopropyl ether (100 ml). While the solution was stirred at room temperature, hydrogen chloride in ethyl acetate (4 N: 0.33 ml; 1.32 mmol) was added dropwise. The mixture was stirred for 15 hours at room temperature, and white crystals that precipitated were collected by filtration. The crystals were washed, and dried in a desiccator, to thereby yield 0.35 g of the target compound as white crystals (yield: 76.6%).

IR (KBr tablet, cm$^{-1}$); 2968, 2929, 2899, 2871, 2668, 2614, 2596, 2539, 2492, 1464, 963; m. p. 160~162° C.; $^1$H-NMR (CDCl$_3$, ppm); 1.08~1.11 (3H×2, m), 1.25 (9H, s), 2.63 (3H, d, J=4.86 Hz), 2.86 (1H, m), 3.46~3.76 (2H, m), 4.00~4.26 (2H, m), 5.11 (1H, s), 5.22 (1H, s), 5.83 (1H, d, J=14.9 Hz), 6.29 (1H, dt, J=14.9 Hz, 7.29 Hz), 7.41~7.56 (4H, m), 13.0 (1H, brs), Referential Example 7

Production of 3'-Methylpropiophenone

Magnesium turnings (1.00 g; 41.2 mmol) and iodine (two or three granules) were added to anhydrous diethyl ether (10 ml). While the mixture was stirred and heated under nitrogen atmosphere, m-bromotoluene (7.04 g; 41.2 mmol) in anhydrous diethyl ether (20 ml) was slowly added dropwise. The heating was ceased when spontaneous reflux started. After completion of the reflux, the mixture was brought to room temperature, and propionitrile (1.89 g; 34.3 mmol) in anhydrous diethyl ether (20 ml) was added dropwise. After completion of spontaneous reflux, the mixture was left to cool to room temperature. While the mixture was cooled in an ice bath, water and cooled diluted sulfuric acid were added dropwise in a sequential manner, followed by extraction with diethyl ether (100 ml). The organic layer was washed with saturated aqueous sodium bicarbonate solution and then with saturated brine, and dried over sodium sulfate. The solvent was evaporated under reduced pressure, and the residue was purified by silica gel column chromatography (n-hexane:ethyl acetate=10:1), to thereby yield 2.38 g of the target compound as pale yellow oily matter (yield: 46.8%).

$^1$H-NMR (CDCl$_3$, ppm); 1.22 (3H, t, J=1.89 Hz), 2.42 (3H, s), 3.00 (2H, q, J=1.89 Hz), 7.34~7.36 (2H, m), 7.75~7.78 (2H, m).

Referential Example 8

Production of 3'-Bromomethylpropiophenone

3'-Methylpropiophenone (2.38 g; 16.1 mmol), N-bromosuccinimide (2.78 g; 16.1 mmol), and benzoyl peroxide (0.20 g) were added to carbon tetrachloride (60 ml), and the mixture was heated under reflux for 3 hours. The mixture was brought to room temperature, and insoluble matter was filtered off. The solvent was concentrated under reduced pressure, and the residue was purified by silica gel column chromatography (n-hexane:ethyl acetate=20:1), to thereby yield 3.48 g of the target compound as pale yellow oily, matter (yield: 95.2%). $^1$H-NMR (CDCl$_3$, ppm); 1.23 (3H, t, J=1.89 Hz), 3.01 (2H, q, J=1.89 Hz), 4.53 (3H, s), 7.42~7.70 (2H, m), 7.79~8.13 (2H, m).

Example 23

Production of trans-3'-[N-(6,6-Dimethyl-2-hepten-4-ynyl)-N-methylaminomethyl]propiophenone (Compound 23)

N-(6,6-dimethyl-2-hepten-4-ynyl)methylamine (trans:cis=about 3:1) (0.80 g; 5.29 mmol) and sodium carbonate (0.80 g; 7.56 mmol) were added to N,N-dimethylformamide (20 ml). While the mixture was stirred at room temperature, 3'-bromomethylpropiophenone (1.14 g; 5.04 mmol) in N,N-dimethylformamide (10 ml) was added dropwise. The mixture was stirred for 2.5 hours at room temperature, and poured into ice+saturated aqueous sodium bicarbonate solution, followed by extraction with ethyl acetate (100 ml). The organic layer was washed with saturated aqueous sodium bicarbonate solution and then with saturated brine, and dried over anhydrous sodium sulfate. The solvent was evaporated under reduced pressure, and the residue was purified by silica gel column chromatography (n-hexane:ethyl acetate=10:1), to thereby yield 0.40 g of the target compound as orange oily matter (yield: 26.7%).

$^1$H-NMR (CDCl$_3$, ppm); 1.19~1.24 (9H, m), 2.19 (3H, s), 2.93~3.07 (5H, m), 3.54 (2H, s), 5.66 (1H, d, J=15.7 Hz), 6.09 (1H, dt, J=15.7 Hz, 6.48 Hz), 7.40 (1H, t, J=7.56 Hz), 7.52 (1H, d, J=7.56 Hz), 7.84 (1H, d, J=7.56 Hz), 7.90 (1H, s).

Example 24

Production of trans-N-(6,6-Dimethyl-2-hepten-4-ynyl)-N-methyl-[3-(1-ethylvinyl)benzyl]amine (Compound 24)

Methyl triphenylphosphonium bromide (0.72 g; 2.01 mmol) was added to benzene (15 ml). While the mixture was stirred under nitrogen atmosphere at room temperature, n-butyl lithium in n-hexane (1.56 M: 1.3 ml; 2.03 mmol) was added dropwise. The mixture was stirred for 5 minutes, and Compound 23 (0.40 g; 1.34 mmol) in benzene (5 ml) was added dropwise thereto, followed by heating under reflux for 2 hours. The mixture was brought to room temperature, and poured into ice/water, followed by extraction with benzene (100 ml). The organic layer was washed with saturated brine, and dried over anhydrous sodium sulfate. The solvent was evaporated under reduced pressure, and the residue was purified by silica gel column chromatography (n-hexane:ethyl acetate=20:1), to thereby yield 0.20 g of the target compound as pale yellow oily matter (yield: 50.5%).

$^1$H-NMR (CDCl$_3$, ppm); 1.10 (2H, t, J=1.89 Hz), 1.22 (9H, s), 2.19 (3H, s), 2.52 (3H, q), 3.05 (2H, dd, J=6.62 Hz, 1.35 Hz), 3.49 (1H, s), 5.05 (1H, d, J=1.62 Hz), 5.28 (1H, s), 5.67 (1H, d, J=15.9 Hz), 6.09 (1H, dt, J=15.9 Hz, 6.62 Hz), 7.19~7.32 (4H, m).

Example 25

Production of trans-N-(6,6-Dimethyl-2-hepten-4-ynyl)-N-methyl-[3-(1-ethylvinyl)benzyl]amine Hydrochloride (Compound 25)

Compound 24 (0.20 g; 6.77×10$^{-1}$ mmol) was dissolved in diisopropyl ether (100 ml). While the solution was stirred at room temperature, hydrogen chloride in ethyl acetate (4 N: 0.20 ml; 8.00×10$^{-1}$ mmol) was added dropwise. The mixture was stirred for 6 hours, and diisopropyl ether (100 ml) was added, followed by stirring for an additional 30 minutes. White crystals that precipitated were collected by filtration. The crystals were washed with diisopropyl ether, and dried in a desiccator, to thereby yield 0.17 g of the target compound (yield: 75.6%).

IR (KBr tablet, cm$^{-1}$); 3449, 2968, 2929, 2919, 2618, 2590, 2552; m.p 158~160° C.; $^1$H-NMR (CDCl$_3$, ppm); 1.11 (2H, t, J=7.29 Hz), 1.25 (9H, s), 2.54 (3H, q, J=7.29 Hz), 2.63 (3H, d, J=3.51 Hz), 3.52~3.71 (2H, m), 4.02~4.26 (2H, m), 5.14 (1H, s), 5.37 (1H, s), 5.83 (1H, d, J=15.7 Hz), 6.28

(1H, dt, J=15.7 Hz, 7.29 Hz), 7.34~7.52 (3H, m), 7.65 (1H, s), 13.0 (1H, brs),

Example 26

Production of trans-, cis-N-(6,6-Dimethyl-2-hepten-4-ynyl)-N-methyl-[3-(1-methyl-1-propenyl)benzyl] amine (Compound 26)

Ethyl triphenylphosphonium bromide (0.98 g; 2.65 mmol) was added to benzene (15 ml). While the mixture was stirred under nitrogen atmosphere at room temperature, n-butyl lithium in n-hexane (1.56 M: 1.70 ml; 2.65 mmol) was added dropwise. The mixture was stirred for 5 minutes, and Compound 1 (0.50 g; 1.76 mmol) in benzene (5 ml) was added dropwise thereto, followed by heating under reflux for 3 hours. Subsequently, the mixture was left to cool to room temperature, and reaction was stopped by pouring the mixture into ice/water, followed by extraction with benzene (100 ml). The organic layer was washed with saturated brine, and dried over anhydrous sodium sulfate. The solvent was evaporated under reduced pressure, and the residue was purified by silica gel column chromatography (n-hexane:ethyl acetate=20:1), to thereby yield 0.13 g of the target compound (yield: 25.0%).

$^1$H-NMR (CDCl$_3$, ppm); 1.24 (9H, s), 1.59 (3H, dd, J=6.89 Hz, 1.49 Hz), 2.02 (3H, t, J=1.49 Hz), 2.20 (3H, s), 3.05 (2H, dd, J=6.35 Hz, 1.49 Hz), 3.49 (2H, s), 5.55 (1H, m), 5.65 (1H, d, J=15.4 Hz), 6.09 (1H, dt, J=15.4 Hz, 6.35 Hz), 7.06~7.31 (4H, m).

Example 27

Production of trans-, cis-N-(6,6-Dimethyl-2-hepten-4-ynyl)-N-methyl-[3-(1-methyl-1-propenyl)benzyl] amine Hydrochloride (Compound 27)

Compound 26 (0.13 g; 4.40×10$^{-1}$ mmol) was dissolved in diisopropyl ether (50 ml). While the solution was stirred at room temperature, hydrogen chloride in ethyl acetate (4 N: 0.11 ml; 4.40×10$^{-1}$ mmol) was added dropwise. The mixture was stirred for 60 hours, and the solvent was evaporated under reduced pressure. The residue was taken up in diisopropyl ether (70 ml), and the mixture was stirred for an additional 3 hours. White crystals that precipitated were collected by filtration. The crystals were washed with diisopropyl ether, and dried in a desiccator under reduced pressure, to thereby yield 0.11 g of the target compound as white crystals (yield: 75.3%).

IR (KBr tablet, cm$^{-1}$); 3428, 2967, 2936, 2918, 2664, 2618, 2596, 2562, 2497, 970; m. p. 152~156° C.; $^1$H-NMR (CDCl$_3$, ppm); 1.25 (9H, s), 1.59 (3H, s), 2.04 (3H, s), 2.64 (3H, s), 3.53~3.69 (2H, m), 4.03~4.25 (2H, m), 5.61 (1H, m), 5.84 (1H, d, J=15.4 Hz), 6.29 (1H, dt, J=15.4 Hz, 7.56 Hz), 7.30~7.56 (4H, m), 13.0 (1H, brs).

Referential Example 9

Production of 3-Bromo-4-fluorobenzylbromide

3-Bromo-4-fluorotoluene (9.36 g; 49.5 mmol) was dissolved in carbon tetrachloride (100 ml), and N-bromosuccinimide (8.82 g; 49.6 mmol) and benzoyl peroxide (200 mg) were added thereto. The mixture was heated under reflux for 1 hour, and then cooled. Insoluble matter was filtered off, followed by washing with carbon tetrachloride. The filtrate was concentrated under reduced pressure, and n-hexane (120 ml) was added thereto. The mixture was left to stand, and insoluble matter was filtered off, followed by washing with n-hexane. The filtrate was evaporated, to thereby yield 13.04 g of a mixture of the target-compound, the starting compound, and the dibromo compound (yield based on the weight of the mixture: 98.2%).

$^1$H-NMR (CDCl$_3$, ppm); 4.42 (2H, s), 7.09 (1H, t, J=8.37 Hz), 7.30 (1H, m), 7.60 (1H, dd, J=6.46 Hz, 1.89 Hz), Referential Example 10

Production of N-(3-Bromo-4-fluorobenzyl) methylamine

To 40% solution of methylamine in methanol (100 ml) with being stirred under ice cooling was added dropwise 3-bromo-4-fluorobenzylbromide (13.04 g; 48.7 mmol) in methanol (10 ml). The mixture was brought to room temperature, and stirred for 91 hours. The reaction mixture was concentrated under reduced pressure, and the residue was taken up in water. The mixture was alkalinized with sodium hydroxide, followed by extraction with ether (160 ml). The organic layer was dried over magnesium sulfate, and the solvent was evaporated under reduced pressure. The residue was purified by silica gel column chromatography (chloroform:methanol=1:0→10:1), to thereby yield 6.25 g of the target compound (yield: 58.9%).

$^1$H-NMR (CDCl$_3$, ppm); 2.44 (3H, s), 3.70 (2H, s), 7.06 (1H, t, J=8.37 Hz), 7.22 (1H, m), 7.53 (1H, dd, J=6.48 Hz, 1.89 Hz), Example 28

Production of trans-N-(6,6-Dimethyl-2-hepten-4-ynyl)-N-methyl-(3-bromo-4-fluorobenzyl)amine (Compound 28)

N-(3-bromo-4-fluorobenzyl)methylamine (4.00 g; 18.3 mmol) and sodium carbonate (2.78 g; 26.3 mmol) were added to N,N-dimethylformamide (35 ml). While the mixture was stirred at room temperature, 1-bromo-6,6-dimethyl-2-hepten-4-yne (3.51 g; 17.5 mmol) in N,N-dimethylformamide (15 ml) was added dropwise. The mixture was stirred for 4 hours at room temperature, and the mixture was poured into ice+saturated aqueous sodium bicarbonate solution, followed by extraction with ethyl acetate (100 ml). The organic layer was washed with saturated aqueous sodium bicarbonate solution and then with saturated brine, and dried over anhydrous sodium sulfate. The solvent was evaporated under reduced pressure, and the residue was purified by silica gel column chromatography (n-hexane:ethyl acetate=10:1), to thereby yield 2.54 g of the target compound as orange oily matter (yield: 42.9%).

$^1$H-NMR (CDCl$_3$, ppm); 1.24 (9H, s), 2.16 (3H, s), 3.04 (2H, d, J=6.48 Hz), 3.42 (2H, s), 5.64 (1H, d, J=15.9 Hz), 6.06 (1H, dt, J=15.9 Hz, 6.48 Hz), 7.05 (1H, t, J=8.37 Hz), 7.21 (1H, m), 7.52 (1H, dd, J=6.89 Hz, 1.89 Hz).

Example 29

Production of trans-2-[2-Fluoro-5-{N-(6,6-dimethyl-2-hepten-4-ynyl)-N-methylaminomethyl}phenyl-2-propanol (Compound 29)

Compound 28 (1.00 g; 2.96 mmol) was dissolved in tetrahydrofuran (15 ml). While the solution was stirred at −78° C. under nitrogen atmosphere, n-butyl lithium in n-hexane (1.63 M: 1.8 ml; 2.97 mmol) was added dropwise. The mixture was stirred for 10 minutes, and acetone (2 ml) was added dropwise thereto. The mixture was gradually brought to room temperature, and saturated aqueous ammonium chloride solution was added dropwise thereto, followed by extraction with diethyl ether (100 ml). The organic layer was washed with saturated brine, and dried over sodium sulfate. The solvent was evaporated under reduced pressure, and the residue was purified by silica gel column chromatography (n-hexane:ethyl acetate=5:1→3:1), to thereby yield 0.55 g of the target compound as yellow oily matter (yield: 58.5%).

$^1$H-NMR (CDCl$_3$, ppm); 1.24 (9H, s), 1.64 (3H×2, s), 2.17 (3H, s), 3.03 (2H, dd, J=6.48 Hz, 1.35 Hz), 3.44 (2H, s), 5.64 (1H, d, J=15.7 Hz), 6.07 (1H, dt, J=15.7 Hz, 6.48 Hz), 6.96 (1H, dd, J=11.9 Hz, 8.37 Hz), 7.17 (1H, m), 7.46 (1H, dd, J=8.37 Hz, 2.16 Hz).

Example 30

Production of trans-N-(6,6-Dimethyl-2-hepten-4-ynyl)-N-methyl-(4-fluoro-3-isopropenylbenzyl)amine (Compound 30)

Compound 29 (0.55 g; 1.73 mmol) and phosphorus oxychloride (1.33 g; 8.65 mmol) were dissolved in pyridine (25 ml). The solution was stirred for 3 hours at 110° C., and left to cool to room temperature. The mixture was poured into ice+saturated aqueous sodium bicarbonate solution, followed by extraction with diethyl ether (100 ml). The organic layer was washed with saturated aqueous sodium bicarbonate solution and then with saturated brine, and dried over sodium sulfate. The solvent was evaporated under reduced pressure, and the residue was purified by silica gel column chromatography (n-hexane:ethyl acetate=10:1), to thereby yield 0.17 g of the target compound (yield: 32.8%).

$^1$H-NMR (CDCl$_3$, ppm); 1.24 (9H, s), 2.14 (3H, s), 2.18 (3H, s), 3.04 (2H, dd, J=6.48 Hz, 1.35 Hz), 3.44 (2H, s), 5.23 (1H×2, s), 5.64 (1H, d, J=15.9 Hz), 6.07 (1H, dt, J=15.9 Hz, 6.48 Hz), 6.97 (1H, dd, J=10.8 Hz, 8.10 Hz), 7.14~7.24 (2H, m).

Example 31

Production of trans-N-(6,6-Dimethyl-2-hepten-4-ynyl)-N-methyl-(4-fluoro-3-isopropenylbenzyl)amine Hydrochloride (Compound 31)

Compound 30 (0.17 g; 5.68×10$^{-1}$ mmol) was dissolved in diisopropyl ether (100 ml). While the solution was stirred at room temperature, hydrogen chloride in ethyl acetate (4 N: 0.15 ml; 6.00×10$^{-1}$ mmol) was added dropwise. The mixture was stirred overnight, and white crystals that precipitated were collected by filtration. The crystals were washed with diisopropyl ether, and dried in a desiccator under reduced pressure, to thereby yield 0.16 g of the target compound as white crystals (yield: 83.9%).

IR (KBr tablet, cm$^{-1}$); 3438, 2973, 2924, 2691, 2677, 2633, 1496, 1225, 2497, 970; m. p. 184~186° C.; $^1$H-NMR (CDCl$_3$, ppm); 1.25 (9H, s), 2.17 (3H, s), 2.63 (3H, d, J=4.32 Hz), 3.52~3.71 (2H, m), 3.96~4.24 (2H, m), 5.81 (1H, s), 5.84 (1H, d, J=15.7 Hz), 5.87 (1H, s), 6.26 (1H, dt, J=15.7 Hz, 7.25 Hz), 7.13 (1H, m), 7.55~7.60 (2H, m).

Referential Example 11

Production of N-(5-Bromo-2-methylbenzyl)methylamine 1,4-(Bischloromethoxy)butane (9.35 g; 50 mmol) and tin tetrachloride (anhydrous)(13.03 g; 50 mmol) were added to p-bromotoluene (42.76 g; 250 mmol). The mixture was stirred for 2.5 hours at 45 to 58° C., and then cooled. Water was added to the reaction mixture, followed by extraction with chloroform (80 ml×2). The combined organic layer was washed with saturated brine, and dried over magnesium sulfate. The solvent was evaporated under reduced pressure, and excess p-bromotoluene was removed by vacuum distillation. The residue was purified by silica gel column chromatography (n-hexane:ethyl acetate=20:1). The purified product was taken up in 40% solution of methylamine in methanol (100 ml), and the mixture was stirred for 72 hours at room temperature. Methanol was removed from the mixture, and water was added thereto. The mixture was alkalinized with sodium hydroxide pellet, and extracted with ether (150 ml), followed by drying over magnesium sulfate. The solvent was evaporated under reduced pressure, and the residue was purified by silica gel column chromatography (chloroform→chloroform:methanol=30:1). The purified product was dissolved in dioxane (100 ml), and di-tert-butyldicarbonate (10.5 g) was added thereto, followed by stirring for 16 hours at room temperature. The reaction mixture was concentrated under reduced pressure, and the residue was chromatographed on a silica gel column (n-hexane:ethyl acetate=15:1), to thereby remove 2-bromo-5-methylbenzyl derivative. The purified 5-bromo-2-methylbenzyl derivative was taken up in 4N hydrochloric acid—ethyl acetate (50 ml), and the mixture was stirred for 30 minutes at room temperature. Subsequently, ethyl acetate was evaporated under reduced pressure, and water was added thereto, followed by alkalinization with aqueous sodium hydroxide solution. The mixture was extracted with ether (150 ml), and dried over magnesium sulfate. The solvent was evaporated under reduced pressure, to thereby yield 4.93 g of the purified target compound (yield: 46.1%).

$^1$H-NMR (CDCl$_3$, ppm); 2.28 (3H, s), 2.50 (3H, s), 3.69 (2H, s), 7.02 (1H, d, J=8.10 Hz), 7.27 (1H, dd, J=8.10 Hz, 1.89 Hz), 7.45 (1H, d, J=1.89 Hz), Example 32

Production of trans-N-(6,6-Dimethyl-2-hepten-4-ynyl)-N-methyl-(5-bromo-2-methylbenzyl)amine (Compound 32)

N-(5-bromo-2-methylbenzyl)methylamine (2.89 g; 13.5 mmol) and sodium carbonate (1.50 g; 14.2 mmol) were added to N,N-dimethylformamide (25 ml). While the mixture was stirred at room temperature, 1-bromo-6,6-dimethyl-2-hepten-4-yne (2.71 g; 13.5 mmol) in N,N-dimethylformamide (5 ml) was added dropwise. The mixture was stirred for 21 hours at room temperature, and concentrated under reduced pressure. Water was added to the residue, and the mixture was extracted with ether (150 ml). The organic layer was washed with saturated brine, and dried over anhydrous sodium sulfate. The solvent was evaporated under reduced pressure, and the residue was purified by silica gel column chromatography (n-hexane:ethyl acetate=50:1), to thereby yield 1.10 g of the target compound as orange oily matter (yield: 24.4%).

$^1$H-NMR (CDCl$_3$, ppm); 1.24 (9H, s), 2.17 (3H, s), 2.27 (3H, s), 3.04 (2H, dd, J=6.48 Hz, 1.35 Hz), 3.38 (2H, s), 5.64 (1H, dt, J=15.66 Hz, 1.35 Hz), 6.07 (1H, dt, J=15.66 Hz, 6.48 Hz), 7.00 (1H, d, J=8.37 Hz), 7.26 (1H, dd, J=8.37 Hz, 1.89 Hz), 7.44 (1H, d, J=1.89 Hz).

Example 33

Production of trans-2-[3-{N-(6,6-Dimethyl-2-hepten-4-ynyl)-N-methylaminomethyl}-4-methylphenyl]-2-propanol (Compound 33)

Compound 32 (1.10 g) was dissolved in tetrahydrofuran (10 ml), and the solution was cooled to −78° C. by use of a mixture of dry ice and acetone solvent. n-butyl lithium in n-hexane (1.63 M: 2.1 ml; 1.04 eq) was slowly added dropwise to the mixture, and stirred for 5 minutes, followed by dropwise addition of acetone (290 μl; 1.2 eq). The mixture was stirred for 15 minutes, and gradually brought to room temperature. Saturated aqueous ammonium chloride solution was added dropwise to the mixture, and the reaction was stopped, followed by extraction with ether (120 ml). The organic layer was dried over magnesium sulfate, and the solvent was evaporated under reduced pressure. The residue was purified by silica gel column chromatography (n-hexane ethyl acetate=5:1), to thereby yield 520 mg of the target compound (yield: 50.4%).

$^1$H-NMR (CDCl$_3$, ppm); 1.24 (9H, s), 1.57 (6H, s), 2.18 (3H, s), 2.33 (3H, s), 3.04 (2H, dd, J=6.48 Hz, 1.08 Hz), 3.44 (2H, s), 5.64 (11H, d, J=15.93 Hz), 6.08 (1H, dt, J=15.93 Hz, 6.48 Hz), 7.11 (1H, d, J=7.83 Hz), 7.27 (1H, dd, J=7.83 Hz, 1.89 Hz), 7.39 (1H, d, J=1.89 Hz).

Example 34

Production of trans-N-(6,6-Dimethyl-2-hepten-4-ynyl)-N-methyl-(5-isopropenyl-2-methylbenzyl) amine (Compound 34)

Compound 33 (520 mg; 1.66 mmol) was dissolved in pyridine (6 ml), and phosphorus oxychloride (1.27 g; 8.3 mmol) was added thereto. The mixture was stirred for 1 hour at 130–140° C., and then cooled. The reaction mixture was poured into water, and alkalinized with sodium hydroxide pellet. The mixture was extracted with ether (120 ml), and dried over magnesium sulfate. The solvent was evaporated under reduced pressure, and the residue was purified by silica gel column chromatography (n-hexane:ethyl acetate=20:1), to thereby yield 420 mg of the target compound (yield: 85.7%).

$^1$H-NMR (CDCl$_3$, ppm); 1.24 (9H, s), 2.14 (3H, s), 2.18 (3H, s), 2.33 (3H, s), 3.05 (2H, dd, J=6.48 Hz, 1.62 Hz), 3.44 (2H, s), 5.03 (1H, s), 5.34 (1H, s), 5.65 (1H, d, J=15.93 Hz), 6.08 (1H, dt, J=15.93 Hz, 6.48 Hz), 7.10 (1H, d, J=8.10 Hz), 7.26 (1H, dd, J=8.10 Hz, 1.62 Hz), 7.38 (1H, d, J=1.62 Hz).

Example 35

Production of trans-N-(6,6-Dimethyl-2-hepten-4-ynyl)-N-methyl-(5-isopropenyl-2-methylbenzyl) amine Hydrochloride (Compound 35)

The procedure described in Example 3 was repeated, except that Compound 34 (420 mg; 1.42 mmol) was used, to thereby yield 465 mg of the target compound (yield: 98.5%).

$^1$H-NMR (CDCl$_3$, ppm); 1.25 (9H, s), 2.19 (3H, s), 2.45 (3H, s), 2.64 (3H, d, J=4.86 Hz), 3.61 (1H, m), 3.78 (1H, m). 4.02 (1H, dd, J=13.23 Hz, 6.08 Hz), 4.30 (1H, dd, J=13.23 Hz, 5.00 Hz), 5.13 (1H, s), 5.50 (1H, s), 5.86 (1H, d, J=15.66 Hz), 6.33 (1H, dt, J=15.66 Hz, 7.56 Hz), 7.21 (1H, d, J=7.83 Hz), 7.44 (1H, dd, J=7.83 Hz, 1.89 Hz), 7.91 (1H, d, J=1.89 Hz), 12.70 (1H, brs).

Example 36

Production of trans-N-(6,6-Dimethyl-2-hepten-4-ynyl)-N-methyl-(2-bromobenzyl)amine (Compound 36)

The procedure described in Example 1 was repeated, except that N-(6,6-dimethyl-2-hepten-4-ynyl)methylamine (1.96 g; 13.0 mmol), potassium carbonate (1.44 g; 13.6 mmol), and 2-bromobenzylbromide (3.25 g; 13.0 mmol) were used, to thereby yield 2.35 g of the target compound (yield: 56.5%).

$^1$H-NMR (CDCl$_3$, ppm); 1.24 (9H, s), 2.24 (3H, s), 3.11 (2H, dd, J=6.48 Hz, 1.35 Hz), 3.58 (2H, s), 5.68 (1H, dt, J=15.93 Hz, 1.35 Hz), 6.10 (1H, dt, J=15.93 Hz, 6.48 Hz), 7.10 (1H, td, J=7.83 Hz, 1.35 Hz), 7.28 (1H, td, J=7.83 Hz, 1.08 Hz), 7.47 (1H, dd, J=7.83 Hz, 1.35 Hz), 7.53 (1H, dd, J=7.83 Hz, 1.08 Hz).

Example 37

Production of 2-[3-{N-(6,6-Dimethyl-2-hepten-4-ynyl)-N-methylaminomethyl}phenyl]-2-propanol (Compound 37)

The procedure described in Example 17 was repeated, except that Compound 36 (2.35 g; 7.3 mmol), n-butyl lithium in n-hexane (1.56 M: 5.2 ml; 8.1 mmol), and acetone (1 ml) were used, to thereby yield 940 mg of the target compound (yield: 42.8%).

$^1$H-NMR (CDCl$_3$, ppm); 1.23 (9H, s), 1.60 (6H, s), 2.19 (3H, s), 3.07 (2H, dd, J=7.02 Hz, 1.35 Hz), 3.78 (2H, s), 5.61 (1H, dt, J=15.93 Hz, 1.35 Hz), 6.05 (1H, dt, J=15.93 Hz, 7.02 Hz), 7.09~7.18 (2H, m), 7.26 (1H, m), 7.36 (1H, d, J=7.56 Hz), 8.45 (1H, brd).

Example 38

Production of trans-N-(6,6-Dimethyl-2-hepten-4-ynyl)-N-methyl-(2-isopropenylbenzyl)amine (Compound 38)

A mixture of pyridine (10 ml), Compound 37 (940 mg; 3.1 mmol), and thionyl chloride (1.12 g; 9.4 mmol) was stirred for 15 minutes while being cooled with ice, and then stirred for 15 minutes at room temperature. Subsequently, unreacted pyridine and thionyl chloride were evaporated under reduced pressure, and saturated aqueous sodium bicarbonate solution was added thereto. The mixture was extracted with ether twice (70 ml and 50 ml), and the combined organic layer was washed with saturated brine, followed by drying over magnesium sulfate. The solvent was evaporated under reduced pressure, and the residue was purified by silica gel column chromatography (n-hexane:ethyl acetate=20:1), to thereby yield 360 mg of the target compound (yield: 40.8%).

$^1$H-NMR (CDCl$_3$, ppm); 1.24 (9H, s), 2.04 (3H, s), 2.15 (3H, s), 3.01 (2H, dd, J=6.48 Hz, 1.35 Hz), 3.49 (2H, s), 4.81 (1H, s), 5.17 (1H, s), 5.64 (1H, dt, J=15.66 Hz, 1.35 Hz), 6.06 (1H, dt, J=15.66 Hz, 6.48 Hz), 7.10 (1H, m), 7.15~7.27 (2H, m), 7.48 (1H, dd, J=7.56 Hz, 1.89 Hz).

Example 39

Production of trans-N-(6,6-Dimethyl-2-hepten-4-ynyl)-N-methyl-(2-isopropenylbenzyl)amine Hydrochloride (Compound 39)

The procedure described in Example 19 was repeated, except that Compound 38 (360 mg; 1.28 mmol) and hydrogen chloride in ethyl acetate (4 N: 0.35 ml; 1.4 mmol) were used, to thereby yield 370 mg of the target compound (yield: 91.0%).

m. p. 175.5~177° C.; $^1$H-NMR (CDCl$_3$, ppm); 1.24 (9H, s), 2.05 (3H, brs), 2.57 (3H, d, J=4.86 Hz), 3.50 (1H, m), 3.72 (1H, m), 4.16 (1H, dd, J=13.23 Hz, 6.48 Hz), 4.36 (1H, dd, J=13.50 Hz, 5.40 Hz), 4.86 (1H, s), 5.36 (1H, s), 5.81 (H, d, J=15.39 Hz), 6.30 (1H, dt, J=15.39 Hz, 7.56 Hz), 7.22 (1H, dd, J=7.56 Hz, 1.62 Hz), 7.37 (1H, td, J=7.56 Hz, 1.62

Hz), 7.43 (1H, td, J=7.56 Hz, 1.62 Hz), 8.18 (1H, dd, J=7.56 Hz, 1.62 Hz), 12.65 (1H, brs).

Referential Example 12

Production of 3'-(N-Isopropylaminomethyl) acetophenone

The procedure described in Referential Example 4 was repeated, except that isopropylamine (instead of triethylamine) (11.82 g; 200 mmol) and 3'-bromomethylacetophenone (4.26 g; 20 mmol) were used, to thereby yield 2.67 g of the target compound (yield: 69.9%).

$^1$H-NMR (CDCl$_3$, ppm); 1.11 (6H, d, J=6.21 Hz), 2.62 (3H, s), 2.86 (1H, quintet, J=6.21 Hz), 3.84 (2H, s), 7.42 (1H, t, J=7.56 Hz), 7.55 (1H, d, brd), 7.84 (1H, dt, J=7.56 Hz, 1.62 Hz), 7.92 (1H, brd).

Example 40

Production of trans-3'-[N-(6,6-Dimethyl-2-hepten-4-ynyl)-N-isopropylaminomethyl]acetophenone (Compound 40)

The procedure described in Example 13 was repeated, except that 3'-(N-isopropylaminomethyl)acetophenone (1.66 g; 8.7 mmol), sodium carbonate (925 mg; 8.7 mmol), and 1-bromo-6,6-dimethyl-2-hepten-4-yne (1.74 g; 8.7 mmol) were used, to thereby yield 1.67 g of the target compound (yield: 61.8%).

$^1$H-NMR (CDCl$_3$, ppm); 1.03 (6H, d, J=6.48 Hz), 1.23 (9H, s), 2.61 (3H, s), 2.95 (1H, quintet, J=6.48 Hz), 3.07 (2H, dd, J=6.21 Hz, 1.62 Hz), 3.59 (2H, s), 5.65 (1H, dt, J=15.66 Hz, 1.62 Hz), 6.00 (1H, dt, J=15.66 Hz, 6.21 Hz), 7.39 (1H, t, J=7.56 Hz), 7.58 (1H, d, J=7.56 Hz), 7.81 (1H, d, J=7.56 Hz), 7.91 (1H, s).

Example 41

Production of trans-N-(6,6-Dimethyl-2-hepten-4-ynyl)-N-isopropyl-(3-isopropenylbenzyl)amine (Compound 41)

The procedure described in Example 9 was repeated, except that methyl triphenylphosphonium bromide (2.88 g; 8.1 mmol), n-butyl lithium in n-hexane (1.56 M: 5.2 ml; 8.1 mmol), and Compound 40 (1.67 g; 5.4 mmol) were used, to thereby yield 1.50 g of the target compound (yield: 90.4%).

$^1$H-NMR (CDCl$_3$, ppm); 1.01 (6H, d, J=6.75 Hz), 1.23 (9H, s), 2.16 (3H, s), 2.97 (1H, quintet, J=6.75 Hz), 3.07 (2H, dd, J=5.94 Hz, 1.62 Hz), 3.54 (2H, s), 5.07 (1H, s), 5.36 (1H, s), 5.66 (1H, dt, J=15.93 Hz, 1.62 Hz), 6.02 (1H, dt, J=15.93 Hz, 5.94 Hz), 7.23~7.37 (3H, m), 7.44 (1H, s).

Example 42

Production of trans-N-(6,6-Dimethyl-2-hepten-4-ynyl)-N-isopropyl-(3-isopropenylbenzyl)amine Hydrochloride (Compound 42)

The procedure described in Example 12 was repeated, except that Compound 41 (1.50 g; 4.9 mmol) and 4N hydrochloric acid—ethyl acetate (1.3 ml; 5.2 mmol) were used, to thereby yield 1.43 g of the target compound (yield: 85.3%).

m. p. 165.5~167° C.; $^1$H-NMR (CDCl$_3$, ppm); 1.23 (9H, s), 1.46 (3H, d, J=6.48 Hz), 1.49 (3H, d, J=6.48 Hz), 2.19 (3H, s), 3.45~3.70 (3H, m), 407 (1H, dd, J=13.50 Hz, 6.48 Hz), 4.14 (1H, dd, J=13.50 Hz, 6.48 Hz), 5.15 (1H, s), 5.50 (1H, s), 5.73 (1H, d, J=15.93 Hz), 6.44 (1H, dt, J=15.93 Hz, 7.83 Hz), 7.39 (1H, t, J=7.70 Hz), 7.52 (1H, d, J=7.70 Hz), 7.63 (1H, d, J=7.70 Hz), 7.90 (1H, s). 12.60 (1H, brs).

Referential Example 13

Production of 3'-(N-Ethylaminomethyl) acetophenone

The procedure described in Referential Example 4 was repeated, except that ethylamine hydrochloride (16.31 g; 200 mmol), sodium hydroxide (instead of triethylamine) (8 g; 200 mmol), and 3'-bromomethylacetophenone (4.26 g; 20 mmol) were used, to thereby yield 2.36 g of the target compound (yield: 66.7%).

$^1$H-NMR (CDCl$_3$, ppm); 1.15 (3H, t, J=7.02 Hz 2.62 (3H, s), 2.70 (2H, q, J=7.02 Hz), 3.86 (2H, s), 7.43 (1H, t, J=7.56 Hz), 7.55 (1H, d, J=7.56 Hz), 7.85 (1H, d, J=7.56 Hz), 7.92 (1H, s).

Example 43

Production of trans-3'-[N-(6,6-Dimethyl-2-hepten-4-ynyl)-N-ethylaminomethyl]acetophenone (Compound 43)

The procedure described in Example 13 was repeated, except that 3'-(N-ethylaminomethyl)acetophenone (1.24 g; 7 mmol), sodium carbonate (instead of potassium carbonate) (745 mg; 7 mmol), and 1-bromo-6,6-dimethyl-2-hepten-4-yn (1.41 g; 7 mmol) were used, to thereby yield 1.30 g of the target compound (yield: 62.5%).

$^1$H-NMR (CDCl$_3$, ppm); 1.05 (3H, t J=7.02 Hz), 1.24 (9H, s), 2.51 (2H, q, J=7.02 Hz), 2.61 (3H, s), 3.10 (2H, dd, J=6.48 Hz, 1.62 Hz), 3.61 (2H, s), 5.65 (1H, dt, J=15.66 Hz, 1.62 Hz), 6.07 (1H, dt, J=15.66 Hz, 6.48 Hz), 7.40 (1H, t, J=7.56 Hz), 7.56 (1H, d, J=7.56 Hz), 7.83 (1H, d, J=7.56 Hz), 7.90 (1H, s).

Example 44

Production of trans-N-(6,6-Dimethyl-2-hepten-4-ynyl)-N-ethyl-(3-isopropenylbenzyl)amine (Compound 44)

The procedure described in Example 9 was repeated, except that methyl triphenylphosphonium bromide (2.35 g; 6.6 mmol), n-butyl lithium in n-hexane (1.56 M: 4.2 ml; 6.6 mmol), and Compound 43 (1.3 g; 4.4 mmol) were used, to thereby yield 950 mg of the target compound (yield: 73.6%).

$^1$H-NMR (CDCl$_3$, ppm); 1.05 (3H, t, J=7.02 Hz), 1.24 (9H, s), 2.16 (3H, s), 2.52 (2H, q, J=7.02 Hz), 3.11 (2H, d, J=6.48 Hz), 5.08 (1H, s), 5.37 (1H, s), 5.65 (1H, d, J=15.93 Hz), 6.09 (1H, dt, J=15.93 Hz, 6.48 Hz), 7.23~7.40 (3H, m), 7.42 (1H, s).

Example 45

Production of trans-N-(6,6-Dimethyl-2-hepten-4-ynyl)-N-ethyl-(3-isopropenylbenzyl)amine Hydrochloride (Compound 45)

The procedure described in Example 12 was repeated, except that Compound 44 (950 mg; 3.2 mmol) and 4N hydrochloric acid—ethyl acetate solution (0.85 ml; 3.4 mmol) were used, to thereby yield 710 mg of the target compound (yield: 66.5%).

m. p. 93~97° C.; $^1$H-NMR (CDCl$_3$, ppm); 1.25 (9H, s), 1.45 (3H, d, J=7.43 Hz), 1.48 (3H, d, J=7.43 Hz), 2.19 (3H, s), 3.06 (2H, m), 3.56 (1H, m), 3.71 (1H, m), 4.14 (2H, brs), 5.17 (1H, s), 5.49 (1H, s), 5.82 (1H, d, J=5.80 Hz), 6.26 (1H, dt, J=15.80 Hz, 7.56 Hz), 7.41 (1H, t, J=7.70 Hz), 7.54 (1H, d, J=7.70 Hz), 7.57 (1H, d, J=7.70 Hz), 7.80 (1H, s), 12.76 (1H, brs).

Referential Example 14

Production of N-Cinnamyl Methylamine

Triethylamine (0.66 g; 6.55 mmol) was added to 40% solution of methylamine in methanol (20 ml). While the mixture was stirred at room temperature, cinnamyl chloride (1.00 g; 6.55 mmol) was added dropwise. After completion of the addition, the mixture was stirred for 20 hours at room temperature, and excess methylamine and methanol were removed under reduced pressure. The residue was taken up in a mixture of diethyl ether and 2N hydrochloric acid (100 ml–100 ml), and the aqueous layer was neutralized with aqueous sodium hydroxide solution, followed by extraction with chloroform (100 ml). The organic layer was washed with saturated aqueous sodium bicarbonate solution and then with saturated brine, and dried over sodium sulfate. The solvent was evaporated under reduced pressure, to thereby yield 0.80 g of the target compound as yellow oily matter (yield: 83.0%).

$^1$H-NMR (CDCl$_3$, ppm); 2.48 (3H, s), 3.38 (2H, dd, J=1.22 Hz, 6.21 Hz), 6.29 (1H, dt, J=16.5 Hz, 6.21 Hz), 6.54 (1H, d, J=16.5 Hz), 7.19~7.40 (5H, m).

Example 46

Production of 3'-(N-Cinnamyl-N-methylaminomethyl)acetophenone (Compound 46)

The procedure described in Example 1 was repeated, except that N-cinnamyl methylamine [instead of N-(6,6-dimethyl-2-hepten-4-ynyl)methylamine] (650 mg; 3.04 mmol), sodium carbonate (instead of potassium carbonate) (1.5 eq), and 3'-bromomethylacetophenone (1.5 eq) were used, to thereby yield 0.42 g of the target compound (yield: 49.5%).

$^1$H-NMR (CDCl$_3$, ppm); 2.25 (3H, s), 2.61 (3H, s), 3.21 (2H, dd, J=0.95 Hz, 6.35 Hz), 3.60 (2H, s), 6.30 (1H, dt, J=15.9 Hz, 6.75 Hz), 6.55 (1H, d, J=15.9 Hz), 7.20~7.46 (6H, m), 7.57 (1H, d, J=7.56 Hz), 7.85 (1H, d, J=7.56 Hz), 7.92 (1H, s).

Example 47

Production of N-Cinnamyl-N-methyl-(3-isopropenylbenzyl)amine (Compound 47)

The procedure described in Example 2 was repeated, except that Compound 46 (0.42 g; 1.50 mmol), methyl triphenylphosphonium bromide (1.5 eq), and n-butyl lithium in n-hexane (1.68 M: 1.5 eq) were used, to thereby yield 0.21 g of the target compound (yield: 50.5%).

$^1$H-NMR (CDCl$_3$, ppm); 2.09 (3H, s), 2.19 (3H, s), 3.13 (2H, d, J=6.75 Hz), 3.50 (2H, s), 5.01 (1H, t, J=1.49 Hz), 5.31 (1H, s), 6.25 (1H, dt, J=16.5 Hz, 6.75 Hz), 6.48 (1H d, J=15.9 Hz), 7.12~7.36 (9H, m).

Example 48

Production of N-Cinnamyl-N-methyl-(3-isopropenylbenzyl)amine Hydrochloride (Compound 48)

The procedure described in Example 3 was repeated, except that N-cinnamyl-N-methyl-(3-isopropenylbenzyl) amine (0.21 g; 7.57×10$^{-1}$ mmol) and 4N hydrochloric acid (1 eq.) ethyl acetate were used, to thereby yield 0.20 g of the target compound as white crystals (yield: 84.2%).

IR (KBr tablet, cm$^{-1}$); 2940, 2918, 2895, 2676, 2629, 2561, 1467, 1452, 972, 912; m. p. 126~130° C.; $^1$H-NMR (CDCl$_3$, ppm); 2.19 (3H, s), 2.69 (3H, s), 3.60~3.81 (2H, m), 4.09~4.33 (H, brm), 5.17 (1H, t, J=1.49 Hz), 5.48 (1H, s), 6.54 (1H, dt, J=15.9 Hz, 7.56 Hz), 6.72 (1H, d, J=15.9 Hz), 7.32–7.40 (3H, m), 7.43~7.47 (3H, m), 7.54~7.57 (2H, m), 7.76 (1H, s), 12.9 (1H, brs).

Example 49

Production of trans-N-(6,6-Dimethyl-2-hepten-4-ynyl)-N-methyl-(3-isopropenyl-2-methylbenzyl) amine Hydrochloride (Compound 52)

The procedure described in Referential Example 9 was repeated, except that 3-bromo-o-xylene was used as a starting compound, to thereby yield 3-bromo-2-methylbenzyl bromide and an isomer, 2-bromo-6-methylbenzyl bromide. The procedure described in Referential Example 10 was repeated, except that the thus-obtained unpurified products were used as starting materials, to thereby yield N-(3-bromo-2-methylbenzyl)methylamine. The purification procedure also yielded N-(2-bromo-6-methylbenzyl) methylamine as a byproduct. The procedure described in Example 28 was repeated, except that N-(3-bromo-2-methylbenzyl)methylamine was reacted with 1-bromo-6,6-dimethyl-2-hepten-4-yne, to thereby yield trans-N-(6,6-dimethyl-2-hepten-4-ynyl)-N-methyl-(3-bromo-2-methylbenzyl)amine (Compound 49). The procedure described in Example 29 was repeated, except that Compound 49 was used as a starting compound, to thereby yield trans-2-[3-{N-(6,6-dimethyl-2-hepten-4-ynyl)-N-methylaminomethyl}-2-methylphenyl]-2-propanol (Compound 50). Subsequently, the procedure described in Example 30 was repeated, except that Compound 50 was used as a starting compound, to thereby yield trans-N-(6,6-dimethyl-2-hepten-4-ynyl)-N-methyl-(3-isopropenyl-2-methylbenzyl)amine (Compound 51). Subsequently, the procedure described in Example 31 was repeated, except that Compound 51 was reacted with hydrogen chloride in ethyl acetate (4 N), to thereby yield Compound 52.

m. p. 205.5~207° C.; $^1$H-NMR (CDCl$_3$, ppm); 1.24 (9H, s), 2.01 (3H, s), 2.41 (3H, s), 2.66 (3H, d, J=4.86 Hz), 3.63 (1H, m), 3.78 (1H, m), 4.05 (1H, dd, J=13.23 Hz, 6.48 Hz), 4.33 (1H, dd, J=13.23 Hz, 4.59 Hz), 4.84 (1H, s), 5.22 (1H, s), 5.86 (1H, d, J=15.93 Hz), 6.32 (1H, dt, J=15.93 Hz, 7.56 Hz), 7.19 (1H, d, J=7.56 Hz), 7.26 (1H, t, J=7.56 Hz), 7.63 (1H, d, J=7.56 Hz), 12.53 (1H, brs).

Example 50

Production of trans-N-(6,6-Dimethyl-2-hepten-4-ynyl)-N-methyl-(2-isopropenyl-6-methylbenzyl) amine Hydrochloride (Compound 56)

The procedure described in Example 28 was repeated, except that N-(2-bromo-6-methylbenzyl)methylamine obtained in Example 49 was reacted with 1-bromo-6,6-dimethyl-2-hepten-4-yne, to thereby yield trans-N-(6,6-dimethyl-2-hepten-4-ynyl)-N-methyl-(2-bromo-6-methylbenzyl)amine (Compound 53). The procedure described in Example 29 was repeated, except that Compound 53 was used as a starting compound, to thereby yield trans-2-[2-(N-(6,6-dimethyl-2-hepten-4-ynyl)-N-methylaminomethyl)-3-methylphenyl]-2-propanol (Compound 54). Subsequently, the procedure described in Example 30 was repeated, except that Compound 54 was used as a starting compound, to thereby yield trans-N-(6,6-dimethyl-2-hepten-4-ynyl)-N-methyl-(2-isopropenyl-6-methylbenzyl)amine (Compound 55). Subsequently, the procedure described in Example 31 was repeated, except that Compound 55 was reacted with hydrogen chloride in ethyl acetate (4 N), to thereby yield Compound 56.

m. p. 164~165° C.; $^1$H-NMR (CDCl$_3$, ppm); 1.25 (9H, s), 2.05 (3H, s), 2.53 (3H, d, J=5.13 Hz), 2.70 (3H, s), 3.64 (1H, m), 3.80 (1H, m), 4.16 (1H, m), 4.44 (1H, m), 4.92 (1H, s), 5.38 (1H, s), 5.92 (1H, d, J=15.66 Hz), 6.36 (1H, dt, J=15.66 Hz, 7.70 Hz), 7.06 (1H, d, J=7.83 Hz), 7.22 (1H, d, J=7.83 Hz), 7.30 (1H, t, J=7.83 Hz), 11.61 (1H, brs).

Example 51

Production of trans-N-(6,6-Dimethyl-2-hepten-4-ynyl)-N-methyl-(2-fluoro-5-isopropenylbenzyl) amine Hydrochloride (Compound 60)

The procedure described in Referential Example 9 was repeated, except that 5-bromo-2-fluorotoluene was used as a starting compound, to thereby yield 5-bromo-2-fluorobenzyl bromide. Subsequently, the procedure described in Referential Example 10 was repeated, except that 5-bromo-2-fluorobenzyl bromide was used as a starting compound, to thereby yield N-(5-bromo-2-fluorobenzyl)methylamine. Subsequently, the procedure described in Example 28 was repeated, except that N-(5-bromo-2-fluorobenzyl) methylamine was reacted with 1-bromo-6,6-dimethyl-2-hepten-4-yne, to thereby yield trans-N-(6,6-dimethyl-2-hepten-4-ynyl)-N-methyl-(5-bromo-2-fluorobenzyl)amine (Compound 57). The procedure described in Example 29 was repeated, except that Compound 57 was used as a starting compound, to thereby yield trans-2-[3-{N-(6,6-dimethyl-2-hepten-4-ynyl)-N-methylaminomethyl}-4-fluorophenyl]-2-propanol (Compound 58). Subsequently, the procedure described in Example 30 was repeated, except that Compound 58 was used as a starting compound, to thereby yield trans-N-(6,6-dimethyl-2-hepten-4-ynyl)-N-methyl-(2-fluoro-5-isopropenylbenzyl)amine (Compound 59). Subsequently, the procedure described in Example 31 was repeated, except that Compound 59 was reacted with 4N hydrogen chloride—ethyl acetate, to thereby yield Compound 60.

m. p. 184.5~187° C.; $^1$H-NMR (CDCl$_3$, ppm); 1.25 (9H, s), 2.19 (3H, s), 2.65 (3H, d, J=4.05 Hz), 3.52 (1H, m), 3.77 (1H, m), 4.14 (1H, dd, J=13.23 Hz, 5.40 Hz), 4.27 (1H, dd, J=13.23 Hz, 4.86 Hz), 5.16 (1H, s), 5.48 (1H, s), 5.86 (1H, d, J=15.39 Hz), 6.31 (1H, dt, J=15.39 Hz, 7.56 Hz), 7.10 (1H, t, J=9.18 Hz), 7.55 (1H, m), 8.10 (1H, dd, J=7.56 Hz, 2.43 Hz), 13.10 (1H, brs).

Referential Example 15

Production of 3-Bromo-5-fluorobenzoic Acid

Magnesium turnings (1.97 g) and iodine (catalytic amount) were added to ether (150 ml), and 1,3-dibromo-5-fluorobenzene (19.6 g) in ether (20 ml) was added dropwise under nitrogen atmosphere at such a rate that gentle reflux occurred. The mixture was refluxed for 3 hours, and left to cool. Crushed dry ice was added thereto, and the mixture was stirred for 1 hour. The reaction mixture was poured into water, and acidified with hydrochloric acid. The mixture was extracted with ether (200 ml), and dried over magnesium sulfate. The solvent was evaporated under reduced pressure, and the residue was purified by silica gel column chromatography (chloroform→chloroform:methanol=100:1), to thereby yield 9.37 g of the target compound (yield: 55.4%).

$^1$H-NMR (CDCl$_3$, ppm); 7.51 (1H, dt, J=7.83 Hz, 2.30 Hz), 7.74 (1H, d dd, J=8.91 Hz, 2.30 Hz, 1.35 Hz), 8.06 (1H, brs).

Referential Example 16

Production of 3-Bromo-5-fluorobenzyl Alcohol

Sodium borohydride (1.68 g) was added to diethylene glycol dimethyl ether (40 ml). While the mixture was stirred at room temperature, 3-bromo-5-fluorobenzoic acid (9.72 g) was added portionwise (six portions). After the crystals were completely dissolved, trifluoroborane ether complex (8.40 g) in diethylene glycol dimethyl ether (10 ml) was added dropwise thereto. The mixture was stirred for 5 hours, and poured into ice/water. The mixture was extracted with ether (200 ml), and washed with water, followed by drying over magnesium sulfate. The solvent was evaporated under reduced pressure, and the residue was purified by silica gel column chromatography (n-hexane:ethyl acetate= 10:1→5:1), to thereby yield a mixture of the target compound and diethylene glycol dimethyl ether. The thus-obtained mixture was analyzed by NMR to determine the content of diethylene glycol dimethyl ether. The content and the yield of the target compound as determined by NMR were 7.70 g and 84.6%, respectively.

$^1$H-NMR (CDCl$_3$, ppm); 1.87 (1H, t, J=5.94 Hz), 4.69 (2H, d, J=5.94 Hz), 7.04 (1H, brd), 7.16 (1H, dt, J=7.83 Hz, 1.89 Hz), 7.31 (1H, brs).

Referential Example 17

Production of 3-Bromo-5-fluorobenzyl Bromide

While phosphorus tribromide (3.65 g) was stirred, 47% aqueous hydrogen bromide solution (18.3 ml) was added in such a manner that the reaction temperature did not exceed 40° C. 3-Bromo-5-fluorobenzyl alcohol (7.70 g) in ethanol (6 ml) was added dropwise thereto, and the mixture was refluxed for 5 hours in an oil bath. The reaction mixture was cooled, and poured into ice/water, followed by extraction with n-hexane (150 ml). The organic layer was washed with saturated brine, and dried over magnesium sulfate. The solvent was evaporated under reduced pressure, and the residue was purified by silica gel column chromatography (n-hexane:ethyl acetate=30:1), to thereby yield 6.64 g of the target compound (yield: 66.0%).

$^1$H-NMR (CDCl$_3$, ppm); 4.39 (2H, s), 7.06 (1H, dt, J=8.91 Hz, 1.89 Hz), 7.19 (1H, dt, J=8.37 Hz, 1.89 Hz), 7.33 (1H, brs).

Example 52

Production of trans-N-(6,6-Dimethyl-2-hepten-4-ynyl)-N-methyl-(3-fluoro-5-isopropenylbenzyl) amine Hydrochloride (Compound 64)

The procedure described in Referential Example 10 was repeated, except that 3-bromo-5-fluorobenzyl bromide was used as a starting compound, to thereby yield N-(3-bromo-5-fluorobenzyl)methylamine. Subsequently, the procedure described in Example 28 was repeated, except that N-(3-bromo-5-fluorobenzyl)methylamine was reacted with 1-bromo-6,6-dimethyl-2-hepten-4-yne, to thereby yield trans-N-(6,6-dimethyl-2-hepten-4-ynyl)-N-methyl-(3-bromo-5-fluorobenzyl)amine (Compound 61). The procedure described in Example 29 was repeated, except that Compound 61 was used as a starting compound, to thereby yield trans-2-[3-{N-(6,6-dimethyl-2-hepten-4-ynyl)-N-methylaminomethyl}-5-fluorophenyl]-2-propanol (Compound 62). Subsequently, the procedure described in Example 30 was repeated, except that Compound 62 was used as a starting compound, to thereby yield trans-N-(6,6-dimethyl-2-hepten-4-ynyl)-N-methyl-(3-fluoro-5-isopropenylbenzyl)amine (Compound 63). Subsequently, the procedure described in Example 31 was repeated, except that Compound 63 was reacted with hydrogen chloride in ethyl acetate (4 N), to thereby yield Compound 64.

m. p. 183~145° C.; $^1$H-NMR (CDCl$_3$, ppm); 1.25 (9H, s), 2.17 (3H, s), 2.65 (3H, d, J=3.78 Hz), 3.57 (1H, m), 3.76 (1H, m), 3.99 (1H, dd, J=13.50 Hz, 5.40 Hz), 4.23 (1H, dd, J=13.50 Hz, 4.59 Hz), 5.22 (1H, s), 5.53 (1H, s), 5.86 (1H, d, J=15.66 Hz), 6.27 (1H, dt, J=15.66 Hz, 7.56 Hz) 7.23 (2H, d, J=9.72 Hz), 7.69 (1H, s), 13.15 (1H, brs).

Example 53

Production of trans-N-(6,6-Dimethyl-2-hepten-4-ynyl)-N-methyl-(3,5-bisisopropenylbenzyl)amine Hydrochloride (Compound 70)

The procedure described in Referential Example 9 was repeated, except that 3,5-dibromotoluene was used as a starting compound, to thereby yield 3,5-dibromobenzyl bromide. The procedure described in Referential Example 10 was repeated, except that 3,5-dibromobenzyl bromide was used as a starting compound, to thereby yield N-(3,5-dibromobenzyl)methylamine. Subsequently, the procedure described in Example 28 was repeated, except that N-(3,5-dibromobenzyl)methylamine was reacted with 1-bromo-6,6-dimethyl-2-hepten-4-yne, to thereby yield trans-N-(6,6-dimethyl-2-hepten-4-ynyl)-N-methyl-(3,5-dibromobenzyl)amine (Compound 65). The procedure described in Example 29 was repeated, except that Compound 65 was used as a starting compound, to thereby yield trans-2-[5-bromo-3-{N-(6,6-dimethyl-2-hepten-4-ynyl)-N-methylaminomethyl}phenyl]-2-propanol (Compound 66). Subsequently, the procedure described in Example 30 was repeated, except that Compound 66 was used as a starting compound, to thereby yield trans-N-(6,6-dimethyl-2-hepten-4-ynyl)-N-methyl-(3-bromo-5-isopropenylbenzyl)amine (Compound 67). The procedure described in Example 29 was repeated, except that Compound 67 was used as a starting compound, to thereby yield trans-2-[3-{N-(6,6-dimethyl-2-hepten-4-ynyl)-N-methylaminomethyl}-5-isopropenylphenyl]-2-propanol (Compound 68). Subsequently, the procedure described in Example 30 was repeated, except that Compound 68 was used as a starting compound, to thereby yield trans-N-(6,6-dimethyl-2-hepten-4-ynyl)-N-methyl-(3,5-bisisopropenylbenzyl)amine (Compound 69). As a final step, the procedure described in Example 31 was repeated, except that Compound 69 was used, to thereby yield Compound 70.

m. p. 146.5~148.5° C.; $^1$H-NMR (CDCl$_3$, ppm); 1.25 (9H, s), 2.20 (6H, s), 2.65 (3H, d, J=4.86 Hz), 3.55 (1H, m), 3.72 (1H, m), 4.03 (1H, dd, J=12.96 Hz, 5.67 Hz), 4.23 (1H, dd, J=12.96 Hz, 5.13 Hz), 5.17 (1H, s), 5.47 (1H, s). 5.83 (1H, d, J=15.39 Hz), 6.29 (1H, dt, J=15.39 Hz, 7.56 Hz), 7.61 (1H, d, J=1.35 Hz), 7.64 (1H, d, J=1.35 Hz), 13.01 (1H, brs).

Example 54

Production of trans-N-(6,6-Dimethyl-2-hepten-4-ynyl)-N-methyl-(3-isopropenyl-4-methylbenzyl)amine Hydrochloride (Compound 74)

The procedure described in Referential Example 16 was repeated, except that 3-bromo-4-methylbenzoic acid was used as a starting compound, to thereby yield 3-bromo-4-methyl benzyl alcohol. Subsequently, the procedure described in Referential Example 17 was repeated, except that 3-bromo-4-methyl benzyl alcohol-was used as a starting compound, to thereby yield 3-bromo-4-methylbenzyl bromide. Subsequently, the procedure described in Referential Example 10 was repeated, except that 3-bromo-4-methylbenzyl bromide was used as a starting compound, to thereby yield N-(3-bromo-4-methylbenzyl)methylamine. The procedure described in Example was repeated, except that N-(3-bromo-4-methylbenzyl)methylamine was reacted with 1-bromo-6,6-dimethyl-2-hepten-4-yne, to thereby yield trans-N-(6,6-dimethyl-2-hepten-4-ynyl)-N-methyl-(3-bromo-4-methylbenzyl)amine (Compound 71). The procedure described in Example 29 was repeated, except that Compound 71 was used as a starting compound, to thereby yield trans-2-[5-{N-(6,6-dimethyl-2-hepten-4-ynyl)-N-methylaminomethyl}-2-methylphenyl]-2-propanol (Compound 72). Subsequently, the procedure described in Example 30 was repeated, except that Compound 72 was used as a starting compound, to thereby yield trans-N-(6,6-dimethyl-2-hepten-4-ynyl)-N-methyl-(3-isopropenyl-4-methylbenzyl)amine (Compound 73). Subsequently, the procedure described in Example 31 was repeated, except that Compound 73 was reacted with hydrogen chloride in ethyl acetate (4 N), to thereby yield Compound 74.

m. p. 186~188° C.; $^1$H-NMR (CDCl$_3$, ppm); 1.24 (9H, s), 2.05 (3H, s), 2.33 (3H, s), 2.62 (3H, d, J=4.32 Hz), 3.49 (1H, m), 3.71 (1H, m), 3.99 (1H, dd, J=13.10 Hz, 5.27 Hz), 4.17 (1H, dd, J=13.10 Hz, 4.73 Hz), 4.89 (1H, s), 5.23 (1H, s), 5.83 (1H, d, J=15.93 Hz), 6.28 (1H, dt, J=15.93 Hz, 7.70 Hz), 7.27 (1H, brs), 7.28 (1H, d, J=7.70 Hz), 7.44 (1H, dd, J=7.70 Hz, 1.76 Hz), 12.83 (1H, brs).

Referential Example 18

Production of N-(4-tert-Butylbenzyl)methylamine p-tert-butylbenzoic acid (10.1 g; 56.6 mmol) and thionyl chloride (20.2 g) were added to chloroform (100 ml), and the mixture was refluxed for 5 hours. The solvent and excess thionyl chloride were removed under reduced pressure, and the residue was taken up in a small amount of methanol. The mixture was added dropwise to 40% methylamine in methanol (17 ml) in an ice bath. After completion of the addition, the mixture was removed from the ice bath, and stirred for 48 hours at room temperature. 2N Hydrochloric acid (100 ml) was added to the reaction mixture, and the resultant mixture was extracted with dichloromethane. The organic layer was washed with water and then with saturated brine, and dried over magnesium sulfate. The solvent was evaporated under reduced pressure, and the thus-obtained white crystals were dissolved in dichloromethane. The solution was washed with saturated aqueous sodium bicarbonate solution (1 L) so as to remove p-tert-butylbenzoic acid (starting compound). The organic layer was dried over magnesium sulfate, and the solvent was evaporated under reduced pressure, to thereby yield 8.15 g of N-methyl-4-tert-butylbenzoic acid amide as white crystals (yield: 74.9%).

Subsequently, diethyl ether (110 ml), N-methyl-4-tert-butylbenzoic acid amide (8.15 g; 42.6 mmol), and lithium aluminum hydride (2.88 g; 85.2 mmol) were mixed, and the mixture was refluxed for 6 hours under nitrogen atmosphere. After completion of the reflux, the reaction mixture was cooled on ice, and water was added thereto so as to decompose excess lithium aluminum hydride. Aluminum hydroxide that precipitated was filtered off, and the filtrate was extracted with diethyl ether. The organic layer was washed with water and then with saturated brine, and dried over magnesium sulfate. The solvent was evaporated under reduced pressure, and the thus-obtained yellow oily matter was subjected to vacuum distillation (115–118° C./10 mmHg), to thereby yield 3.69 g of the target compound as yellow oily matter (yield: 48.9%).

$^1$H-NMR (CDCl$_3$, ppm); 1.31 (9H, s), 2.45 (3H, s), 7.24 (2H, d, J=8.37 Hz), 7.35 (2H, d, J=8.37 Hz), Referential Example 19

Production of N-(4-tert-Butylbenzyl)methylamine (Alternative Method)

p-tert-butyltoluene (14.8 g; 0.10 mol) was dissolved in carbon tetrachloride, and N-bromosuccinimide (17.8 g; 0.10 mol) and benzoyl peroxide (200 mg) were added thereto. The mixture was refluxed for 2 hours, and then cooled. Insoluble matter was filtered off, followed by washing with carbon tetrachloride. The filtrate was concentrated under reduced pressure, and the residue was dissolved in n-hexane, followed by drying over magnesium sulfate. The solvent was evaporated under reduced pressure, to thereby yield 22.7 g of p-tert-butylbenzyl bromide (yield: 100%). The thus-obtained product was analyzed by $^1$H-NMR, and was found to be a mixture of the target compound, starting compounds, and a dibromo compound (10:1:1). Sodium carbonate (10.6 g; 0.10 mol) was added to 40% solution of methylamine in methanol (200 ml). While the mixture was cooled in an ice bath, p-tert-butyl benzyl bromide (22.7 g; 0.10 mol) in methanol (20 ml) was added dropwise thereto. The mixture was removed from the ice bath, and stirred for 41 hours at room temperature. Methanol was removed under reduced pressure, and the residue was taken up in water, followed by extraction with ether (400 ml). The ether layer was extracted with 1N hydrochloric acid twice (200 ml and 100 ml), and the aqueous layer was extracted with ethyl acetate. The aqueous layer was alkalinized with aqueous 2N sodium hydroxide solution, and extracted with ether (400 ml), followed by drying over magnesium sulfate. The solvent was evaporated under reduced pressure, and the residue was purified by silica gel column chromatography (chloroform:methanol=200:1→100:1→20:1), to thereby yield 9.51 g of the target compound (yield: 53.7%).

Example 55

Production of 3'-[N-(4-tert-butylbenzyl)-N-methylaminomethyl]acetophenone (Compound 75)

N-(4-tert-butylbenzyl)methylamine (1.25 g; 7.04 mmol) and potassium carbonate (1.95 g; 14.1 mmol) were added to N,N-dimethylformamide (30 ml). While the mixture was stirred in an ice bath, 3'-bromomethylacetophenone (1.50 g; 7.04 mmol) in N,N-dimethylformamide (10 ml) was added dropwise. After completion of the addition, the mixture was removed from the ice bath, and stirred for 1 hour at room temperature. Reaction was stopped by pouring the mixture into ice+saturated aqueous sodium bicarbonate solution, followed by extraction with ethyl acetate (100 ml). The organic layer was washed with saturated aqueous sodium bicarbonate solution and then with saturated brine, and dried over anhydrous sodium sulfate. The solvent was evaporated under reduced pressure, and the residue was purified by silica gel column chromatography (chloroform), to thereby yield 1.42 g of the target compound as pale yellow oily matter (yield: 65.2%).

$^1$H-NMR (CDCl$_3$, ppm); 1.31 (9H, s), 2.19 (3H, s), 2.61 (3H, s), 3.51 (2H, s), 3.57 (2H, s), 7.22~7.94 (8H, m).

Example 56

Production of N-(4-tert-Butylbenzyl)-N-methyl-(3-isopropenylbenzyl)amine (Compound 76)

Methyl triphenylphosphonium bromide (1.97 g; 5.51 mmol) was suspended in tetrahydrofuran (15 ml). While the suspension was stirred under nitrogen atmosphere at room temperature, n-butyl lithium in n-hexane (1.68 M: 3.9 ml; 6.60 mmol) was added dropwise. After the reaction mixture turned deep red, the mixture was cooled in an ice bath, and Compound 1 (1.42 g; 4.59 mmol) in tetrohydrofuran (15 ml) was added dropwise thereto. After completion of the addition, the mixture was removed from the ice bath, and stirred for 30 minutes at room temperature. Reaction was stopped by pouring the mixture into ice/water, followed by extraction with diethyl ether (100 ml). The organic layer was washed with saturated aqueous sodium bicarbonate solution and then with saturated brine, and dried over anhydrous sodium sulfate. The solvent was evaporated under reduced pressure, and the residue was purified by silica gel column chromatography (n-hexane:ethyl acetate=10:1), to thereby yield 0.81 g of the target compound as yellow oily matter (yield: 57.4%).

$^1$H-NMR (CDCl$_3$, ppm); 1.33 (9H, s), 2.16 (3H, s), 2.20 (3H, s), 3.50 (2H, s), 3.52 (2H, s), 5.08 (1H, s), 5.37 (1H, s), 7.24~7.46 (8H, m).

Example 57

Production of N-(4-tert-Butylbenzyl)-N-methyl-(3-isopropenylbenzyl)amine Hydrochloride (Compound 77)

Compound 2 (0.45 g; 1.46 mmol) was dissolved in diisopropyl ether (150 ml). While the solution was stirred at room temperature, hydrogen chloride in ethyl acetate (4 N: 0.44 ml; 1.75 mmol) was added dropwise. The mixture was stirred for 14 hours at room temperature, and white crystals that precipitated were collected by filtration. The crystals were washed with diisopropyl ether, followed by drying in a desiccator under reduced pressure, to thereby yield 0.45 g of the target compound as white crystals (yield: 89.6%).

IR (KBr tablet, cm$^{-1}$); 2958, 2904, 2868, 2678, 2627, 2597, 2562, 2528, 1461, 915, 717; m. p. 185.0~1905° C.; $^1$H-NMR (CDCl$_3$, ppm); 1.33 (9H, s), 2.19 (3H, s), 2.58 (3H, d, J=4.32 Hz), 4.00~4.10 (2H, m), 4.20~4.30 (2H, m), 5.17 (1H, s), 5.47 (1H, s), 7.39~7.56 (8H, m), 7.74 (1H, s), 12.9 (1H, brs).

Example 58

Production of N-(4-tert-Butylbenzyl)-N-methyl-(3-bromobenzyl)amine (Compound 78)

N-(3-bromobenzyl)methylamine (2.00 g; 10.0 mmol) and sodium carbonate (2.02 g; 19.0 mmol) were added to N,N-dimethylformamide (20 ml). While the mixture was stirred at room temperature, 4-tert-butylbenzyl bromide (2.16 g; 9.52 mmol) in N,N-dimethylformamide (15 ml) was added dropwise. The mixture was stirred for 30 minutes at room temperature, and the reaction was stopped by pouring the mixture into ice/water, followed by extraction with ethyl acetate (100 ml). The organic layer was washed with saturated aqueous sodium bicarbonate solution and then with saturated brine, and dried over anhydrous sodium sulfate.

The solvent was evaporated under reduced pressure, and the residue was purified by silica gel column chromatography (n-hexane:ethyl acetate), to thereby yield 2.26 g of the target compound (yield: 68.5%).

$^1$H-NMR (CDCl$_3$, ppm); 1.32 (9H, s), 2.18 (3H, s), 3.47 (2H, s), 3.57 (2H, s), 7.17 (1H, t, J=7.56 Hz), 7.26~7.38 (6H, m), 7.53 (1H, s).

Example 59

Production of 3-[N-(4-tert-Butylbenzyl)-N-methylaminomethyl]benzaldehyde (Compound 79)

Compound 78 (2.26 g; 6.53 mmol) was dissolved in tetrahydrofuran (25 ml), and the solution was cooled to −75° C. by use of a mixture of dry ice and acetone solvent under nitrogen atmosphere. n-butyl lithium in n-hexane (1.56 M: 4.2 ml; 6.53 mmol) was slowly added dropwise to the mixture, and the resultant mixture was stirred for 15 minutes. Subsequently, N,N-dimethylformamide (0.95 g; 13.1 mmol) was added dropwise to the mixture, and the resultant mixture was gradually brought to room temperature. Reaction was stopped by dropwise addition of saturated aqueous ammonium chloride solution, followed by extraction with ether (100 ml). The organic layer was washed with saturated aqueous sodium bicarbonate solution and then with saturated brine, and dried over anhydrous sodium sulfate. The solvent was evaporated under reduced pressure, and the residue was purified by silica gel column chromatography (n-hexane:ethyl acetate=10:1), to thereby yield 0.59 g of the target compound (yield: 30.6%).

$^1$H-NMR (CDCl$_3$, ppm); 1.32 (9H, s), 2.20 (3H, s), 3.53 (2H, s), 3.58 (2H, s), 7.29 (2H, d, J=8.37 Hz), 7.36 (2H, d, J=8.37 Hz), 7.49 (1H, t, J=7.56 Hz), 7.66 (1H, d, J=7.56 Hz), 7.77 (1H, d, J=7.56 Hz), 7.94 (1H, s), 10.0 (1H, s).

Example 60

Production of N-(4-tert-Butylbenzyl)-N-methyl-(3-vinylbenzyl)amine (Compound 80)

Methyl triphenylphosphonium bromide (1.07 g; 3.00 mmol) was added to benzene (20 ml). While the mixture was stirred under nitrogen atmosphere at room temperature, n-butyl lithium in n-hexane (1.56 M: 1.9 ml; 3.00 mmol) was added dropwise. The mixture was stirred for 10 minutes, and Compound 5 (0.59 g; 2.00 mmol) in benzene (15 ml) was added dropwise thereto, followed by stirring for 3 hours at room temperature. Reaction was stopped by pouring the mixture into ice/water, followed by extraction with benzene (100 ml). The organic layer was washed with saturated aqueous sodium bicarbonate solution and then with saturated brine, and dried over anhydrous sodium sulfate. The solvent was evaporated under reduced pressure, and the residue was purified by silica gel column chromatography (n-hexane:ethyl acetate=20:1), to thereby yield 0.29 g of the target compound as pale yellow oily matter (yield: 49.4%).

$^1$H-NMR (CDCl$_3$, ppm); 1.31 (9H, s), 2.19 (3H, s), 3.44 (2H, s), 3.50 (2H, s), 5.24 (1H, dd, J=10.8 Hz, 0.81 Hz), 5.76 (1H, dd, J=17.8 Hz, 0.81 Hz), 6.73 (1H, dd, J=17.8 Hz, 10.3 Hz), 7.26~7.41 (8H, m).

Example 61

Production of N-(4-tert-Butylbenzyl)-N-methyl-(3-vinylbenzyl)amine Hydrochloride (Compound 81)

Compound 80 (0.29 g; 9.88×10$^{-1}$ mmol) was dissolved in diisopropyl ether (70 ml). While the solution was stirred at room temperature, 4N hydrochloric acid (1 eq.)—ethyl acetate (0.25 ml) was added dropwise. The mixture was stirred for 3 hours, and crystals that precipitated were collected by filtration. The crystals were washed with diisopropyl ether, followed by drying in a desiccator under reduced pressure, to thereby yield 0.29 g of the target compound as white crystals (yield: 89.0%).

IR (KBr tablet, cm$^{-1}$); 3462, 2959, 2904, 2870, 2855, 2688, 2632, 2561, 2543, 1485, 1463, 1451, 1417, 1394, 1363, 1067; m. p. 210~212° C.; $^1$H-NMR (CDCl$_3$, ppm); 1.27 (9H, s), 2.57 (3H, d, J=4.32 Hz), 3.99~4.10 (2H, m), 4.21~4.30 (2H, m), 5.35 (1H, d, J=10.8 Hz), 5.88 (1H, d, J=17.8 Hz), 6.73 (1H, dd, J=17.8 Hz, 10.8 Hz), 7.39~7.57 (7H, m), 7.69 (1H, s), 12.9 (1H, brs).

Example 62

Production of 3'-[N-(4-tert-Butylbenzyl)-N-cyclopropylaminomethyl]acetophenone (Compound 82)

3'-(N-cyclopropylaminomethyl)acetophenone (0.30 g; 1.59 mmol) and potassium carbonate (0.31 g; 2.27 mmol) were added to N,N-dimethylformamide (15 ml). While the mixture was stirred at room temperature, 4-tert-butylbenzyl bromide (0.29 g; 1.51 mmol) in N,N-dimethylformamide (5 ml) was added dropwise. The mixture was stirred for 1 hour at room temperature, and the reaction was stopped by pouring the mixture into ice+saturated aqueous sodium bicarbonate solution, followed by extraction with ethyl acetate (100 ml). The organic layer was washed with saturated aqueous sodium bicarbonate solution and then with saturated brine, and dried over anhydrous sodium sulfate. The solvent was evaporated under reduced pressure, and the residue was purified by silica gel column chromatography (n-hexane:ethyl acetate=15:1), to thereby yield 0.20 g of the target compound as colorless transparent oily matter (yield: 39.5%).

$^1$H-NMR (CDCl$_3$, ppm); 0.32~0.46 (4H, m), 1.32 (9H, s), 1.84 (1H, m), 2.60 (3H, s), 3.66 (2H, s), 3.72 (2H, s), 7.11~7.41 (6H, m), 7.81~7.85 (2H, m).

Example 63

Production of N-(4-tert-Butylbenzyl)-N-cyclopropyl-(3-isopropenylbenzyl)amine (Compound 83)

The procedure described in Example 60 was repeated, except that methyl triphenylphosphonium bromide (0.32 g; 8.94×10$^{-1}$ mmol), n-butyl lithium in n-hexane (1.56 M: 0.6 ml; 8.9×10$^{-1}$ mmol), and Compound 82 (0.20 g; 5.96×10$^{-1}$ mmol) were used, to thereby yield 0.07 g of the target compound (yield: 35.2%).

$^1$H-NMR (CDCl$_3$, ppm); 0.32~0.46 (4H, m), 1.32 (9H, s), 1.84 (1H, m), 2.17 (3H, s), 3.66 (2H, s), 3.68 (2H, s), 5.08 (1H, s), 5.37 (1H, s), 7.19~7.37 (8H, m).

Example 64

Production of N-(4-tert-Butylbenzyl)-N-cyclopropyl-(3-isopropenylbenzyl)amine Hydrochloride (Compound 84)

The procedure described in Example 7 was repeated, except that Compound 83 (0.07 g; 2.10×10$^{-1}$ mmol) and 4N hydrochloric acid—ethyl acetate solution (0.05 ml; 2.0×10$^{-1}$ mmol) were used, to thereby yield 0.05 g of the target compound as white crystals (yield: 64.4%).

IR (KBr tablet, cm$^{-1}$); 3424, 2962, 2869, 2680, 2599, 2554, 2424, 2360, 2341, 1456, 1410, 1365, 1038, 893; m. p. 133~136° C.; $^1$H-NMR (CDCl$_3$, ppm); 0.59~0.72 (4H, m), 1.28 (9H, s), 1.44 (1H, m), 2.18 (3H, s), 4.10~4.36 (2H×2, m), 5.16 (1H, s), 5.45 (1H, s), 7.28~7.56 (7H, m), 7.71 (1H, s), 12.5 (1H, brs).

Example 65

Production of N-(4-tert-Butylbenzyl)-N-methyl-(3-bromo-5-methylbenzyl)amine (Compound 85)

The procedure described in Example 58 was repeated, except that N-(3-bromo-5-methylbenzyl)methylamine (1.62 g; 7.57 mmol), sodium carbonate (1.15 g; 10.8 mmol), and 4-tert-butylbenzyl bromide (1.64 g; 7.21 mmol) were used, to thereby yield 1.42 g of the target compound as white oily matter (yield: 54.7%).

$^1$H-NMR (CDCl$_3$, ppm); 1.32 (9H, s), 2.17 (3H s), 2.32 (3H, s), 3.43 (2H, s), 3.49 (2H, s), 7.09 (1H, s), 7.20 (1H, s), 7.27 (2H, d, J=6.48 Hz), 7.32 (1H, s), 7.36 (2H, d, J=6.48 Hz).

Example 66

Production of 2-[3-{N-(4-tert-Butylbenzyl)-N-methylaminomethyl}-5-methylphenyl]-2-propanol (Compound 86)

Compound 85 (1.42 g; 3.94 mmol) was dissolved in tetrahydrofuran (20 ml). While the solution was stirred at −75° C. under nitrogen atmosphere, n-butyl lithium in n-hexane (1.56 M: 2.5 ml; 3.94 mmol) was added dropwise. The mixture was stirred for 15 minutes, and acetone (2 ml) was added dropwise thereto. The resultant mixture was brought to room temperature over 2 hours, and the reaction was stopped by dropwise addition of saturated aqueous ammonium chloride solution, followed by extraction with diethyl ether (100 ml). The organic layer was washed with saturated brine, and dried over sodium sulfate. The solvent was evaporated under reduced pressure, and the residue was purified by silica gel column chromatography (n-hexane:ethyl acetate=10:1→4:1), to thereby yield 0.41 g of the target compound as yellow oily matter (yield: 30.6%).

$^1$H-NMR (CDCl$_3$, ppm); 1.33 (9H, s), 1.58 (3H×2, s), 2.22 (3H, s), 2.36 (3H, s), 3.48 (2H, s), 3.50 (2H, s), 7.08 (1H, s), 7.18 (1H, s), 7.26~7.36 (5H, m).

Example 67

Production of N-(4-tert-Butylbenzyl)-N-methyl-(3-isopropenyl-5-methylbenzyl)amine (Compound 87)

Compound 86 (0.40 g; 1.18 mmol) was dissolved in pyridine (20 ml). While the solution was stirred in an ice bath, phosphorus oxychloride (1.81 g; 11.8 mmol) was added dropwise. After completion of the addition, the mixture was removed from the ice bath, and stirred for 30 minutes at room temperature, followed by heating under reflux for 4 hours. The mixture was brought to room temperature, and poured into ice+saturated aqueous sodium bicarbonate solution. The mixture was neutralized with sodium bicarbonate, and extracted with chloroform (70 ml). The organic layer was washed with saturated aqueous sodium bicarbonate solution and then with saturated brine, and dried over sodium sulfate. The solvent was evaporated under reduced pressure, and the residue was purified by silica gel column chromatography (n-hexane:ethyl acetate= 15:1), to thereby yield 0.12 g of the target compound (yield: 31.6%).

$^1$H-NMR (CDCl$_3$, ppm); 1.31 (9H, s), 2.15 (3H, s), 2.19 (3H, s), 2.35 (3H, s), 3.49 (2H×2, s), 5.06 (1H, s), 5.36 (1H, s), 7.11 (1H, s), 7.16 (1H, s), 7.26~7.60 (5H, m).

Example 68

Production of N-(4-tert-Butylbenzyl)-N-methyl-(3-isopropenyl-5-methylbenzyl)amine hydrochloride (Compound 88)

The procedure described in Example 61 was repeated, except that Compound 87 (0.12 g; 3.73×10$^{-1}$ mmol) and 4N hydrochloric acid—ethyl acetate solution (0.10 ml; 4.00× 10$^{-1}$ mmol) were used, to thereby yield 0.10 g of the target compound as white crystals (yield: 74.9%).

IR (KBr tablet, cm$^{-1}$); 3440, 2962, 2921, 2869, 2694, 2625, 2523, 1601, 1462, 1417, 1365; m. p. 156~159° C.; $^1$H-NMR (CDCl$_3$, ppm); 1.33 (9H, s), 2.17 (3H, s), 2.40 (3H, s), 2.57 (3H, d, J=4.33 Hz), 3.96~4.08 (2H, m), 4.19~4.26 (2H, m), 5.14 (1H, s), 5.44 (1H, s), 7.30~7.55 (7H, m), 12.8 (1H, brs).

Example 69

Production of 2-[3-{N-(4-tert-Butylbenzyl)-N-methylaminomethyl}phenyl]-3-methyl-2-butanol (Compound 89)

Compound 78 (2.00 g; 5.78 mmol) was dissolved in tetrahydrofuran (20 ml). While the solution was stirred at −40° C. under nitrogen atmosphere, n-butyl lithium in n-hexane (1.56 M: 3.7 ml; 5.8 mmol) was added dropwise. After completion of the addition, the mixture was cooled to −75° C., an 3-methyl-2-butanone (2.00 g) in a small amount of tetrahydrofuran was added dropwise thereto. The resultant mixture was gradually brought to room temperature, and the reaction was stopped by dropwise addition of saturated aqueous ammonium chloride solution, followed by extraction with diethyl ether (100 ml). The organic layer was washed with saturated brine, and dried over sodium sulfate. The solvent was evaporated under reduced pressure, and the residue was purified by silica gel column chromatography (n-hexane:ethyl acetate=3:1), to thereby yield 0.86 g of the target compound as brown oily matter (yield: 43.3%).

$^1$H-NMR (CDCl$_3$, ppm); 0.80 (3H, d, J=7.02 Hz), 0.89 (3H, d, J=7.02 Hz), 1.31 (9H, s), 1.53 (3H, s), 2.05 (1H, m), 2.18 (3H, s), 3.47 (2H, s), 3.53 (2H, s), 7.26~7.42 (8H, m).

Example 70

Production Method of N-(4-tert-Butylbenzyl)-N-methyl-[3-(1-isopropylvinyl)benzyl]amine (Compound 90)

Compound 89 (0.30 g; 8.73×10$^{-1}$ mmol) was dissolved in pyridine (20 ml). While the solution was stirred at room temperature, phosphorus oxychloride (1.34 g; 8.73 mmol) was added dropwise. After completion of the addition, the mixture was stirred for 6 hours at 100° C., and left to cool to room temperature. The mixture was poured into ice+ saturated aqueous sodium bicarbonate solution, and extracted with chloroform (100 ml). The organic layer was washed with saturated aqueous sodium bicarbonate solution and then with saturated brine, and dried over sodium sulfate. The solvent was evaporated under reduced pressure, and the residue was purified by silica gel column chromatography (n-hexane:ethyl acetate=10:1), to thereby yield 0.19 g of the target compound as yellow oily matter (yield: 64.9%).

$^1$H-NMR (CDCl$_3$, ppm); 1.10 (3H×2, d, J=6.21 Hz), 1.28 (9H, s), 2.20 (3H, s), 2.84 (1H, m), 3.49 (2H, s), 3.52 (2H, s), 5.03 (1H, s), 5.15 (1H, s), 7.20~7.34 (8H, m).

Example 71

Production Method of N-(4-tert-Butylbenzyl)-N-methyl-[3-(1-isopropylvinyl)benzyl]amine Hydrochloride (Compound 91)

The procedure described in Example 61 was repeated, except that Compound 90 (0.19 g; 5.66×10⁻¹ mmol) and 4N hydrochloric acid (1 eq.)—ethyl acetate solution (0.14 ml) were used, to thereby yield 0.17 g of the target compound as white crystals (yield: 80.7%).

IR (KBr tablet, cm⁻¹); 3436, 2963, 2925, 2906, 2883, 2870, 2674, 2628, 2562, 1471, 1461, 1419, 1405, 889; m. p. 177~179° C.; ¹H-NMR (CDCl₃, ppm); 1.08~1.14 (3H×2, m), 1.33 (9H, s), 2.57 (3H, d, J=4.86 Hz), 2.86 (1H, m), 4.01~4.08 (2H, m), 4.20~4.30 (2H, m), 5.11 (1H, s), 5.21 (1H, s), 7.39~7.65 (8H, m), 12.9 (1H, brs).

Example 72

Production of 1-[3-{N-(4-tert-Butylbenzyl)-N-methylaminomethyl}phenyl]-1-propanol (Compound 92)

Compound 78 (2.00 g; 5.78 mmol) was dissolved in tetrahydrofran (20 ml). While the solution was stirred at −30° C. under nitrogen atmosphere, n-butyl lithium in n-hexane (1.56 M: 3.70 ml; 5.77 mmol) was added dropwise, followed by stirring for 5 minutes. The mixture was cooled to −75° C., and propionaldehyde (1 ml) was slowly added dropwise thereto. The resultant mixture was brought to room temperature over 2 hours, and the reaction was stopped by dropwise addition of saturated aqueous ammonium chloride solution, followed by extraction with diethyl ether (100 ml). The organic layer was washed with saturated brine, and dried over sodium sulfate. The solvent was evaporated under reduced pressure, and the residue was purified by silica gel column chromatography (n-hexane:ethyl acetate=5:1), to thereby yield 1.08 g of the target compound as yellow oily matter (yield: 57.4%).

¹H-NMR (CDCl₃, ppm); 0.92 (3H, t, J=7.02 Hz), 1.31 (9H, s), 1.70~1.89 (2H, m), 2.18 (3H, s), 3.49 (2H, s), 3.52 (2H, s), 4.60 (1H, t, J=6.48 Hz), 7.21~7.35 (8H, m).

Example 73

Production of 3'-[N-(4-tert-Butylbenzyl)-N-methylaminomethyl]propiophenone (Compound 93)

Pyridinium dichromate (2.89 g; 7.68 mmol) was suspended in methylene chloride (30 ml). While the suspension was stirred at room temperature, Compound 92 (0.50 g; 1.54 mmol) in methylene chloride (5 ml) was added dropwise. The mixture was stirred for 4 hours, and diethyl ether (30 ml) and magnesium sulfate (3 g) were added thereto, followed by stirring for 10 minutes. Insoluble matter was filtered off, and the filtrate was concentrated under reduced pressure. The residue was purified by silica gel column chromatography (n-hexane:ethyl acetate=10:1), to thereby yield 0.19 g of the target compound as colorless transparent oily matter (yield: 38.1%).

¹H-NMR (CDCl₃, ppm); 1.23 (3H, t, J=7.02 Hz), 1.31 (9H, s), 2.19 (3H, s), 3.03 (2H, q, J=7.02 Hz), 3.51 (2H, s), 3.56 (2H, s), 7.30~7.44 (5H, m), 7.58 (1H, d, J=7.83 Hz), 7.84 (1H, d, J=7.83 Hz), 7.95 (1H, s).

Example 74

Production of N-(4-tert-Butylbenzyl)-N-methyl-[3-(1-ethylvinyl)benzyl]amine (Compound 94)

Methyl triphenylphosphonium bromide (0.18 g; 4.94×10⁻¹ mmol) was added to benzene (7 ml). While the mixture was stirred under nitrogen atmosphere at room temperature, n-butyl lithium in n-hexane (1.56 M: 0.32 ml; 5.00×10⁻¹ mmol) was added dropwise. The mixture was stirred for 5 minutes, and Compound 19 (0.08 g; 2.47×10⁻¹ mmol) in benzene (5 ml) was added dropwise thereto, followed by heating under reflux for 2 hours. The mixture was brought to room temperature, and the reaction was stopped by pouring the mixture into ice/water, followed by extraction with benzene (100 ml). The organic layer was washed with saturated brine, and dried over anhydrous sodium sulfate. The solvent was evaporated under reduced pressure, and the residue was purified by silica gel column chromatography (n-hexane:ethyl acetate=10:1), to thereby yield 0.05 g of the target compound as colorless transparent oily matter (yield: 63%).

¹H-NMR (CDCl₃, ppm); 1.11 (3H, t, J=7.56 Hz), 1.31 (9H, s), 2.20 (3H, s), 2.53 (2H, q, J=7.56 Hz), 3.50 (2H, s), 3.52 (2H, s), 5.06 (1H, s) 5.29 (1H, s), 7.26~7.36 (7H, m), 7.41 (1H, s).

Example 75

Production of N-(4-tert-Butylbenzyl)-N-methyl-[3-(1-ethylvinyl)benzyl]amine Hydrochloride (Compound 95)

The procedure described in Example 61 was repeated, except that Compound 94 (0.09 g; 2.80×10⁻¹ mmol) and 4N hydrochloric acid (1 eq.)—ethyl acetate solution (0.07 ml) were used, to thereby yield 0.07 g of the target compound as white crystals (yield: 69.8%).

IR (KBr tablet, cm⁻¹); 2964, 2904, 2886, 2689, 2677, 2632, 1464; m. p. 177~181° C.; ¹H-NMR (CDCl₃, ppm); 1.11 (3H, t, J=7.29 Hz), 1.33 (9H, s), 1.57 (3H, s), 2.55 (2H, q, J=7.29 Hz), 4.03–4.07 (2H, m), 4.22~4.25 (2H, m), 5.14 (1H, s), 5.37 (1H, s), 7.39~7.57 (7H, m), 7.64 (1H, s).

Example 76

Production of cis-N-(4-tert-Butylbenzyl)-N-methyl-[3-(1-methyl-1-propenyl)benzyl]amine (Compound 96)

Ethyl triphenylphosphonium bromide (1.58 g; 4.26 mmol) was added to benzene (20 ml). While the mixture was stirred under nitrogen atmosphere at room temperature, n-butyl lithium in n-hexane (1.56 M: 2.7 ml; 4.21 mmol) was added dropwise. The mixture was stirred for 5 minutes, and Compound 1 (0.88 g; 2.84 mmol) in benzene (10 ml) was added dropwise thereto, followed by heating under reflux for 3 hours. The mixture was brought to room temperature, and the reaction was stopped by pouring the mixture into ice/water, followed by extraction with benzene (100 ml). The organic layer was washed with saturated brine, and dried over anhydrous sodium sulfate. The solvent was evaporated under reduced pressure, and the residue was purified by silica gel column chromatography (n-hexane:ethyl acetate=40:1), to thereby yield 0.11 g of the target compound (yield: 12.0%).

¹H-NMR (CDCl₃, ppm); 1.31 (9H, s), 1.60 (3H, dq, J=7.02 Hz, 1.49 Hz), 2.03 (3H, q, J=1.49 Hz), 2.20 (3H, s), 3.50 (2H, s), 3.52 (2H, s), 5.56 (1H, m), 7.08 (1H, m), 7.20~7.35 (7H, m).

Example 77

Production of cis-N-(4-tert-Butylbenzyl)-N-methyl-[3-(1-methyl-1-propenyl)benzyl]amine Hydrochloride (Compound 97)

The procedure described in Example 61 was repeated, except that Compound 96 (0.11 g; 3.41×10⁻¹ mmol) and 4N hydrochloric acid (1 eq.)—ethyl acetate solution (0.08 ml) were used, to thereby yield 0.09 g of the target compound as white crystals (yield: 73.6%).

IR (KBr tablet, cm$^{-1}$); 3458, 2962, 2937, 2917, 2889, 2694, 2677, 2633, 2566, 2548, 1461; m. p. 185~187° C.; $^1$H-NMR (CDCl$_3$, ppm); 1.32 (9H, s), 1.58 (3H, d, J=7.02 Hz), 2.04 (3H, s), 2.57 (3H, d, J=7.83 Hz), 4.00~4.09 (2H, m), 4.21~4.30 (2H, m), 5.61 (1H, m), 7.26~7.65 (8H, m), 12.8 (1H, brs).

Example 78

Production of N-(4-tert-Butylbenzyl)-N-methyl-(3-fluoro-5-isopropenylbenzyl)amine Hydrochloride (Compound 101)

The procedure described in Example 55 was repeated, except that 3-bromo-5-fluorobenzyl bromide was reacted with N-(4-tert-butylbenzyl)methylamine, to thereby yield N-(4-tert-butylbenzyl)-N-methyl-(3-bromo-5-fluorobenzyl) amine (Compound 98). Subsequently, the procedure described in Example 66 was repeated, except that Compound 98 was used as a starting compound, to thereby yield 2-[3-{N-(4-tert-butylbenzyl)-N-methylaminomethyl}-5-fluorophenyl]-2-butanol (Compound 99). Subsequently, the procedure described in Example 67 was repeated, except that Compound 99 was used as a starting compound, to thereby yield N-(4-tert-butylbenzyl)-N-methyl-(3-fluoro-5-isopropenylbenzyl)amine (Compound 100). Subsequently, the procedure described in Example 57 was repeated, except that Compound 100 was used as a starting compound, to thereby yield Compound 101.

m. p. 181~183.5° C.; $^1$H-NMR (CDCl$_3$, ppm); 1.33 (9H, s), 2.17 (3H, s), 2.60 (3H, d, J=4.86 Hz), 4.00 (1H, dd, J=12.96 Hz, 5.94 Hz), 4.11 (1H, dd, J=13.23 Hz, 4.86 Hz), 4.20~4.30 (2H, m), 5.22 (1H, s), 5.53 (1H, s), 7.19~7.29 (2H, m), 7.47 (2H, d, J=8.37 Hz), 7.53 (2H, d, J=8.37 Hz), 7.70 (1H, brs), 13.04 (1H, brs).

Referential Example 20

Production of 4-(1-Methyl-1-phenylethyl) benzaldehyde 2,2-Diphenylpropane (3.93 g; 20.0 mmol) and hexamethylenetetramine (2.80 g; 20.0 mmol) were added to trifluoroacetic acid (35 ml), and the mixture was refluxed for 16 hours. The mixture was brought to room temperature, and poured into ice/water, followed by stirring for 1 hour. The pH of the mixture was adjusted to about 9 with potassium carbonate, followed by extraction with ether (100 ml). The organic layer was washed with saturated aqueous sodium bicarbonate solution, and dried over anhydrous sodium sulfate. The solvent was evaporated under reduced pressure, and the residue was purified by silica gel column chromatography (n-hexane:ethyl acetate=10:1), to thereby yield 3.61 g of the target compound (yield: 80.5%).

$^1$H-NMR (CDCl$_3$, ppm); 1.71 (6H, s), 7.17~7.32 (5H, m), 7.40 (2H, d, J=8.37 Hz), 7.79 (2H, d, J=8.37 Hz), 9.98 (1H, s).

Referential Example 21

Production of N-[4-(1-Methyl-1-phenylethyl) benzyl]-methylamine 4-(1-Methyl-1-phenylethyl)benzaldehyde (3.61 g; 16.1 mmol) and molecular sieves (4 angstroms: about five granules) were added to 40% methylamine in methanol (40 ml), and the mixture was stirred overnight at room temperature. The reaction mixture was filtered, and the filtrate was concentrated under reduced pressure. The residue was taken up in ether (100 ml), and the organic layer was washed with saturated brine, followed by drying over anhydrous sodium sulfate. The solvent was evaporated under reduced pressure, and the residue was dissolved in methanol (25 ml). Sodium borohydride (0.70 g) was added to the solution, and the thus-obtained mixture was heated for 1 hour at 50° C. The solvent was evaporated under reduced pressure, and the residue was taken up in ether (100 ml). The organic layer was washed with saturated brine, and dried over anhydrous sodium sulfate. The solvent was evaporated under reduced pressure, and the residue was dissolved in ethanol (10 ml). Excess amount of 4N hydrochloric acid—ethyl acetate was added to the solution, and the solvent was evaporated under reduced pressure. The residue was taken up in isopropyl ether (100 ml), and white crystals that precipitated were collected by filtration. The crystals were converted into their free forms by use of aqueous sodium hydroxide solution, followed by extraction with ether. The organic layer was dried over anhydrous sodium sulfate, and the solvent was evaporated under reduced pressure, to thereby yield 2.49 g of the target compound as orange oily matter (yield: 64.6%).

$^1$H-NMR (CDCl$_3$, ppm); 1.68 (6H, s), 2.46 (3H, s), 3.71 (2H, s), 7.08~7.29 (9H, m), Example 79

Production of 3'-[N-4-(1-Methyl-1-phenylethyl) benzyl-N-methylaminomethyl]acetophenone (Compound 102)

N-[4-(1-methyl-1-phenylethyl)benzyl]methylamine (1.00 g; 4.18 mmol) and sodium carbonate (0.63 g; 5.97 mmol) were added to N,N-dimethylformamide (20 ml). While the mixture was stirred at room temperature, 3'-bromomethylacetophenone (0.85 g; 3.98 mmol) in N,N-dimethylformamide (5 ml) was added dropwise. The mixture was stirred for 1 hour at room temperature, and the reaction was stopped by pouring the mixture into ice+saturated aqueous sodium bicarbonate solution, followed by extraction with ethyl acetate (100 ml). The organic layer was washed with saturated aqueous sodium bicarbonate solution and then with saturated brine, and dried over anhydrous sodium sulfate. The solvent was evaporated under reduced pressure, and the residue was purified by silica gel column chromatography (n-hexane:ethyl acetate=10:1), to thereby yield 1.16 g of the target compound as whitish-yellow oily matter (yield: 78.5%).

$^1$H-NMR (CDCl$_3$, ppm); 1.68 (4H, s), 2.19 (3H, s), 2.60 (3H, s), 3.50 (2H, s), 3.56 (2H, s), 7.14~7.29 (9H, m), 7.41 (1H, t, J=7.29 Hz), 7.59 (1H, d, J=7.29 Hz), 7.83 (1H, d, J=7.29 Hz), 7.93 (1H, s).

Example 80

Production of N-Methyl-N-[4-(1-methyl-1-phenylethyl)benzyl]-(3-isopropenylbenzyl)amine (Compound 103)

Methyl triphenyl phosphonium bromide (1.67 g; 4.68 mmol) was added to benzene (20 ml). While the mixture was stirred under nitrogen atmosphere at room temperature, n-butyl lithium in n-hexane (1.63 M: 2.9 ml; 4.73 mmol) was added dropwise. The mixture was stirred for 5 minutes, and Compound 28 (1.16 g; 3.12 mmol) in benzene (5 ml) was added dropwise thereto, followed by stirring overnight at room temperature. Reaction was stopped by pouring the mixture into ice/water, followed by extraction with benzene (100 ml).

The organic layer was washed with saturated brine, and dried over anhydrous sodium sulfate. The solvent was evaporated under reduced pressure, and the residue was purified by a gel column chromatography (n-hexane:ethyl acetate=20:1), to thereby yield 0.44 g of the target compound as colorless transparent oily matter (yield: 38.2%).

$^1$H-NMR (CDCl$_3$, ppm); 1.67 (4H, s), 2.16 (3H, s), 2.19 (3H, s), 3.48 (2H, s), 3.52 (2H, s), 5.07 (1H, s), 5.37 (1H, s), 7.14~7.36 (12H, m), 7.36 (1H, s).

Example 81

Production of N-Methyl-N-[4-(1-methyl-1-phenylethyl)benzyl]-(3-isopropenylbenzyl)amine Hydrochloride (Compound 104)

The procedure described in Example 57 was repeated, except that Compound 103 (as a starting compound) (0.44 g; 1.19 mmol) and 4N hydrochloric acid—ethyl acetate solution 0.30 ml; 1.2 mmol) were used, to thereby yield the hydrochloride salt. The thus-obtained hydrochloride salt was recrystallized from a mixture of isopropyl ether and ethanol, thereby yield 0.34 g of the target compound as white crystals (yield: 70.4%).

IR (KBr tablet, cm$^{-1}$); 3445, 2972, 2942, 2669, 2625, 2560, 2539, 1462, 798, 700; m. p. 168~170° C.; $^1$H-NMR (CDCl$_3$, ppm); 1.69 (4H, s), 2.18 (3H, s), 2.58 (3H, d, J=4.32 Hz), 3.98~4.08 (2H, m), 4.19~4.29 (2H, m), 5.16 (1H, s), 5.46 (1H, s), 7.16~7.55 (12H, m), 7.73 (1H, s), 12.9 (1H, brs).

Example 82

Production of N-(4-tert-Butylbenzyl)-N-methyl-(2-isopropenylbenzyl)amine Hydrochloride (Compound 108)

The procedure described in Referential Example 2 was repeated, except that o-bromotoluene was used as a starting compound, to thereby yield 2-bromobenzyl bromide. Subsequently, the procedure described in Example 55 was repeated, except that 2-bromobenzyl bromide was reacted with N-(4-tert-butylbenzyl)methylamine, to thereby yield N-(4-tert-butylbenzyl)-N-methyl-(2-bromobenzyl)amine (Compound 105). Subsequently, the procedure described in Example 56 was repeated, except that Compound 105 was used as a starting compound, to thereby yield 2-[3-{N-(4-tert-butylbenzyl)-N-methylaminomethyl}phenyl]-2-propanol (Compound 106). Subsequently, the procedure described in Example 57 was repeated, except that Compound 106 was used as a starting compound, to thereby yield N-(4-tert-butylbenzyl)-N-methyl-(2-isopropenylbenzyl)amine (Compound 107). As a final step, the procedure described in Example 57 was repeated, except that Compound 107 was used as a starting compound, to thereby yield the target compound.

m. p.: The thus-obtained compound became highly viscous at 60–75° C., and liquefied at 130° C.

$^1$H-NMR (CDCl$_3$, ppm); 1.32 (9H, s), 1.98 (3H, s), 2.52 (3H, d, J=4.86 Hz), 4.06 (1H, dd, J=12.69 Hz, 5.40 Hz), 4.15~4.27 (2H, m), 4.33 (1H, dd, J=13.23 Hz, 4.86 Hz), 4.80 (1H, s), 5.26 (1H, s), 7.20 (1H, dd, J=7.56 Hz, 1.62 Hz), 7.30~7.45 (2H, m), 7.44 (2H, d, J=8.64 Hz), 7.52 (2H, d, J=8.64 Hz), 8.21 (1H, dd, J=7.56 Hz, 1.62 Hz), 12.52 (1H, brs).

Example 83

Production of N-(4-tert-Butylbenzyl)-N-isopropyl-(3-isopropenylbenzyl)amine Hydrochloride (Compound 111)

The procedure described in Referential Example 4 was repeated, except that 3'-bromomethylacetophenone (as a starting compound) and isopropylamine (instead of 40% methylamine in methanol) were used, to thereby yield 3'-(N-isopropylaminomethyl)acetophenone. Subsequently, the procedure described in Example 58 was repeated, except that 3'-(N-isopropylaminomethyl)acetophenone was reacted with 4-tert-butylbenzyl bromide, to thereby yield 3'-[N-(4-tert-butylbenzyl)-N-isopropylaminomethyl]acetophenone (Compound 109). Subsequently, the procedure described in Example 56 was repeated, except that Compound 109 was used as a starting compound, to thereby yield N-(4-tert-butylbenzyl)-N-isopropyl-(3-isopropenylbenzyl)amine (Compound 110). Subsequently, the procedure described in Example 57 was repeated, except that Compound 110 was used as a starting compound, to thereby yield Compound 111 as colorless transparent amorphous matter.

$^1$H-NMR (CDCl$_3$, ppm); 1.30 (9H, s), 1.48 (3H, d, J=7.56 Hz), 1.51 (3H, d, J=7.56 Hz), 2.18 (3H, s), 3.58 (1H, m), 3.91~4.10 (2H, m), 4.11~4.21 (2H, m), 5.14 (1H, s), 5.49 (1H, s), 7.36 (1H, t, J=7.83 Hz), 7.42 (2H, d, J=8.37 Hz), 7.49 (1H, d, J=7.83 Hz), 7.68 (1H, m), 7.70 (2H, d, J=8.37 Hz), 7.95 (1H, s), 12.50 (1H, brs).

Example 84

Production of N-(4-tert-Butylbenzyl)-N-ethyl-(3-isopropenylbenzyl)amine Hydrochloride (Compound 114)

The procedure described in Referential Example 4 was repeated, except that 3'-bromomethylacetophenone (as a starting compound) and ethylamine hydrochloride (instead of 40% methylamine in methanol) were used in the presence of sodium hydroxide, to thereby yield 3'-(N-ethylaminomethyl)acetophenone. Subsequently, the procedure described in Example 58 was repeated, except that 3'-(N-ethylaminomethyl)acetophenone was reacted with 4-tert-butylbenzyl bromide, to thereby yield 3'-[N-(4-tert-butylbenzyl)-N-ethylaminomethyl]acetophenone (Compound 112). Subsequently, the procedure described in Example 56 was repeated, except that Compound 112 was used as a starting compound, to thereby yield N-(4-tert-butylbenzyl)-N-ethyl-(3-isopropenylbenzyl)amine (Compound 113). Subsequently, the procedure described in Example 57 was repeated, except that Compound 113 was used as a starting compound, to thereby yield Compound 114.

m. p. 122~126° C.; $^1$H-NMR (CDCl$_3$, ppm); 1.32 (9H, s), 1.51 (3H, t, J=7.29 Hz), 2.19 (3H, s), 3.01 (2H, m), 4.02~4.16 (2H m), 4.18~4.30 (2H, m), 5.16 (1H, s), 5.48 (1H, s), 7.41 (1H, t, J=7.70 Hz), 7.46 (2H, d, J=8.10 Hz), 7.50~7.65 (2H, m), 7.57 (2H, d, J=8.10 Hz), 7.80 (1H, s), 12.62 (1H, brs).

Example 85

Production of N-(4-tert-Butylbenzyl)-N-methyl-(3-isopropenyl-2-methylbenzyl)amine Hydrochloride (Compound 117)

The procedure described in Referential Example 5 was repeated, except that 3-bromo-o-xylene was used as a starting compound, to thereby yield 3-bromo-2-methylbenzyl bromide and a byproduct, 2-bromo-6-methylbenzyl bromide. The procedure described in Referential Example 6 was repeated, except that the thus-obtained unpurified product was used as starting material, to thereby yield N-(3-bromo-2-methylbenzyl)methylamine. The purification procedure also yielded N-(2-bromo-6-methylbenzyl)methylamine as a byproduct. Subsequently, the procedure described in Example 58 was repeated, except that N-(3-bromo-2-methylbenzyl)methylamine was reacted with 4-tert-butylbenzyl bromide, to thereby yield N-(4-tert-butylbenzyl)-N-methyl-(3-bromo-2-methylbenzyl)amine (Compound 115). Subsequently, the procedure described in Example 66 was repeated, except that Compound 115 was used as a starting compound, to thereby yield 2-[3-{N-(4-tert-butylbenzyl)-N-methylaminomethyl}-2-methylphenyl]-2-propanol (Compound 116). Subsequently, the procedure described in Example 57 was repeated, except that Compound 116 was used as a starting compound, to thereby yield N-(4-tert-butylbenzyl)-N-methyl-(3-isopropenyl-2-methylbenzyl)amine (Compound 117). As a final step, the procedure described in Example 57 was repeated, except that Compound 117 was used as a starting compound, to thereby yield Compound 118.

m. p. 207.5~210.5° C.; $^1$H-NMR (CDCl$_3$, ppm); 1.33 (9H, s), 2.00 (3H, s), 2.28 (3H, s), 2.63 (3H, d, J=5.13 Hz), 4.01 (1H, dd, J=12.83 Hz, 7.43 Hz), 4.15~4.38 (3H, m), 4.82 (1H, s), 5.21 (1H, s), 7.17 (1H, dd, J=7.56 Hz, 1.08 Hz), 7.25 (1H, t, 7.56 Hz), 7.47 (2H, d, J=8.37 Hz), 7.57 (2H, d, J=8.37 Hz), 7.63 (1H, dd, J=7.56 Hz, 1.08 Hz), 12.40 (1H, brs).

Example 86

Production of N-(4-tert-Butylbenzyl)-N-methyl-(2-isopropenyl-6-methylbenzyl)amine Hydrochloride (Compound 122)

The procedure described in Example 58 was repeated, except that N-(2-bromo-6-methylbenzyl)methylamine obtained in an intermediate step of Example 85 was reacted with 4-tert-butylbenzyl bromide, to thereby yield N-(4-tert-butylbenzyl)-N-methyl-(2-bromo-6-methylbenzyl)amine (Compound 119). Subsequently, the procedure described in Example 66 was repeated, except that Compound 119 was used as a starting compound, to thereby yield 2-[2-{N-(4-tert-butylbenzyl)-N-methylaminomethyl}-3-methylphenyl]-2-propanol (Compound 120). Subsequently, the procedure described in Example 67 was repeated, except that Compound 120 was used as a starting compound, to thereby yield N-(4-tert-butylbenzyl)-N-methyl-(2-isopropenyl-6-methylbenzyl)amine (compound 121). As a final step, the procedure described in Example 3 was repeated, except that Compound 121 was used as a starting compound, to thereby yield Compound 122.

m. p. 166~167.5° C.; $^1$H-NMR (CDCl$_3$, ppm); 1.34 (9H, s), 1.93 (3H, s), 2.50 (3H, s), 2.57 (3H, d, J=4.59 Hz), 3.99 (1H, dd, J=12.96 Hz, 6.48 Hz), 4.16 (1H, m), 4.25 (1H, m), 4.61 (1H, m), 4.82 (1H, s), 5.21 (1H, s), 7.00 (1H, d, J=7.29 Hz), 7.16 (1H, d, J=7.29 Hz), 7.25 (1H, t, 7.29 Hz), 7.50 (2H, d, J=8.37 Hz), 7.68 (2H, d, J=8.37 Hz), 11.33 (1H, brs).

Example 87

Production of N-(4-tert-Butylbenzyl)-N-methyl-(3-isopropenyl-4-methylbenzyl)amine Hydrochloride (Compound 126)

The procedure described in Referential Example 16 was repeated, except that 3-bromo-4-methylbenzoic acid was used as a starting compound, to thereby yield 3-bromo-4-methylbenzyl alcohol. Subsequently, the procedure described in Referential Example 17 was repeated, except that 3-bromo-4-methylbenzyl alcohol was used as a starting compound, to thereby yield 3-bromo-4-methylbenzyl bromide. Subsequently, the procedure described in Referential Example 18 was repeated, except that 3-bromo-4-methylbenzyl bromide was used as a starting compound, to thereby yield N-(3-bromo-4-methylbenzyl)methylamine. Subsequently, the procedure described in Example 58 was repeated, except that N-(3-bromo-4-methylbenzyl)methylamine was reacted with 4-tert-butylbenzyl bromide, to thereby yield N-(4-tert-butylbenzyl)-N-methyl-(3-bromo-4-methylbenzyl)amine (Compound 123). The procedure described in Example 66 was repeated, except that Compound 123 was used as a starting compound, to thereby yield 2-[5-{N-(4-tert-butylbenzyl)-N-methylaminomethyl}-2-methylphenyl]-2-propanol (Compound 124). Subsequently, the procedure described in Example 67 was repeated, except that Compound 124 was used as a starting compound, to thereby yield N-(4-tert-butylbenzyl)-N-methyl-(3-isopropenyl-4-methylbenzyl)amine (Compound 125). As a final step, the procedure described in Example 57 was repeated, except that Compound 125 was used as a starting compound, to thereby yield Compound 126.

m. p. 175~177° C.; $^1$H-NMR (CDCl$_3$, ppm); 1.32 (9H, s), 2.05 (3H, s), 2.33 (3H, s), 2.56 (3H, brs), 3.95~4.08 (2H, m), 4.17~4.28 (2H, m), 4.86 (1H, s), 5.23 (1H, s), 7.20~7.30 (2H, m), 7.46 (2H, d, J=8.37 Hz), 7.42~7.52 (1H, m). 7.53 (2H, d, J=8.37 Hz), 12.72 (1H, brs).

Example 88

Production of N-(4-tert-Butylbenzyl)-N-methyl-(4-fluoro-3-isopropenylbenzyl)amine Hydrochloride (Compound 130)

The procedure described in Referential Example 19 was repeated, except that 3-bromo-4-fluorotoluene was used as a starting compound, to thereby yield 3-bromo-4-fluorobenzyl bromide. Subsequently, the procedure described in Referential Example 18 was repeated, except that 3-bromo-4-fluorobenzyl bromide was used as a starting compound, to thereby yield N-(3-bromo-4-fluorobenzyl)methylamine. Subsequently, the procedure described in Example 58 was repeated, except that N-(3-bromo-4-fluorobenzyl)methylamine was reacted with 4-tert-butylbenzyl bromide, to thereby yield N-(4-tert-butylbenzyl)-N-methyl-(3-bromo-4-fluorobenzyl)amine (Compound 127). Subsequently, the procedure described in Example 66 was repeated, except that Compound 127 was used as a starting compound, to thereby yield 2-[5-{N-(4-tert-butylbenzyl)-N-methylaminomethyl}-2-fluorophenyl]-2-propanol (Compound 128). Subsequently, the procedure described in Example 67 was repeated, except that Compound 128 was used as a starting compound, to thereby yield N-(4-tert-butylbenzyl)-N-methyl-(4-fluoro-3-isopropenylbenzyl)amine (Compound 129). As a final step, the procedure described in Example 57 was repeated, except that Compound 129 was used as a starting compound, to thereby yield Compound 130.

m. p. 209~212° C.; $^1$H-NMR (CDCl$_3$, ppm); 1.33 (9H, s), 2.17 (3H, s), 2.58 (3H, d, J=4.86 Hz), 3.98 (1H, dd, J=13.23 Hz, 5.94 Hz), 4.07 (1H, dd, J=13.23 Hz, 5.40 Hz), 4.24 (1H, dd, J=13.23 Hz, 4.05 Hz) 4.26 (1H, dd, J=13.23 Hz, 4.05 Hz), 5.29 (1H, s), 5.32 (1H, s) 7.12 (1H, dd, J=9.45 Hz, 8.37 Hz), 7.47 (2H, d, J=8.64 Hz), 7.53 (2H, d, J=8.64 Hz), 7.58~7.66 (2H, m), 12.87 (1H, brs).

Example 89

Production of N-(4-tert-Butylbenzyl)-N-methyl-(2-fluoro-5-isopropenylbenzyl)amine Hydrochloride (Compound 134)

The procedure described in Referential Example 19 was repeated, except that 5-bromo-2-fluorotoluene was used as a starting compound, to thereby yield 5-bromo-2-fluorobenzyl bromide. Subsequently, the procedure described in Referential Example 18 was repeated, except that 5-bromo-2-fluorobenzyl bromide was used as a starting compound, to thereby yield N-(5-bromo-2-fluorobenzyl)methylamine. Subsequently, the procedure described in Example 58 was repeated, except that N-(5-bromo-2-fluorobenzyl)methylamine was reacted with 4-tert-butylbenzyl bromide, to thereby yield N-(4-tert-butylbenzyl)-N-methyl-(5-bromo-2-fluorobenzyl)amine (Compound 131). Subsequently, the procedure described in Example 66 was repeated, except that Compound 131 was used as a starting compound, to thereby yield 2-[3-{N-(4-tert-butylbenzyl)-N-methylaminomethyl}-4-fluorophenyl]-2-propanol (Compound 132). Subsequently, the procedure described in Example 67 was repeated, except that Compound 132 was used as a starting compound, to thereby yield N-(4-tert-butylbenzyl)-N-methyl-(2-fluoro-5-isopropenylbenzyl)amine (Compound 133). As a final step, the procedure described in Example 57 was repeated, except that Compound 133 was used as a starting compound, to thereby yield Compound 134.

m. p. 171.5~173° C.; $^1$H-NMR (CDCl$_3$, ppm); 1.32 (9H, s), 2.19 (3H, s), 2.59 (3H, d, J=4.59 Hz), 4.03 (1H, dd, J=12.96 Hz, 5.67 Hz), 4.21 (1H, dd, J=13.23 Hz, 5.67 Hz), 4.25~4.35 (2H, m), 5.16 (1H, s), 5.49 (1H, s), 7.09 (1H, t, J=9.18 Hz), 7.47 (2H, d, J=8.64 Hz), 7.54 (1H, m) 7.56 (2H, d, J=8.64 Hz), 8.12 (1H, dd, J=7.56 Hz, 2.43 Hz), 12.95 (1H, brs).

Example 90

Production of N-(3-Bromo-5-methylbenzyl)-N-methyl-[4-(1-methyl-1-phenylethyl)benzyl]amine (Compound 135)

N-(3-bromo-5-methylbenzyl)methylamine hydrochloride (11.0 g) was dissolved in methanol (30 ml), and potassium hydroxide (800 mg) was added thereto. The mixture was stirred until complete dissolution was effected, and 4-(1-methyl-1-phenylethyl)benzaldehyde (8.96 g) was added thereto. The mixture was stirred for 15 minutes, and sodium cyanoborohydride (950 mg) in methanol (10 ml) was added dropwise. The mixture was stirred for 30 minutes, and insoluble matter was filtered off, followed by washing with methanol. The filtrate was concentrated under reduced pressure, and water was added thereto, followed by extraction with ether (250 ml). 1N Hydrochloric acid (150 ml) was added to the organic layer, and the mixture was stirred. Crystals that precipitated were collected by filtration, and washed with water and then with ether. The filtrate was separated, and the aqueous layer was combined with the above crystals. The mixture was alkalinized with sodium hydroxide, and extracted with chloroform (250 ml), followed by drying over magnesium sulfate. The solvent was evaporated under reduced pressure, and the residue was purified by silica gel column chromatography (n-hexane:ethyl acetate=30:1), to thereby yield 7.60 g of the target compound (yield: 45.0%).

$^1$H-NMR (CDCl$_3$, ppm); 1.68 (6H, s), 2.16 (3H, s), 2.31 (3H, s), 3.42 (2H, s), 3.47 (2H, s), 7.08 (1H, s), 7.10~7.29 (10H, m), 7.31 (1H, s),

Example 91

Production of N-Methyl-N-[4-(1-methyl-1-phenylethyl)benzyl]-(3-isopropenyl-5-methylbenzyl) amine Hydrochloride (Compound 138)

The procedure described in Example 66 was repeated, except that Compound 135 was used as a starting compound, to thereby yield 2-[3-methyl-5-[N-methyl-N-{4-(1-methyl-1-phenylethyl)benzyl}aminomethyl]phenyl]-2-propanol (Compound 136). Subsequently, the procedure described in Example 67 was repeated, except that Compound 136 was used as a starting compound, to thereby yield N-methyl-N-[4-(1-methyl-1-phenylethyl)benzyl]-(3-isopropenyl-5-methylbenzyl)amine (Compound 137). As a final step, the procedure described in Example 57 was repeated, except that Compound 137 was used as a starting compound, to thereby yield Compound 138.

m. p. 153~156° C.; $^1$H-NMR (CDCl$_3$, ppm); 1.69 (6H, s), 2.16 (3H, s), 2.40 (3H, s), 2.57 (3H, d, J=4.32 Hz), 3.95~4.07 (2H, m), 4.16~4.27 (2H, m), 5.13 (1H, s), 5.43 (1H, s), 7.14~7.36 (9H, m), 7.47~7.55 (3H, m), 12.82 (1H, brs).

Referential Example 22

Production of 3,5-Dibromobenzyl Bromide 3,5-Dibromotoluene (27.0 g; 108.0 mmol), N-bromosuccinimide (19.2 g; 108.0 mmol), and benzoyl peroxide (0.32 g) were added to benzene (200 ml), and the mixture was refluxed for 2.5 hours. The mixture was brought to room temperature, and the solvent was evaporated under reduced pressure. The residue was taken up in n-hexane (200 ml), and the mixture was left to stand overnight at room temperature. Crystals that precipitated were filtered off, and the filtrate was concentrated under reduced pressure, to thereby yield 17.2 g of the target compound (yield: 48.3%).

$^1$H-NMR (CDCl$_3$, ppm); 4.36 (2H, s), 7.47 (2H, d, J=1.62 Hz), 7.60 (1H, t, J=1.62 Hz).

Referential Example 23

Production of N-(3,5-Dibromobenzyl)methylamine

Triethylamine (5.28 g; 52.2 mmol) was dissolved in 40% methylamine in methanol (100 ml). While the mixture was stirred at room temperature, 3,5-dibromobenzyl bromide (17.2 g; 52.2 mmol) in N,N-dimethylformamide (20 ml) was added dropwise. The mixture was stirred overnight at room temperature, and the solvent was evaporated under reduced pressure. The residue was taken up in 2N hydrochloric acid (150 ml), and the mixture was extracted with diethyl ether (150 ml), to thereby exclude impurities. The aqueous layer was alkalinized with aqueous sodium hydroxide solution, and extracted with chloroform (100 ml). The organic layer was washed with saturated aqueous sodium bicarbonate solution and then with saturated brine, and dried over sodium sulfate. The solvent was evaporated under reduced pressure, to thereby yield 11.3 g of the target compound as orange oily matter (yield: 77.7%).

$^1$H-NMR (CDCl$_3$, ppm); 2.43 (3H, s), 3.70 (2H, s), 7.42 (2H, s), 7.55 (1H, s).

Example 92

Production of N-(4-tert-Butylbenzyl)-N-methyl-(3,5-dibromobenzyl)amine (Compound 139)

N-(3,5-dibromobenzyl)methylamine (4.38 g; 15.7 mmol) and sodium carbonate (2.37 g; 22.4 mmol) were added to N,N-dimethylformamide (40 ml). While the mixture was stirred at room temperature, p-tert-butylbenzyl bromide (3.40 g; 14.9 mmol) in N,N-dimethylformamide (20 ml) was added dropwise. After completion of the addition, the mixture was stirred for 100 minutes at 50° C., and left to cool to room temperature. The mixture was poured into ice+saturated aqueous sodium bicarbonate solution, followed by extraction with diethyl ether (100 ml). The organic layer was washed with saturated aqueous sodium bicarbonate solution, and extracted with 2N hydrochloric acid twice (100 ml each). Crystals that precipitated were collected, and combined with the aqueous layer. The mixture was alkalinized with aqueous sodium hydroxide solution, and extracted with chloroform (100 ml). The organic layer was washed with water and then with saturated brine, and dried over sodium sulfate. The solvent was evaporated under reduced pressure, and the residue was purified by silica gel column chromatography (n-hexane:ethyl acetate=40:1), to thereby yield 4.21 g of the target compound as pale white oily matter (yield: 66.4%).

$^1$H-NMR (CDCl$_3$, ppm); 1.30 (9H, s), 2.18 (3H, s), 3.43 (2H, s), 3.50 (2H, s), 7.26 (2H, d, J=7.83 Hz), 7.36 (2H, d, J=7.83 Hz), 7.53 (2H, s), 7.56 (1H, s).

Example 93

Production of 2-[3-Bromo-5-{N-(4-tert-Butylbenzyl)-N-methylaminomethyl}phenyl]-2-propanol (Compound 140)

Compound 139 (4.21 g; 9.90 mmol) was dissolved in tetrahydrofuran (40 ml). While the solution was stirred at −78° C. under nitrogen atmosphere, n-butyl lithium in n-hexane (1.63 M: 6.1 ml; 9.94 mmol) was added dropwise. After 10 minutes, acetone (1.5 ml) was added dropwise thereto, and the mixture was gradually brought to room temperature. Saturated aqueous ammonium chloride solution was added dropwise to the mixture, and water was added thereto, followed by extraction with diethyl ether (100 ml). The organic layer was washed with saturated brine, and dried over sodium sulfate. The solvent was evaporated under reduced pressure, and the residue was purified by silica gel column chromatography (n-hexane:ethyl acetate=5:1→2:1), to thereby yield 3.11 g of the target compound as pale yellow oily matter (yield: 77.7%).

$^1$H-NMR (CDCl$_3$, ppm); 1.32 (9H, s), 1.57 (3H×2, s), 2.19 (3H, s), 3.48 (2H×2, s), 7.27 (2H, d, J=8.37 Hz), 7.35 (2H, d, J=8.37 Hz), 7.39 (1H, s), 7.42 (1H, s), 7.51 (1H, s).

Example 94

Production of N-(4-tert-Butylbenzyl)-N-methyl-(3-bromo-5-isopropenylbenzyl)amine (Compound 141)

Compound 140 (3.11 g; 7.69 mmol) was dissolved in pyridine (50 ml). While the solution was stirred at room temperature, phosphorus oxychloride (11.8 g; 76.9 mmol) was added dropwise. After completion of the addition, the mixture was stirred for 3 hours at 120° C. The mixture was brought to room temperature, and poured into ice/water. The mixture was alkalinized with sodium hydroxide, and extracted with chloroform (150 ml). The organic layer was washed with saturated aqueous sodium bicarbonate solution and then with saturated brine, and dried over sodium sulfate. The solvent was evaporated under reduced pressure, and the residue was purified by silica gel column chromatography (n-hexane:ethyl acetate=20:1), to thereby yield 1.83 g of the target compound as pale yellow oily matter (yield: 61.6%).

$^1$H-NMR (CDCl$_3$, ppm); 1.32 (9H, s), 2.13 (3H, s), 2.19 (3H, s), 3.48 (2H, s), 3.50 (2H, s), 5.11 (1H, t, J=1.35 Hz), 5.37 (1H, s), 7.26~7.36 (5H, m), 7.44 (1H, s), 7.46 (1H, s).

Example 95

Production of 2-[3-Isopropenyl-5-{N-(4-tert-butylbenzyl)-N-methylaminomethyl}phenyl]-2-propanol (Compound 142)

Compound 67 (0.80 g; 2.07 mmol) was dissolved in tetrahydrofuran (15 ml). While the solution was stirred at −78° C. under nitrogen atmosphere, n-butyl lithium in n-hexane (1.63 M: 1.3 ml; 2.1 mmol) was slowly added dropwise. After 10 minutes, acetone (0.5 ml) was added dropwise thereto, and the mixture was gradually brought to room temperature. Reaction was stopped by dropwise addition of saturated aqueous ammonium chloride solution, and the mixture was extracted with diethyl ether (100 ml). The organic layer was washed with saturated brine, and dried over sodium sulfate. The solvent was evaporated under reduced pressure, and the residue was purified by silica gel column chromatography (n-hexane:ethyl acetate=5:1→2:1), to thereby yield 0.28 g of the target compound (yield: 37.0%).

$^1$H-NMR (CDCl$_3$, ppm); 1.31 (9H, s), 1.60 (6H, s), 2.18 (3H, s), 2.21 (3H s), 3.48 (2H, s), 3.54 (2H, s), 5.09 (1H, s), 5.38 (1H, s), 7.26~7.48 (7H, m).

Example 96

Production of N-(4-tert-Butylbenzyl)-N-methyl-(3,5-bisisopropenylbenzyl)amine (Compound 143)

Compound 142 (0.28 g; 7.66×10$^{-1}$ mmol) and phosphorus oxychloride (0.59 g; 3.83 mmol) was added dropwise to pyridine (15 ml), and the mixture was refluxed for 2 hours. The mixture was brought to room temperature, and poured into ice/water. The pH of the mixture was adjusted to weak alkaline by use of sodium carbonate, followed by extraction with chloroform (50 ml). The organic layer was washed with saturated aqueous sodium bicarbonate solution and then with saturated brine, and dried over sodium sulfate. The solvent was evaporated under reduced pressure, and the residue was purified by silica gel column chromatography (n-hexane:ethyl acetate=5:1), to thereby yield 0.18 g of the target compound (yield: 67.6%).

IR (Nujol, cm$^{-1}$); 2964, 2906, 2870, 2284, 1591, 1450, 1364, 1269, 1135, 1111, 1031, 1020, 885; $^1$H-NMR (CDCl$_3$, ppm); 1.28 (9H, s), 2.18 (3H×2, s), 2.21 (3H, s), 3.50 (2H, s), 3.54 (2H, s), 5.09 (1H, s), 5.38 (1H, s), 7.26~7.38 (6H, m), 7.43 (1H, m).

Example 97

According to the following formulation, polystyrene beads and Compound 3 or 77 were admixed, and the admixture was subjected to melt molding, to thereby obtain a toothbrush handle.

| <Formulation> | |
| --- | --- |
| Polystyrene beads | 99 parts by weight (pbw) |
| Compound 3 or 77 | 1 pbw |

Example 98

According to the following formulation, polystyrene beads and Compound 10 or 81 were admixed, and the admixture was subjected to melt molding, to thereby obtain a toothbrush handle.

| <Formulation> | |
|---|---|
| Polystyrene beads | 90 pbw |
| Compound 10 or 81 | 10 pbw |

Example 99

According to the following formulation, the ingredients were weighed and admixed, and the admixture was kneaded in a kneader, to thereby obtain Athlete's foot ointment.

| <Formulation> | |
|---|---|
| VASELINE | 99 pbw |
| Compound 12 or 81 | 1 pbw |

Example 100

According to the following formulation, the ingredients were weighed and admixed, and the admixture was kneaded in a kneader, to thereby obtain Athlete's foot ointment.

| <Formulation> | |
|---|---|
| Absorption ointment | 99 pbw |
| Compound 19 or 88 | 1 pbw |

Example 101

The following ingredients were stirred and solubilized, to thereby obtain a liquid preparation.

| <Formulation> | |
|---|---|
| Ethanol | 92 pbw |
| Methacrylic acid alkyl ester copolymer | 2 pbw |
| Compound 25 or 91 | 1 pbw |
| Propylene glycol | 5 pbw |

Example 102

The following ingredients were stirred and solubilized, to thereby obtain a liquid preparation.

| <Formulation> | |
|---|---|
| Ethanol | 92 pbw |
| Methacrylic acid alkyl ester copolymer | 2 pbw |
| Compound 27 or 95 | 1 pbw |
| Propylene glycol | 5 pbw |

Test Example 1

Measurement of Antifungal Activity (Measurement of Minimum Inhibitory Concentration)

Antifungal activity of representative compounds of the present invention against dermatophytes was investigated.

Briefly, strains of dermatophytes to be tested were grown on slant media prepared with Sabouraud's agar (product of Nissuiseiyaku; pepton 1.0%, glucose 4.0%, agar 1.5%, pH 5.9) at 27° C. for two weeks, so as to allow sufficient production of conidiospores. Subsequently, sterilized saline solution containing 0.05% (wt/vol) TWEEN 80 was added thereto, and while the surface of the each medium was scraped with a platinum loop, the conidiospores were deaggregated and suspended in the saline solution. The suspension was filtered through a double face sterilized gauze sheet so as to remove agar and hypha pellets. The filtrate was diluted with a saline solution so as to make the concentration of the conidiospores decrease to $10^6$/ml by use of a cytometer, and the resultant dilute filtrate served as a test dermatophytes solution. Meanwhile, a stock solution was prepared by adding 1 ml of dimethylsulfoxide to 10 mg of a compound to be tested. An aliquot (500 μl) of the stock solution was combined with dimethylsulfoxide (500 μl), to thereby prepare a 2-fold dilute solution. Dilution was similarly repeated until 13 different dilute solutions ranging from 10 to 0.0025 mg/ml (concentrations of the ultimate test system: 100–0.025 μg/ml) were obtained. 100 μl each of the diluted solutions of the test compound was dispensed into the sterilized petri dish. A Sabouraud's agar (pepton 1.0%, glucose 4.0%, agar 1.5%, pH 5.9; 10 ml), which had been sterilized and dissolved, was added thereto, and the mixture was thoroughly mixed and solidified. Next, the above-prepared test dermatophytes solution was planted in amounts of 5 μl by use of a microplanter. Incubation was continued for one week at 27° C., and the minimum compound concentration (μg/ml) that definitely inhibited any visible growth was taken as an MIC value. The results are shown in Tables 1 and 2.

TABLE 1

| | | | | | | | | | | | | (μg/ml) |
|---|---|---|---|---|---|---|---|---|---|---|---|---|
| | Com. 3 | Com. 10 | Com. 12 | Com. 19 | Com. 25 | Com. 27 | Com. 39 | Com. 45 | Com. 48 | Com. 52 | Com. 64 | Com. 74 |
| T. mentagrophytes IF05811 | 0.1 | 0.39 | 0.39 | 0.1 | 0.78 | 1.56 | 6.25 | 0.39 | 6.25 | 12.5 | 0.1 | 6.25 |
| T. mentagrophytes IF07552 | 0.2 | 0.39 | 0.39 | 0.05 | 0.78 | 1.56 | 6.25 | 0.39 | 3.12 | 12.5 | 0.1 | 12.5 |
| T. mentagrophytes TIMM1177 | 0.1 | 0.39 | 0.78 | 0.1 | 0.78 | 1.56 | 6.25 | 0.39 | 6.25 | 12.5 | 0.1 | 12.5 |
| T. mentagrophytes TIMM1189 | 0.2 | 0.39 | 0.39 | 0.05 | 0.78 | 1.56 | 6.25 | 0.39 | 6.25 | 12.5 | 0.1 | 6.25 |
| T. rubrum IF05808 | 0.1 | 0.39 | 0.39 | 0.1 | 0.78 | 1.56 | 3.12 | 0.39 | 1.56 | 12.5 | 0.1 | 1.56 |
| T. rubrum | 0.1 | 0.39 | 0.2 | 0.1 | 0.78 | 1.56 | 3.12 | 0.39 | 1.56 | 12.5 | 0.1 | 3.12 |

TABLE 1-continued

| | Com. 3 | Com. 10 | Com. 12 | Com. 19 | Com. 25 | Com. 27 | Com. 39 | Com. 45 | Com. 48 | Com. 52 | Com. 64 | (μg/ml) Com. 74 |
|---|---|---|---|---|---|---|---|---|---|---|---|---|
| IF09185 | | | | | | | | | | | | |
| T. violaceum TIMM1264 | 0.1 | 0.78 | 0.39 | 0.1 | 0.78 | 1.56 | 12.5 | 0.39 | 6.25 | 12.5 | 0.2 | 6.25 |
| H. gypseum IF08231 | 0.39 | 0.78 | 0.78 | 0.2 | 3.12 | 6.25 | 12.5 | 0.39 | 6.25 | 3.12 | 0.39 | 12.5 |
| M. canis TIMM0760 | 0.1 | 0.2 | 0.2 | 0.1 | 0.39 | 0.78 | 6.25 | 0.2 | 1.56 | N.E. | 0.2 | 1.56 |

Com. = Compound
N.E. = not evaluated

TABLE 2

| | Com. 77 | Com. 81 | Com. 88 | Com. 95 | Com. 97 | Com. 101 | Com. 108 | Com. 114 | (μg/ml) Com. 126 |
|---|---|---|---|---|---|---|---|---|---|
| T. mentagrophytes IF05811 | 0.39 | 0.39 | 0.1 | 1.56 | 1.56 | 0.1 | 1.56 | 0.78 | 12.5 |
| T. mentagrophytes IF07552 | 0.1 | 0.39 | 0.05 | 0.78 | 3.12 | 0.1 | 1.56 | 0.39 | 3.12 |
| T. mentagrophytes TIMM1177 | 0.2 | 0.39 | 0.1 | 0.78 | 1.56 | 0.2 | 3.12 | 0.39 | 12.5 |
| T. mentagrophytes TIMM1189 | 0.2 | 0.78 | 0.05 | 0.78 | 0.78 | 0.1 | 1.56 | 0.39 | 3.12 |
| T. rubrum IF05808 | 0.1 | 0.2 | 0.05 | 0.39 | 1.56 | 0.05 | 0.78 | 0.2 | 3.12 |
| T. rubrum IF09185 | 0.1 | 0.39 | 0.05 | 0.39 | 0.78 | 0.1 | 0.78 | 0.2 | 3.12 |
| T. violaceum TIMM1264 | 0.2 | 0.78 | 0.1 | 0.78 | 1.56 | 0.1 | 3.12 | 0.39 | 3.12 |
| M. gypseum IF08231 | 0.39 | 0.39 | 0.1 | 3.12 | 3.12 | 0.2 | 1.56 | 0.2 | 6.25 |
| M. canis TIMM0760 | 0.2 | 0.2 | 0.05 | 0.2 | 0.39 | 0.1 | 1.56 | 0.2 | 1.56 |

Com. = Compound

Industrial Applicability

The amine derivatives (1) or salts thereof are endowed with excellent antifungal activity, and therefore are very useful as antifungal agents, antifungal compositions, drugs, and similar materials.

What is claimed is:

1. An amine of formula (1):

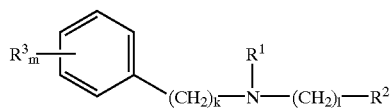

(1)

wherein
R$^1$ represents a C1–C4 linear, branched, or cyclic alkyl group;
R$^2$ represents a group represented by (i);
(i)

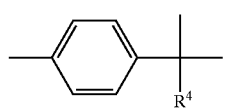

(i)

R$^3$ represents a C1–C3 linear, branched, or cyclic alkyl group, a hydroxylated C1–C5 linear, branched, or cyclic alkyl group, a C1–C5 linear, branched, or cyclic acyl group, a formyl group, an acetyl group, a propionyl group, a C2–C5 linear, branched, or cyclic alkenyl group, or a halogen atom; R$^3$ in the number of m may be identical to or different from one another, and when R$^3$ is alkyl, m is at least 2 and at least one R$^3$ is alkenyl; or when R$^3$ is halogen, m is at least 2 and at least one R$^3$ is alkenyl or alkyl, k, l, and m are each an integer of 1 to 4;
R$^4$ represents a C1–C4 linear alkyl group or phenyl group; or a salt thereof.

2. The amine according to claim 1, wherein
at least one R$^1$ represents a methyl group, an ethyl group, an isopropyl group, or a cyclopropyl group;
R$^4$ represents a methyl group or a phenyl group; and
R$^3$ represents a methyl group, a 1-hydroxy-1-methylethyl group, a 1,2-dimethyl-1-hydroxypropyl group, a 1-hydroxypropyl group, a formyl group, an acetyl group, a propionyl group, a vinyl group, an isopropenyl group, a 2-methyl-1-propenyl group, a 1-ethylvinyl group, a 1-methyl-1-propenyl group, a 1-isopropylvinyl group, a fluorine atom or a bromine atom.

3. An antifungal agent comprising the amine according to claim 1, or a salt thereof.

4. A pharmaceutical composition comprising the amine according to claim 1 or a salt thereof, and a pharmaceutically acceptable carrier or excipient.

5. A method for the treatment of a fungal infectious disease comprising
administering a composition comprising the amine according to claim 1, or a salt thereof, to a patient in need thereof.

6. A moldable composition comprising a thermoplastic material and the amine according to claim 1 or a salt thereof.

7. An amine of formula (2):
wherein

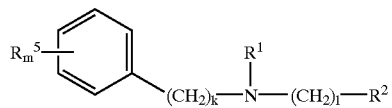

(2)

$R^1$ represents a C1–C4 linear, branched, or cyclic alkyl group;

$R^2$ represents a group represented by (ii);

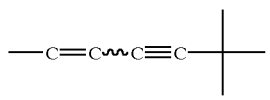

(ii)

$R^5$ represents a C1–C3 linear, branched, or cyclic alkyl group, a hydroxylated C1–C5 linear, branched, or cyclic alkyl group, a C2–C5 linear, branched, or cyclic alkenyl group, an acetyl group, a propionyl group, or a halogen atom; $R^5$ in the number of m may be identical to or different from one another, and when $R^5$ is halogen, m is 2, 3 or 4 and at least one $R^5$ is alkenyl or alkyl; or when $R^5$ is alkyl, m is at least two and at least one $R^5$ is alkenyl; or when $R^5$ is hydroxylated, m is at least two and at least one $R^5$ is alkyl;

k, l, and m are each an integer of 1 to 4; and $R^4$ represents a C1–C4 linear alkyl group or phenyl group, or a salt thereof.

8. The amine according to claim 7, wherein
at least one $R^5$ represents a methyl group, a 1-hydroxy-1-methylethyl group, a 1,2-dimethyl-1-hydroxypropyl group, an acetyl group, a propionyl group, a vinyl group, an isopropenyl group, a 2-methyl-1-propenyl group, a 1-ethylvinyl group, a 1-methyl-1-propenyl group, a 1-isopropylvinyl group, a fluorine atom or a bromine atom.

9. An antifungal agent comprising the amine according to claim 7, or a salt thereof.

10. A pharmaceutical composition comprising the amine according to claim 7, or a salt thereof, and a pharmaceutically acceptable carrier or excipient.

11. A method for the treatment of a fungal infectious disease comprising
administering a composition comprising the amine according to claim 7, or a salt thereof, to a patient in need thereof.

12. A moldable composition comprising a thermoplastic material and the amine according to claim 7, or a salt thereof.

13. An amine of formula (3):

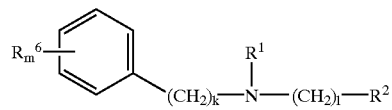

(3)

wherein $R^1$ represents a C1–C4 linear, branched, or cyclic alkyl group;

$R^2$ represents a group represented by (iii);

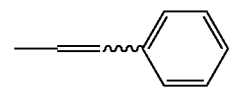

(iii)

$R^6$ represents a hydroxylated C1–C5 linear, branched, or cyclic alkyl group, a C1–C5 linear, branched, or cyclic acyl group; $R^6$ in the number of m may be identical to or different from one another;

k, l, and m are each an integer of 1 to 4; and $R^4$ represents a C1–C4 linear alkyl group or phenyl group, or a salt thereof.

14. An antifungal agent comprising the amine according to claim 13, or a salt thereof.

15. A pharmaceutical composition comprising the amine according to claim 13, or a salt thereof, and a pharmaceutically acceptable carrier or excipient.

16. A method for the treatment of a fungal infectious disease comprising administering a composition comprising the amine according to claim 13, or a salt thereof, to a patient in need thereof.

17. A moldable composition comprising a thermoplastic material and the amine according to claim 13 or a salt thereof.

18. The amine of claim 7, wherein $R^5$ is a C2–C5 linear, branched or cyclic alkenyl group.

* * * * *